US011230583B2

(12) United States Patent
Harrison et al.

(10) Patent No.: US 11,230,583 B2
(45) Date of Patent: Jan. 25, 2022

(54) INHIBIN ANALOGS

(71) Applicant: Hudson Institute of Medical Research, Clayton (AU)

(72) Inventors: Craig Harrison, Nunawading (AU); Kelly Walton, Lilydale (AU)

(73) Assignee: Hudson Institute of Medical Research, Clayton (AU)

(*) Notice: Subject to any disclaimer, the term of this patent is extended or adjusted under 35 U.S.C. 154(b) by 196 days.

(21) Appl. No.: 15/779,143

(22) PCT Filed: Nov. 25, 2016

(86) PCT No.: PCT/AU2016/051156
§ 371 (c)(1),
(2) Date: May 25, 2018

(87) PCT Pub. No.: WO2017/088027
PCT Pub. Date: Jun. 1, 2017

(65) Prior Publication Data
US 2018/0273599 A1 Sep. 27, 2018

(30) Foreign Application Priority Data

Nov. 26, 2015 (AU) ................................ 2015904898

(51) Int. Cl.
| C07K 14/575 | (2006.01) |
| C12N 15/63 | (2006.01) |
| C12N 15/11 | (2006.01) |
| A61K 38/00 | (2006.01) |
| A61K 38/22 | (2006.01) |
| A61K 38/17 | (2006.01) |
| A61K 38/16 | (2006.01) |

(52) U.S. Cl.
CPC ............ *C07K 14/575* (2013.01); *A61K 38/00* (2013.01); *A61K 38/16* (2013.01); *A61K 38/17* (2013.01); *A61K 38/22* (2013.01); *C12N 15/11* (2013.01); *C12N 15/63* (2013.01); *C07K 2319/21* (2013.01); *C07K 2319/43* (2013.01)

(58) Field of Classification Search
None
See application file for complete search history.

(56) References Cited

U.S. PATENT DOCUMENTS

| 4,016,043 A | 4/1977 | Schuurs et al. |
| 4,018,653 A | 4/1977 | Mennen |
| 4,424,279 A | 1/1984 | Bohn et al. |
| 4,873,192 A | 10/1989 | Kunkel |
| 5,288,931 A * | 2/1994 | Chang ................. C07K 1/1133 |
| | | 435/69.1 |
| 7,112,660 B1 * | 9/2006 | Domingues ........ C07K 14/5406 |
| | | 530/351 |
| 2003/0045474 A1 * | 3/2003 | Sailer ...................... A61P 19/00 |
| | | 514/8.8 |
| 2010/0092463 A1 | 4/2010 | Ishikawa et al. |

FOREIGN PATENT DOCUMENTS

| WO | 93011247 A1 | 6/1993 |
| WO | 97015321 A1 | 5/1997 |
| WO | 2014182676 A2 | 11/2014 |

OTHER PUBLICATIONS

Tokuriki et al., 2009, Curr. Opin. Struc. Biol. 19:596-604.*
Bhattacharya et al., 2017, PLoS ONE 12(3): e0171355, https://doi.org/10.1371/journal.pone.0171355.*
Alaoui-Ismaili, 2009, Cytokine Growth Factor Rev. 20(5-6):501-7.*
Guo et al., 2004, PNAS USA 101(25):9205-10.*
Ulloa-Aguirre et al., 2004, Traffic 5:821-837.*
Bernier et al., 2004, Curr. Opin. Pharmacol. 4:528-533.*
International Search Report for Application No. PCT/AU2016/051156 dated Mar. 9, 2017, 9 pages.
Altschul et al., "Gapped BLAST and PSI-BLAST: A New Generation of Protein Database Search Programs", Nucl. Acids. Res., vol. 25, No. 17, 1997, p. 3389.
Antenos et al., "An Activin/Furin Regulatory Loop Modulates the Processing and Secretion of Inhibin α- and βB-Subunit Dimers in Pituitary Gonadotrope Cells", J. Biol. Chem., 2008, vol. 283, No. 48, pp. 33059-33068.
Antenos et al., "Role of PCSK5 Expression in Mouse Ovarian Follicle Development: Indentification of the Inhibin α- and β-Subunits as Candidate Substrates", PLoS One, 2011, vol. 6, Issue 3, p. 17348.
Bernard, DJ, "Disinhibiting an Inhibitor: Genetic Engineering Leads to Improvements in Recombinant Inhibin A Production", Endocrinology, Jul. 2016, vol. 157, vol. 7, pp. 2583-2585.
Chantry et al., "Inhibiting Activin-A Signaling Stimulates Bone Formation and Prevents Cancer-Induced Bone Destruction In Vivo", J. Bone Min. Res., 2010, vol. 25, No. 12, pp. 2633-2646.
Constam, "Regulation of TGFβ and Related Signals by Precursor Processing", Stem Cell Dev. Biol., 2014, vol. 32, pp. 85-97.
Duckert, P. et al., "Prediction of Proprotein Convertase Cleavage Sites", Protein Engineering, Design and Selection: PEDS, 2004, vol. 17, No. 1, pp. 107-112.
Fredericks, D. et al., Optimization of the Expression of Recombinant Human Activin A in the Yeast *Pichia pastoris*, Biotechnology Progress, 2010, vol. 26, No. 2, pp. 372-383.
Abstract of Groome et al., "Detection of Dimeric Inhibin Throughout the Human Menstrual Cycle by Two-Site Enzyme Immunoassay", Clin. Endocrinol., 1994, vol. 40, pp. 717-723, 3 pages.

(Continued)

Primary Examiner — Elizabeth C. Kemmerer
(74) Attorney, Agent, or Firm — Howard & Howard Attorneys PLLC

(57) ABSTRACT

The present invention relates to inhibin analogs, their method of production and their use in the treatment and prophylaxis of disease or conditions associated with reduced levels of inhibin and activin-mediated signaling.

21 Claims, 14 Drawing Sheets

Specification includes a Sequence Listing.

(56) References Cited

OTHER PUBLICATIONS

Abstract of Harrison et al., "Antagonists of Activin Signaling: Mechanisms and Potential Biological Applications", Trends Endocrinol. Metab., 2005, vol. 16, No. 2, pp. 73-78, 1 page.
Harrison et al., "Identification of a Functional Binding Site for Activin on the Type I Receptor ALK4", J. Biol. Chem., 2003, vol. 278, No. 23, pp. 21129-21135.
Abstract of Harrison et al., Prodomains Regulate the Synthesis, Extracellular Localisation and Activity of TGF-ß Superfamily Ligands, Growth Factors, 2011, vol. 29, Issue 5, pp. 174-186, 2 pages.
Kohler et al., "Continuous Cultures of Fused Cells Secreting Antibody of Predefined Specificity", Nature, 1975, vol. 256, No. 5517, pp. 495-497.
Abstract of Kohler et al., "Fusion Between Immunoglobulin-Secreting and Nonsecreting Myeloma Cell Lines", European Journal of Immunology, 1976, vol. 6, pp. 511-519, 2 pages.
Abstract of Kunkel et al., "Rapid and Efficient Site-Specific Mutagenesis Without Phenotypic Selection", Methods in Enzymology, 1987, vol. 154, pp. 367-382, 1 page.
Kunkel, "Rapid and Efficient Site-Specific Mutagenesis Without Phenotype Selection", Proc. Natl. Acad. Sci. USA, 1985, vol. 82, pp. 488-492.
Abstract of Lewis et al., "Betaglycan Blinds Inhibin and Can Mediate Functional Antagonism of Activin Signalling", Nature, 2000, vol. 404, pp. 411-414, 1 page.
Li et al., "Prevention of Cachexia-Like Syndrome Development and Reduction of Tumor Progression in Inhibin-Deficient Mice Following Administration of Chimeric Activin Receptor Type II_Murine Fc Protein", Mol. Human. Reprod., 2007, vol. 13, No. 9, pp. 675-683.
Lotinun et al., "Activin Receptor Signaling: A Potential Therapeutic Target for Osteoporosis", Curr. Mol. Pharmacol., 2012, vol. 5, pp. 195-204.
Makanji et al., "Inhibin A and B in Vitro Bioactivities are Modified by Their Degree of Glycosylation and Their Affinities of Betaglycan", Endocrinology, 2007, vol. 148, No. 5, pp. 2309-2316.
Makanji et al., "Inhibin B is a More Potent Suppressor of Rat Follicle-Stimulating Hormone Release than Inhibin A In Vitro and In Vivo", Endocrinology, 2009, vol. 150, No. 10, pp. 4784-4793.
Makanji et al., "Suppression of Inhibin A Biological Activity by Alterations in the Binding Site for Betaglycan", J. Biol. Chem., 2008, vol. 283, No. 24, pp. 16743-16751.
Massague et al., "Transcriptional Control by the TGF-?/Smad Signaling System", The EMBO Journal, vol. 19, No. 8, pp. 1745-1754.
Matzuk et al., "Development of Cancer Cachexia-Like Syndrome and Adrenal Tumors in Inhibin-Deficient Mice", Proc. Natl. Acad. Sci. USA, 1994, vol. 91, No. 19, pp. 8817-8821, 2 pages.
Abstract of Matzuk et al.,"α-Inhibin is a Tumour-Suppressor Gene With Gonadal Specificity in Mice," Nature, 1992, vol. 360, pp. 313-319, 1 page.
Mottershead et al., "Cumulin, an Oocyte-Secreted Heterodimer of the Transforming Growth Factor-ß Family, is a Potent Activator of Granulosa Cells and Improves Oocyte Quality", J. Biol. Chem., 2015, vol. 290, No. 39, pp. 24007-24020.
Pangas, SA et al., "Production and Purification of Recombinant Human Inhibin and Activin", The Journal of Endocrinology, 2002, vol. 172, No. 1, pp. 199-210.
Papakonstantinou, T. et al., "Synthesis, Purification and Bioactivity of Recombinant Human Activin A Expressed in the Yeast *Pichia Pastoris*", Protein Expression and Purification, 2009, vol. 64, No. 2, pp. 131-138.
Pearsall et al., "A Soluble Activin Type IIA Receptor Induces Bone Formation and Improves Skeletal Integrity", Proc. Natl. Acad. Sci. USA, 2008, vol. 105, No. 19, pp. 7082-7087.

Perrien et al., "Bone Turnover Across the Menopause Transition: Correlations with Inhibins and Follicle-Stimulating Hormone", J. Clin. Endocrinol Metab., 2006, vol. 91, No. 5, pp. 1848.1854.
Perrien et al., "Inhibin A Enhances Bone Formation During Distraction Osteogenesis", J. Orthopaed. Res., 2012, vol. 30, pp. 288-295.
Perrien et al., "Inhinbin A is an Endocrine Stimulator of Bone Mass and Strength", Endocrinology, 2007, vol. 148, No. 4, pp. 1654-1665.
Abstract of QIAO et al., Myostatin Propeptide Gene Delivery by Adeno-Associated Virus Serotype 8 Vectors Enhances Muscle Growth and Ameliorates Dystrophic Phenotypes in mdx Mice, Human Gene Therapy, 2008, vol. 19, No. 3, 1 page.
Abstract of Roberge et al., "A Strategy for a Convergent Synthesis of N-Linked Glycopeptides on a Solid Support", Science, 1995, vol. 269, Issue 5221, p. 202, 1 page.
Abstract of Robertson et al., "A Proposed Classification System for Menstrual Cycles in the Menopause Transition Based on Changes in Serum Hormone Profiles", Menopause, 2008, vol. 15, No. 6, pp. 1139-1144, 1 page.
Robertson et al., "Latent TGF-ß-Binding Proteins", Matrix Biol., 2015, vol. 47, pp. 44-53.
Abstract of Scott et al., "A Simple and Rapid in Vitro Bioassay for Inhibin", Endocrinology, 1980, vol. 107, Issue 5, pp. 1536-1542, 2 pages.
Abstract of Sengle et al., "A New Model for Growth Factor Activation: Type II Receptors Compete with the Prodomain for BMP-7,", J. Mol. Biol., 2008, vol. 381, Issue 4, pp. 1025-1039, 2 pages.
Sengle et al., "Prodomains of Transforming Growth Factor ß (TFGß) Superfamily Members Specify Different Functions", J. Mol. Biol., 2011, vol. 286, No. 7, pp. 5087-5099.
Abstract of Shi et al.,"Latent TGF-ß Structure and Activation", Nature, 2011, vol. 474, pp. 343-349, 1 page.
Van Casteren et al., "Development of Time-Resolved Immunofluorometric Assays for Rat Follicle-Stimulating Hormone and Luteinizing Hormone and Application on Sera of Cycling Rats", Biol. Reprod., 2000, vol. 62, pp. 886-894.
Walton, KL et al., "A Common Biosynthetic Pathway Governs the Dimerization and Secretion of Inhibin and Related Transforming Growth Factor Beta (TGFbeta) Ligands", Journal of Biological Chemistry, 2009, vol. 284, No. 14, pp. 9311-9320.
Walton, KL et al., "A Novel, More Efficient Approach to Generate Bioactive Inhibins", Endocrinology, Jul. 2016, vol. 157, No. 7, pp. 2799-2809.
Walton et al., "Inhibin Biosynthesis and Activity Are Limited by a Prodomain-Derived Peptide", Endocrinology, 2015, vol. 156, No. 8, pp. 3047-3057.
Abstract of Walton et al., "Use of Detergent-Based Buffers Allows Detecton of Precursor Inhibin Forms in an Immunoassay Format", Mol. Cell Endocrinol., 2013, vol. 381, Issues 1-2, pp. 106-114, 2 pages.
Wiater et al., "Endogenous Betaglycan Is Essential for High-Potency Inhibin Antagonism in Gonadotropes", Mol. Endocrinol, 2009, vol. 23, vol. 7, pp. 1033-1042.
Wiater et al., "Inhibin Is An Antagonist of Bone Morphogenetic Protein Signaling", J. Biol. Chem., 2003, vol. 278, No. 10, pp. 7934-7941.
Woodruff et al., Inhibin A and Inhibin B Are Inversely Correlated to Follicle-Stimulating Hormone, Yet are Discordant During the Follicular Phase of the Rat Estrous Cycle, and Inhibin A is Expressed in a Sexually Dimorphic Manner, Endocrinology, 1996, vol. 137, No. 12, pp. 5463-5467.

* cited by examiner

Human inhibin βA-subunit super-cut variant + M418A mutation

```
atgcccttgctttggctgagaggatttctgttggcaagttgctggattatagtgaggagt
 M  P  L  L  W  L  R  G  F  L  L  A  S  C  W  I  I  V  R  S
gactacaaagacgacgacgacaaatcccccacccaggatccgaggggcacagcgcggcc        FLAG tag
 D  Y  K  D  D  D  K  S  P  T  P  G  S  E  G  H  S  A  A
cccgactgtccgtcctgtgcgctggccgccctcccaaaggatgtacccaactctcagcca
 P  D  C  P  S  C  A  L  A  A  L  P  K  D  V  P  N  S  Q  P
gagatggtggaggccgtcaagaagcacatttaaacatgctgcacttgaagaagagaccc
 E  M  V  E  A  V  K  K  H  I  L  N  M  L  H  L  K  K  R  P
gatgtcacccagccggtacccaaggcggcgcttctgaacgcgatcagaaagcttcatgtg
 D  V  T  Q  P  V  P  K  A  A  L  L  N  A  I  R  K  L  H  V
ggcaaagtcggggagaacgggtatgtggagatagaggatgacattggaaggagggcagaa
 G  K  V  G  E  N  G  Y  V  E  I  D  D  I  G  R  R  A  E
atgaatgaacttatggagcagacctcggagatcatcacgtttgccgagtcaggaacagcc
 M  N  E  L  M  E  Q  T  S  E  I  I  T  F  A  E  S  G  T  A
aggaagacgctgcacttcgagatttccaaggaaggcagtgacctgtcagtggtggagcgt
 R  K  T  L  H  F  E  I  S  K  E  G  S  D  L  S  V  V  E  R
gcagaagtctggctcttcctaaaagtccccaaggccaacaggaccaggaccaaagtcacc
 A  E  V  W  L  F  L  K  V  P  K  A  N  R  T  R  T  K  V  T
atccgcctcttccagcagcagaagcacccgcagggcagcttggacacaggggaagaggcc
 I  R  L  F  Q  Q  Q  K  H  P  Q  G  S  L  D  T  G  E  E  A
gaggaagtgggcttaaaggggagaggagtgaactgttgctctctgaaaaagtagtagac
 E  E  V  G  L  K  G  E  R  S  E  L  L  L  S  E  K  V  V  D
gctcggaagagcacctggcatgtcttccctgtctccagcagcatccagcggttgctggac
 A  R  K  S  T  W  H  V  F  P  V  S  S  S  I  Q  R  L  L  D
cagggcaagagctcctggacgttcggattgcctgtgagcagtgccaggagagtggcgcc
 Q  G  K  S  S  L  D  V  R  I  A  C  E  Q  C  Q  E  S  G  A
agcttggttctcctgggcaagaagaagaagaaagaagaggaggggaagggaaaaagaag
 S  L  V  L  L  G  K  K  K  K  E  E  G  E  G  K  K  K
ggcggaggtgaaggtggggcaggagcagatgaggaaaaggagcagtcgcacagacctttc
 G  G  G  E  G  G  A  G  A  D  E  E  K  Q  S  H  R  P  F
ctcatgctgcaggcccggcagtctgaagaccaccctcatatctcatcgagaaagaaacgc      ◄ Super-cut site
 L  M  L  Q  A  R  Q  S  E  D  H  P  H  I  S  R  K  K  R
tcagtctcatcgggcttggagtgtgatggcaaggtcaacatctgctgtaagaaacagttc
 S  V  S  S  G  L  E  C  D  G  K  V  N  I  C  C  K  K  Q  F
tttgtcagtttcaaggacatcggctggaatgactggatcattgctccctctggctatcat
 F  V  S  F  K  D  I  G  W  N  D  W  I  I  A  P  S  G  Y  H
gccaactactgcgagggtgagtgcccgagccatatagcaggcacgtccgggtcctcactg
 A  N  Y  C  E  G  E  C  P  S  H  I  A  G  T  S  G  S  S  L
tccttccactcaacagtcatcaaccactaccgcatgcggggccatagccctttgccaac
 S  F  H  S  T  V  I  N  H  Y  R  M  R  G  H  S  P  F  A  N
ctcaaatcgtgctgtgtgcccaccaagctgagacccatgtccatgttgtactatgatgat
 L  K  S  C  C  V  P  T  K  L  R  P  M  S  M  L  Y  Y  D  D
ggtcaaaacatcatcaaaaaggacattcagaacgcgatcgtggaggagtgtgggtgctca
 G  Q  N  I  I  K  K  D  I  Q  N  A  I  V  E  E  C  G  C  S
tag                                                    ↘ M418A mutation
```

Figure 7

Human inhibin α-subunit_super-cut 1 variant

```
atggtgctgcacctactgctcttcttgctgctgaccccacagggtgggcacagctgccag
 M  V  L  H  L  L  F  L  L  L  T  P  Q  G  G  H  S  C  Q
gggctggagctggcccgggaacttgttctggccaaggtgagggccctgttcttggatgcc
 G  L  E  L  A  R  E  L  V  L  A  K  V  R  A  L  F  L  D  A
ttggggccccccgcggtgaccagggaaggtggggaccctggagtcaggcggctgccccga
 L  G  P  P  A  V  T  R  E  G  D  P  G  V  R  R  L  P  R
agacatgccctggggggcttcacacacaggggctctgagcccgaggaagaggaggatgtc
 R  H  A  L  G  G  F  T  H  R  G  S  E  P  E  E  E  D  V
tcccaagccatccttttcccagccacagatgccagctgtgaggacaagtcagctgccaga
 S  Q  A  I  L  F  P  A  T  D  A  S  C  E  D  K  S  A  A  R
gggctggccaggaggctgaggagggcctcttcagatacatgttccggccatcccagcat
 G  L  A  Q  E  A  E  E  G  L  F  R  Y  M  F  R  P  S  Q  H
acacgcagccgccaggtgacttcagcccagctgtggttccacaccgggctggacaggcag
 T  R  S  R  Q  V  T  S  A  Q  L  W  F  H  T  G  L  D  R  Q
ggcacagcagcctccaatagctctgagcccctgctaggcctgctggcactgtcaccggga
 G  T  A  A  S  N  S  S  E  P  L  L  G  L  L  A  L  S  P  G
ggacccgtggctgtgcccatgtctttgggccatgctccccctcactgggccgtgctgcac
 G  P  V  A  V  P  M  S  L  G  H  A  P  P  H  W  A  V  L  H
ctggccacctctgctctctctctgctgacccaccccgtcctggtgctgctgctgcgctgt
 L  A  T  S  A  L  S  L  L  T  H  P  V  L  V  L  L  R  C
cccctctgtacctgctcagcccggcctgaggccacgcccttcctggtggcccacactcgg          Poly-histidine
 P  L  C  T  C  S  A  R  P  E  A  T  P  F  L  V  A  H  T  R          TAG (x9)
accagaccacccagtggaggggagcatcatcaccatcaccaccatcatcacatctcatcg
 T  R  P  P  S  G  G  E  H  H  H  H  H  H  H  H  I  S  S       Super-cut site1
agaaagaaacgctcagtctcatcaactccctgatgtcctggccttggtctccctctgct
 R  K  K  R  S  V  S  S  T  P  L  M  S  W  P  W  S  P  S  A
ctgcgcctgctgcagaggcctccggaggaaccggctgcccatgccaactgccacagagta
 L  R  L  L  Q  R  P  P  E  E  P  A  A  H  A  N  C  H  R  V
gcactgaacatctccttccaggagctgggctgggaacggtggatcgtgtaccctcccagt
 A  L  N  I  S  F  Q  E  L  G  W  E  R  W  I  V  Y  P  P  S
ttcatcttccactactgtcatggtggttgtgggctgcacatcccaccaaacctgtccctt
 F  I  F  H  Y  C  H  G  G  C  G  L  H  I  P  P  N  L  S  L
ccagtccctggggctcctcctaccccagcccagccctactccttgctgccaggggccag
 P  V  P  G  A  P  P  T  P  A  Q  P  Y  S  L  L  P  G  A  Q
ccctgctgtgctgctctcccagggaccatgaggcccctacatgtccgcaccacctcggat
 P  C  C  A  A  L  P  G  T  M  R  P  L  H  V  R  T  T  S  D
ggaggttactctttcaagtatgagacagtgcccaaccttctcacgcagcactgtgcttgt
 G  G  Y  S  F  K  Y  E  T  V  P  N  L  L  T  Q  H  C  A  C
atctaa
 I  -
```

Figure 8

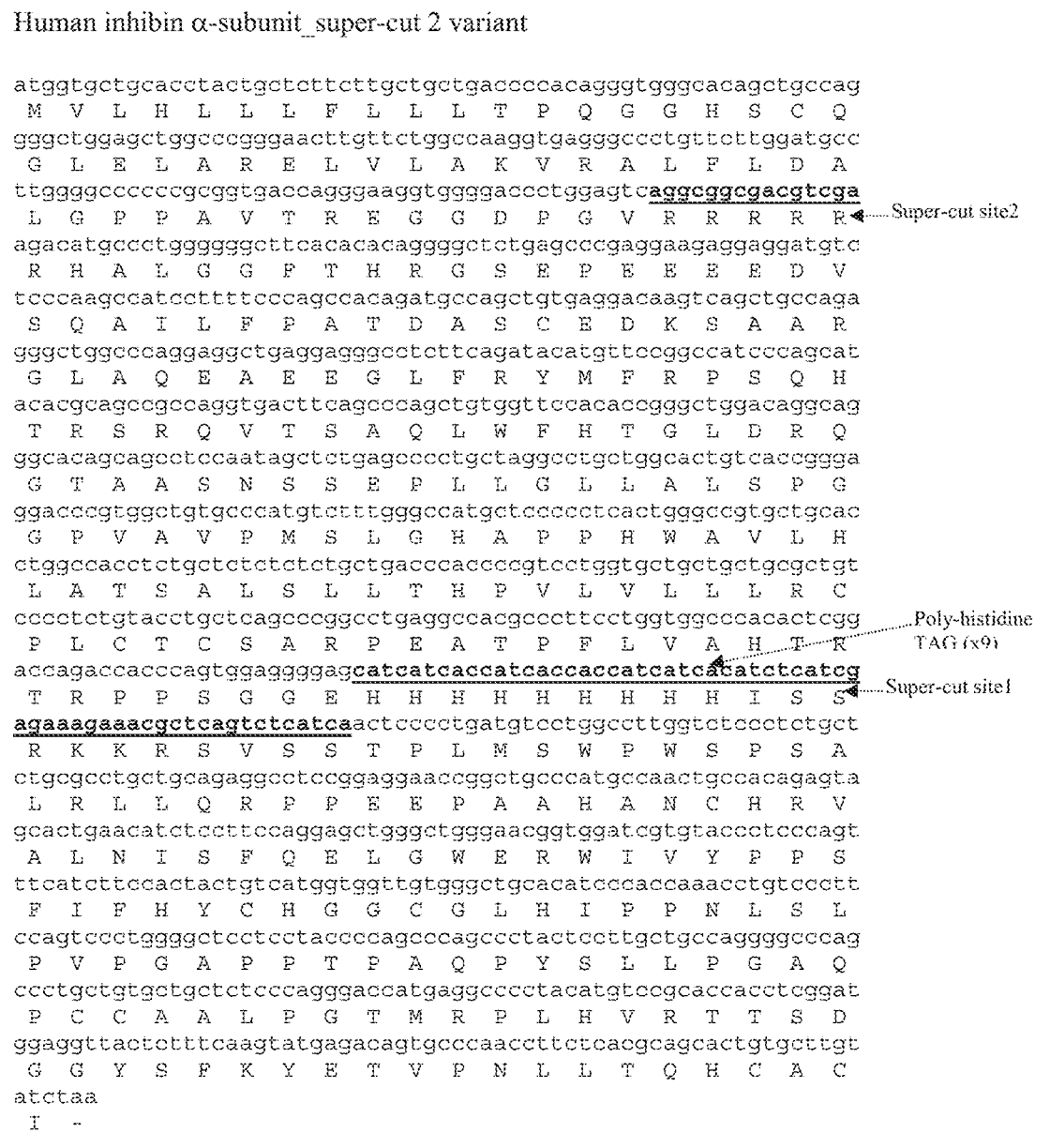

Human inhibin α-subunit_super-cut 2 variant

```
atggtgctgcacctactgctcttcttgctgctgaccccacagggtgggcacagctgccag
 M  V  L  H  L  L  F  L  L  L  T  P  Q  G  G  H  S  C  Q
gggctggagctggcccgggaacttgttctggccaaggtgagggccctgttcttggatgcc
 G  L  E  L  A  R  E  L  V  L  A  K  V  R  A  L  F  L  D  A
ttggggccccccgcggtgaccagggaaggtggggaccctggagtcaggcggcgacgtcga ←— Super-cut site2
 L  G  P  P  A  V  T  R  E  G  G  D  P  G  V  R  R  R  R
agacatgccctggggggcttcacacac INHBB_super-cut_M410A SEQ (Wt INHBB SEQ)

```
atggacgggctgcccggtcggcgctggggccgcctgccttctgctgctggcggccggc
 M  D  G  L  P  G  R  A  L  G  A  A  C  L  L  L  A  A  G
tggctggggcctgaggcctggggcgactacaaagacgacgacgacaagatcacccacgccc          FLAG Tag
 W  L  G  P  E  A  W  G  D  Y  K  D  D  D  D  K  S  P  T  P
ccgccgacgcctgccgcgccgccgccacccccgccacccggatccccggggtggctcgcag
 P  P  T  P  A  A  P  P  P  P  P  P  P  G  S  P  G  S  Q
gacacctgtacgtcgtgcggcggcttccggcggccagaggagctcggccgagtggacggc
 D  T  C  T  S  C  G  G  F  R  R  P  E  E  L  G  R  V  D  G
gacttcctggaggcggtgaagcggcacatcttgagccgcctgcagatgcggggccggccc
 D  F  L  E  A  V  K  R  H  I  L  S  R  L  Q  M  R  G  R  P
aacatcacgcacgccgtgcctaaggccgccatggtcacggccctgcgcaagctgcacgcg
 N  I  T  H  A  V  P  K  A  A  M  V  T  A  L  R  K  L  H  A
ggcaaggtgcgcgaggacggccgcgtggagatccgcacctcgacggccacgccagcccg
 G  K  V  R  E  D  G  R  V  E  I  P  H  L  D  G  H  A  S  P
ggcgccgacggccaggagcgcgtttccgaaatcatcagcttcgccgagacagatggcctc
 G  A  D  G  Q  E  R  V  S  E  I  I  S  F  A  E  T  D  G  L
gcctcctcccgggtccgcctatacttcttcatctccaacgaaggcaaccagaacctgttt
 A  S  S  R  V  R  L  Y  F  F  I  S  N  E  G  N  Q  N  L  F
gtggtccaggccagcctgtggctttacctgaaactcctgccctacgtcctggagaagggc
 V  V  Q  A  S  L  W  L  Y  L  K  L  L  P  Y  V  L  E  K  G
agccggcggaaggtgcgggtcaaagtgtacttccaggagcagggccacggtgacaggtgg
 S  R  R  K  V  R  V  K  V  Y  F  Q  E  Q  G  H  G  D  R  W
aacatggtggagaagagggtggacctcaagcgcagcggctggcataccttcccactcacg
 N  M  V  E  K  R  V  D  L  K  R  S  G  W  H  T  F  P  L  T
gaggccatccaggccttgtttgagcggggcgagcggcgactcaacctagacgtgcagtgt
 E  A  I  Q  A  L  F  E  R  G  E  R  R  L  N  L  D  V  Q  C
gacagctgccaggagctggccgtggtgccggtgttcgtggacccaggcgaagagtcgcac
 D  S  C  Q  E  L  A  V  V  P  V  F  V  D  P  G  E  E  S  H
cggcccttgtggtggtgcaggctcggctgggcgacatctcatcgagaaagaaacgctca          Super-cut
 R  P  F  V  V  V  Q  A  R  L  G  D  I  S  S  R  K  K  R  S
gtctcatcgggcctggagtgcgatggccggaccaacctctgttgcaggcaacagttcttc
 V  S  S  G  L  E  C  D  G  R  T  N  L  C  C  R  Q  Q  F  F
attgacttccgcctcatcggctggaacgactggatcatagcacccaccggctactacggg
 I  D  F  R  L  I  G  W  N  D  W  I  I  A  P  T  G  Y  Y  G
aactactgtgagggcagctgcccagcctacctggcaggggtccccggctctgcctcctcc
 N  Y  C  E  G  S  C  P  A  Y  L  A  G  V  P  G  S  A  S  S
ttccacacggctgtggtgaaccagtaccgcatgcggggtctgaaccccggcacggtgaac
 F  H  T  A  V  V  N  Q  Y  R  M  R  G  L  N  P  G  T  V  N
tcctgctgcattcccaccaagctgagcaccatgtccatgctgtacttcgatgatgagtac
 S  C  C  I  P  T  K  L  S  T  M  S  M  L  Y  F  D  D  E  Y
aacatcgtcaagcgggacgtgcccaacgcgattgtggaggagtgcggctgcgcctga
 N  I  V  K  R  D  V  P  N  A  I  V  E  E  C  G  C  A  -
                                   M410A mutation
```

Figure 10

```
INHBB_super-cut_M410A SEQ atggatggacttccaggtcgagctctggggccgcctgccttctgctgctggcggccggc
 M  D  G  L  P  G  R  A  L  G  A  A  C  L  L  L  L  A  A  G
tggctggggcctgaggcctggggcgactacaaagacgacgacgacaaatcacccacgccc ......FLAG tag
 W  L  G  P  E  A  W  G  D  Y  K  D  D  D  D  K  S  P  T  P
ccgccgacgcctgccgcgccgccgccaccccgccaccggatccccgggtggctcgcag
 P  P  T  P  A  A  P  P  P  P  P  P  G  S  P  G  G  S  Q
gacacctgtacgtcgtgcggcggcttccggcggccagaggagctcggccgagtggacggc
 D  T  C  T  S  G  G  F  R  R  P  E  E  L  G  R  V  D  G
gacttcctggaggcggtgaagcggcacatcttgagccgcctgcagatgcggggccggccc
 D  F  L  E  A  V  K  R  H  I  L  S  R  L  Q  M  R  G  R  P
aacatcacgcacgccgtgcctaaggccgccatggtcacggccctgcgcaagctgcacgcg
 N  I  T  H  A  V  P  K  A  A  M  V  T  A  L  R  K  L  H  A
ggcaaggtgcgcgaggacggccgcgtggagatcccgcacctcgacggccacgccagcccg
 G  K  V  R  E  D  G  R  V  E  I  P  H  L  D  G  H  A  S  P
ggcgccgacggccaggagcgcgtttccgaaatcatcagcttcgccgagacagatggcctc
 G  A  D  G  Q  E  R  V  S  E  I  I  S  F  A  E  T  D  G  L
gcctcctcccgggtccgcctatacttcttcatctccaacgaaggcaaccagaacctgttt
 A  S  S  R  V  R  L  Y  F  F  I  S  N  E  G  N  Q  N  L  F
gtggtccaggccagcctgtggctttacctgaaactcctgccctacgtcctggagaagggc
 V  V  Q  A  S  L  W  L  Y  L  K  L  L  P  Y  V  L  E  K  G
agccggcggaaggtgcgggtcaaagtgtacttccaggagcagggccacggtgacaggtgg
 S  R  R  K  V  R  V  K  V  Y  F  Q  E  Q  G  H  G  D  R  W
aacatggtggagaagagggtggacctcaagcgcagcggctggcataccttcccactcacg
 N  M  V  E  K  R  V  D  L  K  R  S  G  W  H  T  F  P  L  T
gaggccatccaggccttgtttgagcggggcgagcggcgactcaacctagacgtgcagtgt
 E  A  I  Q  A  L  F  E  R  G  E  R  R  L  N  L  D  V  Q  C
gacagctgccaggagctggccgtggtgccggtgttcgtggacccaggcgaagagtcgcac
 D  S  C  Q  E  L  A  V  V  P  V  F  V  D  P  G  E  E  S  H
cggccctttgtggtggtgcaggctcggctgggcgacatctcatcgagaaagaaacgctca ......Super-cut site
 R  P  F  V  V  V  Q  A  R  L  G  D  I  S  S  R  K  K  R  S
gtctcatcgggcctggagtgcgatggccggaccaacctctgttgcaggcaacagttcttc
 V  S  S  G  L  E  C  D  G  R  T  N  L  C  C  R  Q  Q  F  F
attgacttccgcctcatcggctggaacgactggatcatagcacccaccggctactacggg
 I  D  F  R  L  I  G  W  N  D  W  I  I  A  P  T  G  Y  Y  G
aactactgtgagggcagctgcccagcctacctggcaggggtccccggctctgcctcctcc
 N  Y  C  E  G  S  C  P  A  Y  L  A  G  V  P  G  S  A  S  S
ttccacacggctgtggtgaaccagtaccgcatgcggggtctgaacccggcacggtgaac
 F  H  T  A  V  V  N  Q  Y  R  M  R  G  L  N  P  G  T  V  N
tcctgctgcattccaccaagctgagcaccatgtccatgctgtacttcgatgatgagtac
 S  C  C  I  P  T  K  L  S  T  M  S  M  L  Y  F  D  D  E  Y
aacatcgtcaagcgggacgtgcccaacgcgattgtggaggagtgcggctgcgcctga
 N  I  V  K  R  D  V  P  N  A  I  V  E  E  C  G  C  A  -
                              ▲......M410A mutation
```

Figure 14

INHIBIN ANALOGS

CROSS-REFERENCE TO RELATED APPLICATIONS

The present application is a U.S. National Stage of International Patent Application No. PCT/AU2016/051156, filed on Nov. 25, 2016, which claims priority to Australian Provisional Patent Application No. 2015904898, filed on Nov. 26, 2015, both disclosures of which are incorporated are incorporated by reference, in their entirety. This specification refers to a Sequence Listing. The "ST25.txt" file is in ANSI format. The file is hereby incorporated in its entirety by reference from AU 2015904898 into the subject specification.

FIELD

The present invention relates to inhibin analogs, their method of production and their use in the treatment and prophylaxis of disease or conditions associated with reduced levels of inhibin and activin-mediated signaling.

BACKGROUND

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Follicle stimulating hormone (FSH) regulates spermatogenesis in males and folliculogenesis in females. In response to FSH, testicular Sertoli cells and ovarian granulosa cells produce inhibin A and/or inhibin B, which target the gonadotrope cells of the pituitary to down-regulate the production and secretion of FSH in a cycle-dependent manner in females and in a tonic pattern in males (Woodruff et al. (1996) $Endocrinology$ 137:5463-5467). Circulating inhibin levels decrease dramatically across the menopause transition and inversely correlate with increased serum FSH (Robertson et al. (2008) $Menopause$ 15:1139-1144).

Inhibin A and B are unique members of the transforming growth factor-$\beta$ (TGF-$\beta$) superfamily as they: (i) are heterodimers composed of $\alpha$- and $\beta$ ($\beta_A$ or $\beta_B$)-subunits, whereas most other family members are homodimers; (ii) act as antagonists, rather than agonists, inhibiting signaling of activin-related proteins; and (iii) function in an endocrine rather than autocrine/paracrine manner. These aspects of inhibin biology are crucial for their roles in reproduction, but they also endow these hormones with the potential to regulate additional physiological processes, including bone and muscle growth.

Analogous to other members of the TGF-$\beta$ superfamily, inhibin $\alpha$- and $\beta$-subunits are synthesized as large precursor molecules with the N-terminal prodomain mediating the folding and dimerization of the C-terminal mature domains (Walton et al. (2009) $J Biol Chem.$ 284:9311-9320). Dimeric precursors are cleaved by proprotein convertases and inhibins are secreted from Sertoli and granulosa cells non-covalently associated with their prodomain (pro-mature complexes). Once localized to target tissues, prodomains are displaced, and mature 31 kDa inhibins associate with their cognate receptors.

It is recognized that inhibin A and B regulate FSH secretion from the anterior pituitary by blocking the stimulatory actions of activins (Wiater and Vale (2003) $J Biol Chem.$ 278:7934-7941). Activins are homodimers of inhibin $\beta$-subunits: $\beta_A$-$\beta_A$ (activin A), $\beta_B$-$\beta_B$ (activin B). Activins initially bind to type II receptors, ActRIIA or ActRIIB, leading to recruitment, phosphorylation and activation of the type I receptor, ALK4. Activated ALK4 phosphorylates intracellular signaling molecules, Smad2/3, which in turn form a complex with the co-activator, Smad4. The resulting Smad oligomer localizes within the nucleus to regulate target genes (e.g. Fshb) in a cell- and context-dependent manner (Massague and Wotton $EMBO J.$ 19:1745-1754). Inhibin antagonism of activin-related ligands is dependent upon interactions with betaglycan, a cell-surface proteoglycan that also acts as a TGF-$\beta$ co-receptor (Lewis et al. (2000) $Nature$ 404:411-414). Betaglycan binds inhibin A and B directly and promotes the formation of a stable high affinity complex involving activin type II receptors (Lewis et al. (2000) supra). Sequestration of type II receptors in this way prevents their interactions with signaling ligands such as activins. In the absence of betaglycan, inhibin cannot block activin-mediated FSH secretion by pituitary gonadotrope cells (Wiater et al. (2009) $Mot Endocrinol.$ 23:1033-1042).

Aspects of inhibins' mode of action, including the widespread expression of inhibin receptors and the fact that activins target multiple tissues, presuppose functions beyond the negative regulation of FSH. Indeed, serum inhibin A and B levels correlate inversely with markers of bone formation and bone resorption in women across the menopause transition, and it has been proposed that these decreases in inhibin contribute to the initial bone loss during this period (Perrien et al. (2006) $J Clin Endocrinol Metab.$ 91:1848-1854). To test whether inhibin A could regulate bone mass in vivo, (Perrien et al. (2007) $Endorcinology$ 148:1654-1665; Perrien et al. (2012) $J Orthopaed Res.$ 30:288-295) utilized a transgenic model of inducible human inhibin A expression. Inhibin A increased total body bone mineral density (BMD), increased bone volume and improved biomechanical properties at the proximal tibia of intact mice, and also prevented the loss of BMD and bone volume associated with gonadectomy. As activin A, one of the most highly expressed TGF-$\beta$ proteins in bone, potently suppresses osteoblast differentiation (Lotinun et al. (2012) $Curr Mol Pharmacol.$ 5:195-204), it is likely that inhibins' anabolic effect is via inhibition of this growth factor. Thus, gonadal inhibins are likely components of the normal endocrine repertoire that regulate bone quality, and the loss of inhibins at menopause may play a significant role in osteoporosis progression.

Definitively characterizing the physiological roles of inhibin A and B, however, has proven difficult for several reasons. First, targeted deletion of the inhibin $\alpha$-subunit in mice leads to unopposed gonadal expression of activin A and B. As activins stimulate granulosa and Sertoli cell proliferation, inhibin-deficient mice develop sex-cord stromal tumors with 100% penetrance, as early as 4 weeks of age (Matzuk et al. (1992) $Nature$ 360:313-319). As tumors progress, serum levels of activin A and B increase up to 500-fold (Li et al. (2007) $Mol Human Reprod.$ 13:675-683), and mice die from a cachexia-like wasting syndrome between 12-17 weeks (Matzuk et al. (1994) $Proc Natl Acad Sci USA$ 91:8817-8821). Thus, the phenotype of the inhibin $\alpha$-subunit knockout mouse does not really reflect the loss of inhibin, but rather the devastating systemic effects of elevated circulating activins. Secondly, in vivo overexpression of inhibins (α/β-subunit heterodimers) is always accompanied by production of activins (β-subunit homodimers), which have pleiotropic effects in multiple organs (Harrison et al. (2005) *Trends Endocrinol Metab.* 16:73-78). Finally, recombinant production of inhibins and their separation from contaminating activins is difficult, and the resultant 31 kDa mature inhibin isoforms have short in vivo half-lives (Makanji et al. (2009) *Endocrinology* 150:4784-4793).

There is a need to develop an improved system to generate inhibin A and inhibin B for therapeutic use.

SUMMARY

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims. Abbreviations used herein are listed in Table 2.

The present specification teaches a mammalian inhibin analog precursor protein comprising a heterodimer of α-subunit and β-subunit precursors each having at least one proprotein convertase cleavage site wherein at least one proprotein convertase cleavage site in the α-subunit and/or β-subunit is modified by an amino acid substitution mutation to render it more efficiently cleaved by the proprotein convertase. This enables the efficient generation of an inhibin in bioactive form. The term "analog" is used to highlight that the inhibin precursor protein contains an artificially introduced mutation to facilitate more efficient processing. Other terms such as "variant", "mutant" and "modified protein" may also be used to the same effect. The bioactive inhibin and its precursor are useful in the treatment of a range of diseases and conditions such as arising from reduced production of an inhibin or where antagonism of an activin would ameliorate a particular disease or condition. Reduced serum levels of inhibin in post-menopausal women, for example, can exacerbate bone disorders such as osteoporosis.

In an embodiment, a "primary" proprotein convertase cleavage site in each of the α-subunit and β-subunit precursors is modified by the amino acid substitution mutation. In a further embodiment, the α-subunit protein comprises a secondary proprotein convertase cleavage site, which is modified by an amino acid substitution mutation to render it more efficiently cleaved by the proprotein convertase. In an embodiment, the modified proprotein primary convertase site is defined by the amino acid sequence set forth in SEQ ID NO:18 (ISSRKKRSVSS). The β-subunits may be $\beta_A$-subunit leading to an inhibin A analog or a $\beta_B$-subunit leading to an inhibin B analog when either subunit forms a heterodimer with the α-subunit. The α- and/or β-subunits may contain additional amino acid substitutions, additions and/or deletions with the proviso that either or both subunits contain a modified proprotein convertase cleavage site(s) to render convertase processing more efficient compared to cleavage of a wild-type α- and/or β-subunit. An example of another amino acid modification is at the predicted β/β homodimerization interface, required for the formation of an activin. These sites include A347, Y345, F326, V392, P393 and L396 in $\beta_A$-subunit (using the wild-type amino acid sequence in SEQ ID NO:2). Sites in $\beta_B$-subunit include F308, Y327, G329, I373, P374 and L377 (using the wild-type amino acid sequence in SEQ ID NO:12). Homodimers of β subunits are present in activins ($\beta_A+\beta_A$ in activin A or $\beta_B+\beta_B$ for activin B). A homodimerization interface mutation reduces the ability for homodimers (i.e. activins) to form. The variants of the present invention retain inhibin activity, are generated with improved processing efficiency resulting in higher proportion of active inhibin, exhibit enhanced α/β dimerization and have reduced or silenced activin receptor binding activity. This is especially the case when there is a further mutation such as a mutation at a homodimerization interface site on $\beta_A$ or $\beta_B$ to prevent or reduce homodimerization formation.

The inhibin analog precursor protein may be of human or non-human mammalian origin. Hence, the precursor protein or the inhibin generated therefrom has therapeutic potential in humans and non-human mammals.

The β-subunit of the inhibin analog precursor protein may further comprise a single mutation within a type I receptor (ALK4) binding epitope of the mature domain leading to inactive activin. Activin is generally co-formed during the synthesis of inhibins and comprises β-subunit homodimers. The mutation in the β-subunit renders inactive any activin formed. A mutation at a homodimerization interface site further facilitates an absence of or reduce amount of active activin.

For the human $\beta_A$-subunit, the mutation includes a M418A (based on numbering in SEQ ID NO:2; equivalent to M432A in SEQ ID NO:4) substitution mutation (numbering from start of prodomain; equivalent to M108A from start of the mature domain). This means the resident methionine residue is replaced by an alanine residue. For the human $\beta_B$-subunit, the mutation includes a M399A substitution mutation (from start of prodomain); numbering from SEQ ID NO:12; equivalent to M410A in SEQ ID NO:14.

Additional mutation(s) may also be added at the interface site for homodimerization to occur for $\beta_A+\beta_A$ dimerization into activin A and $\beta_B+\beta_B$ dimerization into activin B. Such mutations reduce or inhibit altogether functional activin molecules being produced. Examples include $A347X_1$, $Y345X_2$, $F326X_3$, $V392X_4$, $P393X_5$ and $L396X_6$ wherein each of $X_1$, $X_2$, $X_3$, $X_4$, $X_5$ and $X_6$ is any amino acid except A, Y, F, V, P and L, respectively (based on numbering in SEQ ID NO:2) in subunit $\beta_A$; and $F308X_7$, $Y327X_8$, $G329X_9$, $I373X_{10}$, $P374X_{11}$ and $L377X_{12}$ wherein each of $X_7$, $X_8$, $X_9$, $X_{10}$, $X_{11}$ and $X_{12}$ is any amino acid except F, Y, G, I, P and L, respectively (using numbering in SEQ ID NO:12). Particular examples including A347H, Y345G and A347H+Y345G in $\beta_A$-subunit.

The inhibin analog precursor protein $\beta_A$- or $\beta_B$-subunit may further comprise a FLAG tag comprising the amino acid sequence DYKDDDK (SEQ ID NO:16) between amino acids 27 and 28 of $\beta_A$ or 28 and 29 of $\beta_B$. The α-subunit may comprise a poly-histidine tag. These aid in purification of inhibin from conditioned medium by affinity chromatography as well as distinguishing wild-type protein from modified protein.

The modified proprotein convertase sites improve the efficiency of cleavage of the inhibin analog precursor protein relative to enzymatic cleavage of the wild-type protein. In addition, there is a concomitant reduction in bioactive activin. This is further enhanced by the introduction of the mutation in the ALK4 binding epitope in the β-subunit mature domain and/or mutation at a site required for homodimerization of a $\beta_A$-subunit on $\beta_B$-subunit.

Hence, enabled herein is an inhibin α-subunit precursor comprising:

a modified primary proprotein convertase site ("super-cut site1");

(ii) a modified secondary proprotein convertase site ("super-cut site2");

(iii) modified primary and secondary proprotein convertase sites; and optionally together with a poly-histidine tag to assist with purification.

Further enabled herein is an inhibin $\beta_A$-subunit precursor comprising a modified proprotein convertase site ("super-cut site");

optionally with a mutation disrupting the ALK4 binding epitope in the mature domain and optionally with a FLAG tag to assist in affinity chromatography purification and optionally with a mutation disrupting homodimerization.

Taught herein is an inhibin $\beta_B$-subunit precursor comprising a modified proprotein convertase site ("super-cut site");

optionally with a mutation disrupting the ALK4 binding epitope in the mature domain and optionally with a FLAG tag to assist in affinity chromatography purification and optionally with a mutation disrupting homodimerization.

Hence, in an embodiment an inhibin analog precursor protein is provided comprising an α-subunit having the amino acid sequence as set forth in SEQ ID NO:8 (α-subunit super-cut site1+poly-his) or an amino acid sequence having at least 80% sequence similarity to SEQ ID NO:8 after optimal alignment with the proviso that it comprises at least one modified proprotein convertase site to enable more efficient cleavage by the convertase.

Enabled herein is an inhibin analog precursor protein comprising an α-subunit having the amino acid sequence as set forth in SEQ ID NO:10 (α-subunit super-cut sites1 and 2+poly-his) or an amino acid sequence having at least 80% sequence similarity to SEQ ID NO:10 after optimal alignment with the proviso that it comprises at least one modified proprotein convertase site to enable more efficient cleavage by the convertase.

In an embodiment, an inhibin analog precursor protein is provided comprising an $\beta_A$-subunit having the amino acid sequence as set forth in SEQ ID NO:4 ($\beta_A$-subunit super-cut+ALK4 mutation+FLAG tag) or an amino acid sequence having at least 80% sequence similarity to SEQ ID NO:4 after optimal alignment with the proviso that it comprises at least one modified proprotein convertase site to enable more efficient cleavage by the convertase.

Taught herein is an inhibin analog precursor protein comprising an $\beta_A$-subunit having the amino acid sequence as set forth in SEQ ID NO:40 ($\beta_A$-subunit super-cut+ALK4 mutation+FLAG tag+interface mutation) or an amino acid sequence having at least 80% sequence similarity to SEQ ID NO:40 after optimal alignment with the proviso that it comprises at least one modified proprotein convertase site to enable more efficient cleavage by the convertase.

Enabled herein is an inhibin analog precursor protein comprising an $\beta_A$-subunit having the amino acid sequence as set forth in SEQ ID NO:41 ($\beta_A$-subunit super-cut+ALK4 mutation+FLAG tag+interface mutation) or an amino acid sequence having at least 80% sequence similarity to SEQ ID NO:41 after optimal alignment with the proviso that it comprises at least one modified proprotein convertase site to enable more efficient cleavage by the convertase.

In an embodiment, an inhibin analog precursor protein is provided comprising an $\beta_A$-subunit having the amino acid sequence as set forth in SEQ ID NO:42 ($\beta_A$-subunit super-cut+ALK4 mutation+FLAG tap+combined interface mutations) or an amino acid sequence having at least 80% sequence similarity to SEQ ID NO:42 after optimal alignment with the proviso that it comprises at least one modified proprotein convertase site to enable more efficient cleavage by the convertase.

Taught herein is an inhibin analog precursor protein comprising an $\beta_B$-subunit having the amino acid sequence as set forth in SEQ ID NO:14 ($\beta_B$-subunit super-cut+ALK4 mutation+FLAG tag) or an amino acid sequence having at least 80% sequence similarity to SEQ ID NO:14 after optimal alignment with the proviso that it comprises at least one modified proprotein convertase site to enable more efficient cleavage by the convertase.

Further enabled herein is a nucleic acid molecule encoding the α-subunit or $\beta_A$-subunit or $\beta_B$-subunit precursor. The nucleic acid may be operably linked to a promoter and if necessary a terminator sequence or other regulatory sequence. The nucleic acid molecule is used to transfect cells or cell lines to coproduce α- and either $\beta_A$- or $\beta_B$-subunits.

In an embodiment, the nucleic acid molecule encoding the α-subunit variant comprises the nucleotide sequence set forth in SEQ ID NO:7 (super-cut site1+poly-his) or a nucleotide sequence having at least about 80% identity thereto after optimal alignment or a nucleic acid capable of hybridizing to the complement of SEQ ID NO:7 under stringency conditions.

In another embodiment, the nucleic acid molecule encoding the α-subunit variant comprises the nucleotide sequence set forth in SEQ ID NO:9 (super-cut sites1 and 2+poly-his) or a nucleotide sequence having at least about 80% identity thereto after optimal alignment or a nucleic acid capable of hybridizing to the complement of SEQ ID NO:9 under stringency conditions.

A nucleic acid molecule encoding the $\beta_A$-subunit includes the nucleotide sequence as set forth in SEQ ID NO:3 (super-cut site+ALK4 mutation+FLAG tag) or a nucleotide sequence having at least about 80% identity thereto after optimal alignment or a nucleic acid capable of hybridizing to the complement of SEQ ID NO:3 under stringency conditions.

A nucleic acid molecule encoding the $\beta_B$-subunit includes the nucleotide sequence as set forth in SEQ ID NO:13 (super-cut site+ALK4 mutation+FLAG tag) or a nucleotide sequence having at least about 80% identity thereto after optimal alignment or a nucleic acid capable of hybridizing to the complement of SEQ ID NO:13 under stringency conditions.

Further enabled herein is an isolated cell or cell line comprising the nucleic acid encoding the α-subunit and either the $\beta_A$-subunit or $\beta_B$-subunit variant.

The above nucleic acid molecules may encode a range of amino acid substitutions, additions and/or deletions provided that they encode a modified proprotein convertase cleavage site which is more efficiently cleaved by the convertase compared to a wild-type α- and/or β-subunit. A cell or cell line transfected with a nucleic acid encoding the α-subunit and β-subunit precursors and cultured in a growth medium generates bioactive inhibin following expression of the nucleic acid to produce inhibin precursor and proprotein convertase cleavage of the inhibin analog precursor protein. Inhibin production is enhanced by modulating the ratio of nucleic acids encoding the α- and β-subunits. Generally, the ratio is α>β, such as but not limited to 3:2, respectively.

In an embodiment, an equal amount of α-subunit encoding nucleic acid and β-subunit encoding are transfected into the cell or cell line. In another embodiment, the ratio of α-subunit to β-subunit encoding nucleic acid is α>β including the ratio 3:2 (α:β, respectively). In another embodiment, the ratio is α<β including 2:3 (α:β, respectively).

A method for generating a bioactive inhibin analog is contemplated herein the method comprising co-expressing in a cell or cell line nucleic acid encoding the α-subunit and a $\beta_A$-subunit or $\beta_B$-subunit as defined herein for a time and under conditions sufficient for an inhibin precursor protein to be produced, cleaved by a proprotein convertase and secreted from the cell or cell line as a bioactive inhibin analog.

This leads to the generation of inhibin A analog or inhibin B analog.

In an embodiment, minimal bioactive activin A or activin B is produced.

Further contemplated herein is a method of treatment of a mammalian subject comprising the administration of an inhibin A or inhibin B analog as defined herein or an inhibin analog precursor protein thereof.

In an embodiment, the mammal is a human.

Taught herein is a pharmaceutical composition comprising an inhibin A or inhibin B analog as defined herein or an inhibin analog precursor protein thereof and one or more pharmaceutically acceptable carriers, diluents and/or excipients.

Further taught herein is the use of an inhibin A or inhibin B analog as defined herein or an inhibin analog precursor protein thereof in the manufacture of a medicament for the treatment of a mammalian subject in need of therapy. In a related embodiment enabled herein is an inhibin A or inhibin B analog as defined herein or an inhibin analog precursor protein thereof for use in the treatment of a mammalian subject in need of therapy. In an embodiment, the mammal is a human.

In a further embodiment, the subject has reduced serum levels of inhibin compared to the level in a pre-menopausal healthy subject or has a disease or condition exacerbated by activin-mediated signaling.

Additional embodiment described herein includes antibodies to the inhibin analogs or their precursors.

The location of homodimerization interface sites which can or have been mutated are shown in Table 3 ($\beta_A$-subunit) and Table 4 ($\beta_B$-subunit).

TABLE 1

Summary of sequence identifiers

| SEQUENCE ID NO: | DESCRIPTION |
|---|---|
| 1 | Nucleotide sequence encoding wild-type human inhibin $\beta_A$-subunit |
| 2 | Amino acid sequence of wild-type human inhibin $\beta_A$-subunit |
| 3 | Nucleotide sequence encoding super-cut variant of human inhibin $\beta_A$-subunit (super-cut site + ALK4 mutation + FLAG tag) |
| 4 | Amino acid sequence of super-cut variant of inhibin $\beta_A$-subunit (super-cut site + ALK4 mutation + FLAG tag) |
| 5 | Nucleotide sequence encoding wild-type human inhibin α-subunit |
| 6 | Amino acid sequence of wild-type human inhibin α-subunit |
| 7 | Nucleotide sequence encoding super-cut variant 1 of human inhibin α-subunit (super-cut site1 + poly-his) |
| 8 | Amino acid sequence of super-cut variant 1 of human inhibin α-subunit (super-cut site 1 + poly-his) |
| 9 | Nucleotide sequence encoding super-cut variant 2 of human inhibin α-subunit (super-cut sites 1 and 2 + poly-his) |
| 10 | Amino acid sequence of super-cut variant 2 of human inhibin α-subunit (super-cut sites 1 and 2 + poly-his) |
| 11 | Nucleotide sequence encoding wild-type human inhibin $\beta_B$-subunit |
| 12 | Amino acid sequence of wild-type human inhibin $\beta_B$-subunit |
| 13 | Nucleotide sequence encoding super-cut variant of human inhibin $\beta_B$-subunit (super-cut + ALK4 mutation + FLAG tag) |
| 14 | Amino acid sequence of super-cut variant of human inhibin $\beta_B$-subunit (super-cut + ALK4 mutation + FLAG tag) |
| 15 | Nucleotide sequence encoding FLAG tag |
| 16 | Amino acid sequence of FLAG tag |
| 17 | Nucleotide sequence encoding super-cut site1 |
| 18 | Amino acid sequence of super-cut site1 |
| 19 | Nucleotide sequence encoding poly-histidine TAG (x9) |
| 20 | Amino acid sequence of poly-histidine TAG (x9) |
| 21 | Nucleotide sequence encoding super-cut site 2 |
| 22 | Amino acid sequence of super-cut site 2 |
| 23 | Nucleotide sequence of α-NHE1 sense primer |
| 24 | Nucleotide sequence of α-ECOR1 antisense primer |
| 25 | Nucleotide sequence of α-SCUT (site1) sense primer |
| 26 | Nucleotide sequence of α-SCUT (site1) antisense primer |
| 27 | Nucleotide sequence of α-SCUT (site2) sense primer |
| 28 | Nucleotide sequence of α-SCUT (site2) antisense primer |
| 29 | Nucleotide sequence of α-polyH1 Stag sense primer |
| 30 | Nucleotide sequence of α-polyH1 Stage antisense primer |
| 31 | Nucleotide sequence of βAXBA1 sense primer |
| 32 | Nucleotide sequence of βA-NOT1 antisense primer |
| 33 | Nucleotide sequence of βA-SCUT (site1) sense primer |
| 34 | Nucleotide sequence of βA-SCUT (site1) antisense primer |
| 35 | Nucleotide sequence of βA-M418A sense primer |

TABLE 1-continued

Summary of sequence identifiers

| SEQUENCE ID NO: | DESCRIPTION |
|---|---|
| 36 | Nucleotide sequence of βA-M418A antisense primer |
| 37 | Amino acid sequence of human $\beta_A$-subunit variant with A347H substitution at interface region for homodimerization. |
| 38 | Amino acid sequence of human $\beta_A$-subunit variant with Y345G substitution at interface region for homodimerization. |
| 39 | Amino acid sequence of human $\beta_A$-subunit variant with A347H/Y345G double mutation at interface region for homodimerization. |
| 40 | Amino acid sequence of human-$\beta_A$-subunit with super-cut + ALK4 mutation FLAG tag + A347H (=A361H) mutation. |
| 41 | Amino acid sequence of human-$\beta_A$-subunit with super-cut + ALK4 mutation FLAG tag + Y345G (=Y359G) mutation. |
| 42 | Amino acid sequence of human-$\beta_A$-subunit with super-cut + ALK4 mutation FLAG tag + A347H + Y345G (=A361H + Y359G) mutations. |
| 43 | Nucleotide sequence encoding super-cut variant of human inhibin $\beta_B$-subunit (super-cut + ALK4 mutation + FLAG tag): with a modified signal sequence |
| 44 | Amino acid sequence of super-cut variant of human inhibin $\beta_B$-subunit (super-cut + ALK4 mutation + FLAG tag): with a modified signal sequence |

TABLE 2

Abbreviations

| ABBREVIATION | DESCRIPTION |
|---|---|
| ALK4 | Type I receptor activated via an activin |
| BMD | Bone mineral density |
| E4 | Inhibin $\beta_A$-subunit monoclonal antibody |
| FCS | Fetal calf serum |
| FSH | Follicle stimulating hormone |
| Interface mutation | Mutation at a site on $\beta_A$ or $\beta_B$ which prevents or reduces homodimerization. Also referred to as "dimerization interface mutation" and a "homodimerization interface mutation" |
| LβT2 | Mouse pituitary gonadotrope cell line |
| PBS | Phosphate buffered saline |
| R1 | Inhibin α-subunit monoclonal antibody |
| Super-cut site (α- or β-SCUT) | Proprotein convertase cleavage site in α- and β-subunits of an inhibin |
| Super-cut site1 (α-SCUT1) | Primary proprotein convertase site in α-subunit of inhibin |
| Super-cut site2 (α-SCUT2) | Secondary proprotein convertase site in α-subunit of inhibin |
| TGFβ | Transforming growth factor-β |
| α | α-subunit of inhibin |
| α-$\beta_A$ | Inhibin A heterodimer |
| α-$\beta_B$ | Inhibin B heterodimer |
| $\beta_A$ | $\beta_A$-subunit of inhibin |
| $\beta_A$-$\beta_A$ | Activin A homodimer |
| $\beta_B$ | $\beta_B$-subunit of inhibin |
| $\beta_B$-$\beta_B$ | Activin B homodimer |

TABLE 3

Homodimerization interface sites on $\beta_A$-subunit

| Wild-type $\beta_A$-subunit (SEQ ID NO: 2) | Variant $\beta_A$-subunit (super-cut site + ALK4 mutation + FLAG tag) (SEQ ID NO: 4) | Variant $\beta_A$-subunit (super-cut site + ALK4 mutation + FLAG tag + interface mutation (SEQ ID NO: 40) | Variant $\beta_A$-subunit (supercut site + ALK4 mutation + FLAG tag + interface mutation (SEQ ID NO: 41) | Variant $\beta_A$-subunit (supercut site + ALK4 mutation + FLAG tag + interface mutation (SEQ ID NO: 42) |
|---|---|---|---|---|
| A347 | A361 | A361H | A361 | A361H |
| Y345 | Y359 | Y359 | Y359G | Y359G |
| F326 | F340 | F340 | F340 | F340 |
| V392 | V406 | V406 | V406 | V406 |
| P393 | P407 | P407 | P407 | P407 |
| L396 | L410 | L410 | L410 | L410 |

TABLE 4

Homodimerization interface sites on $\beta_B$-subunit

| Wild-type $\beta_B$-subunit (SEQ ID NO: 12) | Variant $\beta_B$-subunit (super-cut site + ALK4 mutation + FLAG tag) (SEQ ID NO: 14)[1] |
|---|---|
| F308 | F319 |
| Y327 | Y338 |
| G329 | G340 |
| I373 | I384 |
| P374 | P385 |
| L377 | L388 |

[1]This sequence has a Ser Arg His deleted as part of the supercut modification (compared to the wild-type sequence).

Figure 1:
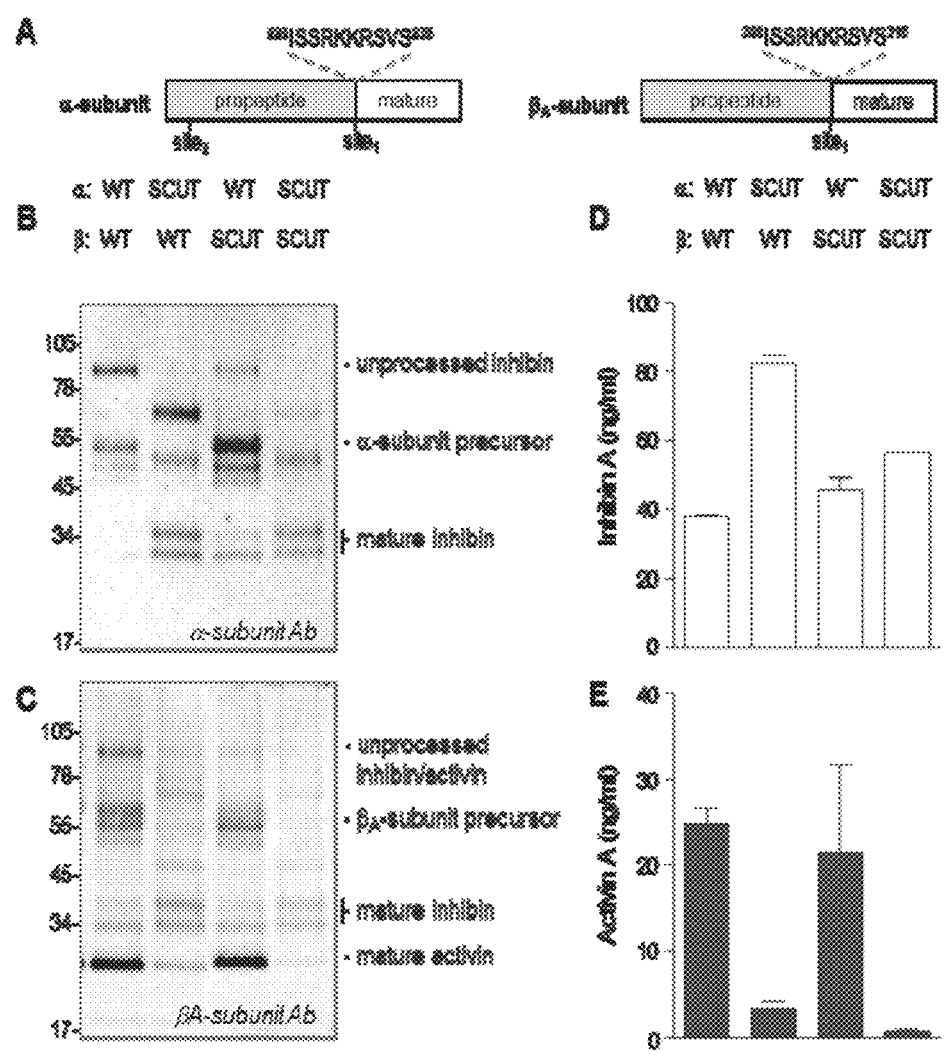
FIG. 1 is a graphical representation showing the effect of enhanced subunit processing on inhibin/activin production in mammalian cells. (A) The native cleavage sites (RXXR)

in the inhibin α- and β-subunits were enhanced by site-directed mutagenesis. (ISSRKKRSVSS (SEQ ID NO:18)). (B, C) Wild-type or mutant inhibin α- and $β_A$-subunits were co-transfected into HEK293F cells and the resultant inhibin and activin isoforms produced were assessed by Western blot, using antibodies to the α- and $β_A$-subunits (R1 and E4, respectively). (D, E) Specific ELISAs were used to quantitate inhibin and activin produced by HEK293F cells. Results are representative of n=3 experiments.

FIG. 2 is a graphical representation showing enhanced processing within the inhibin α-subunit precursor favors the production of mature inhibins. (A) The inhibin α-subunit uniquely contains a second processing site (site2) within its prodomain. This cleavage site was enhanced by targeted mutagenesis, alongside site1, which intervenes the pro- and mature domains. (RRRRRR (SEQ ID NO:47); ISSRKKRSVSS (SEQ ID NO:18)). (B, C) Wild-type or "super-cut" inhibin α- and $β_A$-subunits were co-transfected into HEK293F cells and the resultant inhibin and activin isoforms produced were assessed by Western blot (SCUT-S2 refers to α-subunit with both processing sites enhanced). (D, E) Densitometry was used to determine the relative expression of mature (31 kDa) inhibin A and activin A. Results are representative of n=3 experiments.

FIG. 3 is a graphical representation showing inactivation of residual activin A improves inhibin bioactivity. (A) An M418A mutation was incorporated into the βA-subunit to inhibit activin binding to its type I receptor (ALK4). (RRRRRR (SEQ ID NO:47); ISSRKKRSVSS (SEQ ID NO:18)). (B, C) The effect of the M418A mutation on inhibin and activin Biosynthesis was assessed by Western blot, using antibodies to the α- and $β_A$-subunits (R1 and E4, respectively). (D) The ability of inhibin M418A to suppress activin Bioactivity was determined using an LβT2 gonadotrope FSH bioassay. The LβT2 cells were stimulated with 200 pM activin A and treated with increasing doses of either Inhibin A-SCUT or Inhibin A-SCUT (M418A). (E) Activin Bioactivity within the inhibin preparations was assessed using an activin-responsive luciferase reporter assay (A3-Luc). Transfected HEK293T cells were treated with increasing doses of inhibin preparations, and activity determined by measuring luciferase activity. Results are representative of n=3 experiments.

FIG. 4 is a photographic or graphical representation showing purification of inhibin A-SCUT (M418A) by affinity chromatography. Inhibin A-SCUT (M418A) was purified using immobilized metal ion affinity chromatography (IMAC), and recovery assessed by Western blot (A) and ELISA (B).

FIG. 5 is a graphical representation showing analysis of Pro-inhibin bioactivity. IMAC purification enabled the isolation of pro-inhibin A complexes carrying the M418A mutation. The ability of Pro-inhibin A (M418A) to suppress activin-induced FSH release was compared to mature inhibin A in both (A) rat pituitary cell cultures, and (B) mouse gonadotrope LβT2 cells. (C) The ability of Pro-inhibin A (M418A) to suppress activin-induced SMAD2 phosphorylation was also assessed in LβT2 cells. Cells were treated with 200 pM activin A in the presence of increasing doses of Pro-inhibin A (M418A) or mature inhibin A. Representative result of n=3 experiments FIG. 6 is a graphical representation showing the effect of altering the transfection ratio of the α- and $β_A$-subunits on inhibin production. (A, B) The inhibin α- and $β_A$-subunits with super-cleavage sites (SCUT) were co-transfected into HEK293F cells at varying ratios and the resultant inhibin and activin isoforms produced were assessed by Western blot, using antibodies to the α- and $β_A$-subunits (R1 and E4, respectively). (C, D) Specific ELISAs were used to quantitate inhibin and activin produced by HEK293F cells. Results are representative of n=3 experiments.

FIG. 7 is a representation of human inhibin βA-subunit super-cut variant+M418A (ALK4) mutation+FLAG tag. (Nucleotide sequence (SEQ ID NO:49); amino acid sequence (SEQ ID NO:50)).

FIG. 8 is a representation of human inhibin α-subunit super-cut 1 variant+poly-his tag. (Nucleotide sequence (SEQ ID NO:7); amino acid sequence (SEQ ID NO:8)).

FIG. 9 is a representation of human inhibin α-subunit super-cut 2 variant (super-cut site1 and 2+poly-his tag). (Nucleotide sequence (SEQ ID NO:9); amino acid sequence (SEQ ID NO:10)).

FIG. 10 is a representation of human ($β_B$-subunit super-cut variant+M410A (ALK4) mutation+FLAG tag. (Nucleotide sequence (SEQ ID NO:51); amino acid sequence (SEQ ID NO:52)).

FIG. 11 is a photographic representation of purification of inhibin B analog (inhibin β-SCUT M410A) by affinity chromatography. Inhibin β-SCUT (M410A) was purified using IMAC and recovery assessed by Western blot comparing wild-type and mutants of α- and ($β_B$-subunits.

FIGS. 12A through C are photographic and graphical representations of (A) Western blot analysis of activin expression (E4 detection); (B) Western blot analysis of inhibin expression (R1 detection); (C) Activity data of super-cut mutant and $β_A$ 347H mutant.

FIGS. 13A and B are photographic and graphical representations of (A) Western blot analysis of activin expression (E4 detection); and (B) Activity data of super-cut mutant and $β_A$ A347H/Y345G double mutants.

FIG. 14 is a representation of human ($β_B$-subunit super-cut variant+M410A (ALK4) mutation+FLAG tag: with a modified signal sequence. This sequence has a Ser Arg His deleted as part of the supercut modification (compared to the wild-type sequence). (Nucleotide sequence (SEQ ID NO:51); amino acid sequence (SEQ ID NO:52)).

DETAILED DESCRIPTION

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

As used in the subject specification, the singular forms "a", "an" and "the" include plural aspects unless the context clearly dictates otherwise. Thus, for example, reference to "a variant" or "a mutation" includes a single variant or mutation, as well as two or more variants or mutations; reference to "an inhibin" includes a single inhibin, as well as two or more types of inhibins; reference to "the disclosure" includes a single and multiple aspects taught by the disclosure; and so forth. Aspects taught and enabled herein are encompassed by the term "invention". All such aspects are enabled within the width of the present invention. Any variants and derivatives contemplated herein are encompassed by "forms" of the invention.

Gonadal-derived inhibin A and inhibin B are components of the normal endocrine repertoire that regulated bone quality, and the loss of inhibins at menopause likely contributes to the accompanying decrease in bone mass. Therefore, inhibins have been touted as potential therapeutics for osteoporosis in post-menopausal women as well as the treatment of male and female subjects having a disease or condition exacerbated by low levels of inhibins and/or activin-mediated signaling. However, as heterodimeric proteins of α- and β ($β_A$ or $β_B$)-subunits, inhibins are difficult to produce recombinantly, they are poorly processed to their mature bioactive forms and their expression is always accompanied by production of activins (β-subunit homodimers).

The present invention provides a method for generating bioactive inhibin proteins in the form of bioactive inhibin analogs. The precursor form is also proposed herein to be bioactive. The method comprises:

(i) modifying a proprotein convertase cleavage site on one or both of the α-subunit precursor and/or a β-subunit precursor thereby making proprotein convertase cleavage more efficient;

(ii) optionally introducing a mutation to eliminate the type I receptor (ALK4) binding epitope in the β-subunit mature domain thereby rendering inactive any activin formed;

(iii) optionally introducing a mutation to disrupt homodimerization;

(iv) transfecting a cell or cell line with nucleic acid molecules encoding the α-subunit and β-subunit precursors as defined in (i) and optionally (ii) and optionally (iii);

(v) culturing the transfected cells or cell line for a time and under conditions sufficient for the inhibin precursor protein to be processed by a proprotein convertase and the processed protein released from the cell into conditioned medium; and (vi) isolating the inhibin or its precursor form from the conditioned medium.

Both the ALK4 and dimerization interface mutations may be included or one or other or neither. The modified α-subunit precursor and β-subunit precursor may be referred to as a variant, mutant, modified protein or analog or any other term indicating that the amino acid sequence has undergone a modification. In addition to a modified proprotein convertase cleavage site, the amino acid sequence of the α- and/or β-subunit may have one or more other amino acid substitutions, additions and/or deletions. The inhibin is of mammalian origin including a human or non-human primate, a laboratory test animal such as a mouse, rat, rabbit, guinea pig or hamster, a farm animal such as a sheep, cow, pig, horse or deer or a companion animal such as a dog or cat. In an embodiment, the inhibin is of human origin. Reference hereinafter to amino acid positions in a human inhibin includes the equivalent position in a non-human inhibin.

Reference to an "inhibin" includes inhibin A comprising a heterodimer of an α-subunit and a $β_A$-subunit and inhibin B comprising a heterodimer of an α-subunit and a $β_B$-subunit. The modified inhibin precursor protein and the inhibin generated therefrom may be referred to herein as a "inhibin precursor protein analog" and "inhibin analog", respectively. Both are proposed herein to be bioactive. Modified inhibin A is encompassed by the terms inhibin A variant, mutant, modified protein and analog. Modified inhibin B is encompassed by the terms inhibin B variant, mutant, modified protein and analog. This also applies to a modified inhibin A or inhibin B precursor protein. The inhibin A and/or inhibin B may also contain additional amino acid changes provided at least one proprotein convertase cleavage site on the α- and/or β-subunit precursor is rendered more efficiently cleavable by the convertase compared to wild-type α- and/or β-subunit precursors. Examples of additional mutations include an ALK4 mutation and a homodimerization interface mutation. In relation to homodimerization sites, these sites include A347, Y345, F326, V392, P393 and L396 in $β_A$-subunit (using the wild-type amino acid sequence in SEQ ID NO:2). Sites in $β_B$-subunit include F308, Y327, G329, I373, P374 and L377 (using the wild-type amino acid sequence in SEQ ID NO:12).

The inhibin α-subunit primary protein convertase cleavage site is at $^{229}$RARR$^{232}$ in human inhibin A (site1). When modified, a more efficient proprotein cleavage site is substituted comprising ISSRKKRSVSS (SEQ ID NO:18). At site 1 of α-subunit, the amino acid sequence is $^{229}$ISSRKKRSVSS$^{239}$ (SEQ ID NO:18). The substituted cleavage site may further be modified by one or more amino acid substitutions, additions and/or deletions to the amino acid sequence set forth in SEQ ID NO:18. Hence, the substituted proprotein cleavage site may comprise SEQ ID NO:18 or an amino acid sequence having at least 80% similarity to SEQ ID NO:18 after optimal alignment. Reference to "at least 80%" includes 80, 81, 82, 83, 84, 85, 86, 87, 88, 89, 90, 91, 92, 93, 94, 95, 96, 97, 98, 99 and 100%, or a percentage inbetween.

The α-subunit contains a secondary proprotein convertase site comprising $^{56}$RRLPRR$^{61}$ (site2). In an embodiment, the secondary cleavage site is substituted by $^{56}$RRRRRR$^{61}$ (SEQ ID NO:22). This amino acid sequence may comprise one or more amino acid substitutions, additions and/or deletions. The modification to change the cleavage sites are also referred to herein as "super-cut" variants. Generally, the primary cleavage site is referred to as super-cut site1 and the modified sequence is SEQ ID NO:18 and the secondary cleavage site is super-cut site2 with SEQ ID NO:22. The present invention may be practised with a wild-type α-subunit precursor, an α-subunit variant precursor with a modified site1, an α-subunit variant precursor with a modified site2 or an α-subunit variant precursor with a modified site1 and modified site2.

In an embodiment, the α-subunit variant precursor comprises both modifications at site1 and site 2.

The α-subunit variant precursor may further comprise a poly-histidine tag comprising the amino acid sequence HHHHHHHHH (SEQ ID NO:20). Such a tag is useful in the purification by affinity chromatography and to distinguish wild-type and modified inhibins.

Additional mutation(s) may also be added at the interface site for homodimerization to occur for $β_A+β_A$ dimerization into activin A and $β_B+β_B$ dimerization into activin B. Such mutations reduce or inhibit altogether functional activin molecules being produced. Examples include $A347X_1$, $Y345X_2$, $F326X_3$, $V392X_4$, $P393X_5$ and $L396X_6$ wherein each of $X_1$, $X_2$, $X_3$, $X_4$, $X_5$ and $X_6$ is any amino acid except A, Y, F, V, P and L, respectively (based on numbering in SEQ ID NO:2) in subunit $β_A$; and $F308X_7$, $Y327X_8$, $G329X_9$, $I373X_{10}$, $P374X_{11}$ and $L377X_{12}$ wherein each of $X_7$, $X_8$, $X_9$, $X_{10}$, $X_{11}$ and $X_{12}$ is any amino acid except F, Y, G, I, P and L, respectively (using numbering in SEQ ID NO:12). Particular examples including A347H, Y345G and A347H+ Y345G in $β_A$-subunit. In an embodiment, the amino acid sequence of $β_A$-subunit with an interface mutation is set forth in SEQ ID NO:40, 41 and 42 and includes an amino acid sequence having at least 80% similarity to any one of SEQ ID NO:40, 41 or 42 after optimal alignment provided the sequence comprises either a super-cut mutation and/or an interface mutation. The location of the mutations can be found in Tables 3 and 4. As above, reference to "at least 80%" includes 80, 81, 82, 83, 84, 85, 86, 87, 88, 89, 90, 91, 92, 93, 94, 95, 96, 97, 98, 99 and 100% or a percentage inbetween. Any mutation which reduces or inhibits homodimerization may be introduced into $\beta_A$ or $\beta_B$.

Hence, enabled herein is an inhibin α-subunit precursor comprising:

(i) a modified primary proprotein convertase site ("super-cut site1");

(ii) a modified secondary proprotein convertase site ("super-cut site2");

(iii) modified primary and secondary proprotein convertase sites; and optionally together with a poly-histidine tag to assist with purification.

Further enabled herein is an inhibin $\beta_A$-subunit precursor comprising a modified proprotein convertase site ("super-cut site");

optionally with a mutation disrupting the ALK4 binding epitope in the mature domain and optionally with a FLAG tag to assist in affinity chromatography purification and optionally with a mutation disrupting or eliminating homodimerization.

The inhibin $\beta_A$-subunit carries a primary proprotein convertase cleavage site at $^{306}$RRRRR$^{310}$ in human inhibin A. In an embodiment this is modified to ISSRKKRSVSS (SEQ ID NO:18) which is a more efficient cleavage site. In $\beta_A$-subunit, the amino acid sequence is $^{306}$ISSRKKRSVSS$^{316}$ (SEQ ID NO:18). As in the α-subunit, the substituted cleavage site may be further modified by one or more amino acid substitutions, additions and/or deletions to the amino acid sequence set forth in SEQ ID NO:18. Hence, the substituted proprotein cleavage site in $\beta_A$-subunit may comprise SEQ ID NO:18 or an amino acid sequence having at least 80% similarity to SEQ ID NO:18 after optimal alignment. As above, reference to "at least 80%" includes 80, 81, 82, 83, 84, 85, 86, 87, 88, 89, 90, 91, 92, 93, 94, 95, 96, 97, 98, 99 and 100% or a percentage inbetween.

The $\beta_A$-subunit variant precursor may further comprise a poly-histidine tag comprising the amino acid sequence HHHHHHHHH (SEQ ID NO:20) such a tag is useful in the purification by affinity chromatography.

In addition, the $\beta_A$-subunit mature domain may further contain a mutation to disrupt the type I receptor (ALK4) binding epitope. This results in inactive activin A (comprising the homodimers $\beta_A$-$\beta_A$). In an embodiment, the mutation is a single point mutation comprising an M418A substitution (numbering from start of prodomain [see SEQ ID NO:2; equivalent to M432A in SEQ ID NO:4]; equivalent to M108A from start of mature domain; in $\beta_B$-subunit, the site is M399A (from start of prodomain [see SEQ ID NO:12; equivalent to M410A in SEQ ID NO:14]). The effect of more efficient cleavage is an at least a 4 to 9 fold increase in cleavage compared to the wild-type protein. This includes a 4, 5, 6, 7, 8, or 9 fold increase. As indicated above, a mutation eliminating or reducing homodimerization of $\beta_A$ or $\beta_B$ may also be introduced (referred to as a dimerization interface mutation).

Taught herein is an inhibin $\beta_B$-subunit precursor comprising a modified proprotein convertase site ("super-cut site");

optionally with a mutation disrupting the ALK4 binding epitope in the mature domain and optionally with a FLAG tag to assist in affinity chromatography purification and optionally with a mutation disrupting or eliminating homodimerization.

The inhibin $\beta_B$-subunit carries a primary proprotein convertase cleavage site at $^{288}$RIRKR$^{292}$ in human inhibin B. In an embodiment this is modified to ISSRKKRSVSS (SEQ ID NO:18) which is a more efficient cleavage site. In $\beta_B$-subunit, the amino acid sequence is $^{288}$ISSRKKRSVSS$^{298}$ (SEQ ID NO:18). As in the α-subunit, the substituted cleavage site may be further modified by one or more amino acid substitutions, additions and/or deletions to the amino acid sequence set forth in SEQ ID NO:18. Hence, the substituted proprotein cleavage site in $\beta_B$-subunit may comprise SEQ ID NO:18 or an amino acid sequence having at least 80% similarity to SEQ ID NO:18 after optimal alignment. Reference to the "at least 80%" is as defined above.

The $\beta_B$-subunit variant precursor may further comprise a poly-histidine tag comprising the amino acid sequence HHHHHHHHH (SEQ ID NO:20) such a tag is useful in the purification by affinity chromatography.

In addition, the $\beta_B$-subunit may further contain a mutation to disrupt the type I receptor (ALK4) binding epitope. This results in inactive Activin A (comprising the homodimers $\beta_B$-$\beta_B$). In an embodiment, the mutation is a single point mutation comprising an M399A substitution (see numbering in SEQ ID NO:12; equivalent to M410A in SEQ ID NO:14). A dimerization interface mutation may also be introduced to reduce or eliminate homodimerization. Sites for homodimerization mutations are summarized in Tables 3 and 4.

The expression "at least 80%" has the same meaning as above.

Hence, to summarize the modifications, the α-subunit may comprise:

(i) a modified primary proprotein convertase site ("super-cut site 1"); and one or more of;

(ii) a modified secondary proprotein convertase site ("super-cut site 2"); and/or (iii) a poly-histidine tag to assist with purification;

which α-subunit forms a heterodimer with a $\beta_A$- or $\beta_B$-subunit wherein the $\beta_A$- or $\beta_B$-subunit comprises:

(i) a modified proprotein convertase site ("super-cut site"); and one or more of:

(ii) a mutation disrupting the ALK4 binding epitope in the mature domain;

(iii) a FLAG tag to assist in affinity chromatography purification; and/or (iv) a mutation disrupting or eliminating homodimerization.

In an embodiment, the □-subunit has (i), (ii) and (iii). In an embodiment, the $\beta_A$- or βn-subunit has (i), (ii), (iii) and (iv). In an embodiment, all mutations are present in the α- and β-subunits together.

Enabled herein is an inhibin analog precursor protein comprising an α-subunit having the amino acid sequence as set forth in SEQ ID NO:8 (super-cut site1+poly-his) or an amino acid sequence having at least 80% sequence similarity to SEQ ID NO:8 after optimal alignment with the proviso that it comprises at least one modified proprotein convertase site to enable more efficient cleavage by the convertase.

Enabled herein is an inhibin analog precursor protein comprising an $\beta_A$-subunit having the amino acid sequence as set forth in SEQ ID NO:4 (super-cut+ALK4 mutation+FLAG tag) or an amino acid sequence having at least 80% sequence similarity to SEQ ID NO:4 after optimal alignment with the proviso that it comprises at least one modified proprotein convertase site to enable more efficient cleavage by the convertase.

In an embodiment, an inhibin analog precursor protein is provided comprising an $\beta_A$-subunit having the amino acid sequence as set forth in SEQ ID NO:40 ($\beta_A$-subunit super-cut+ALK4 mutation+FLAG tag+interface mutation [A347H]) or an amino acid sequence having at least 80% sequence similarity to SEQ ID NO:40 after optimal alignment with the proviso that it comprises at least one modified proprotein convertase site to enable more efficient cleavage by the convertase.

In an embodiment, an inhibin analog precursor protein is provided comprising an $\beta_A$-subunit having the amino acid sequence as set forth in SEQ ID NO:41 ($\beta_A$-subunit super-cut+ALK4 mutation+FLAG tag+interface mutation [Y345G]) or an amino acid sequence having at least 80% sequence similarity to SEQ ID NO:41 after optimal alignment with the proviso that it comprises at least one modified proprotein convertase site to enable more efficient cleavage by the convertase.

In an embodiment, an inhibin analog precursor protein is provided comprising an $\beta_A$-subunit having the amino acid sequence as set forth in SEQ ID NO:42 ($\beta_A$-subunit super-cut+ALK4 mutation+FLAG tag+combined interface mutation [A347H/Y345G]) or an amino acid sequence having at least 80% sequence similarity to SEQ ID NO:42 after optimal alignment with the proviso that it comprises at least one modified proprotein convertase site to enable more efficient cleavage by the convertase.

Taught herein is an inhibin analog precursor protein comprising an $\alpha$-subunit having the amino acid sequence as set forth in SEQ ID NO:10 (super-cut site1 and 2+poly-his) or an amino acid sequence having at least 80% sequence similarity to SEQ ID NO:10 after optimal alignment with the proviso that it comprises at least one modified proprotein convertase site to enable more efficient cleavage by the convertase.

Further contemplated herein is an inhibin analog precursor protein comprising an $\beta_B$-subunit having the amino acid sequence as set forth in SEQ ID NO:14 (super-cut+ALK4 mutant+FLAG tag) or an amino acid sequence having at least 80% sequence similarity to SEQ ID NO:14 after optimal alignment with the proviso that it comprises at least one modified proprotein convertase site to enable more efficient cleavage by the convertase.

Hence, the $\alpha$- and/or $\beta$-subunit amino acid sequence may have amino acid substitutions, additions and/or deletions in addition to the modified proprotein convertase site. Such amino acid changes are those which would not render the inhibin inactive. The present invention extends to nucleic acid molecules encoding the modified $\alpha$- and $\beta_A$- or $\beta_B$-subunits.

Enabled herein is a nucleic acid molecule encoding an $\alpha$-subunit of inhibin comprising the nucleotide sequence set forth in SEQ ID NO:7 (super-cut site1 and poly-his) or a nucleotide sequence having at least 80% identity thereto after optimal alignment or a nucleotide sequence capable of hybridizing to the complement of SEQ ID NO:7 under stringency conditions.

Further enabled here is a nucleic acid molecule encoding an $\alpha$-subunit of inhibin comprising the nucleotide sequence set forth in SEQ ID NO:9 (super-cut site1 and poly-his) or a nucleotide sequence having at least 80% identity thereto after optimal alignment or a nucleotide sequence capable of hybridizing to the complement of SEQ ID NO:9 under stringency conditions.

A nucleic acid molecule encoding the $\beta_A$-subunit is encompassed by the present invention comprising the nucleotide sequence as set forth in SEQ ID NO:3 (super-cut site+ALK4 mutation+FLAG tag) or a nucleotide sequence having at least about 80% identity thereto after optimal alignment or a nucleic acid capable of hybridizing to the complement of SEQ ID NO:3 under stringency conditions.

Taught herein is a nucleic acid molecule encoding the $\beta_B$-subunit comprising the nucleotide sequence as set forth in SEQ ID NO:13 (super-cut site+ALK4 mutation+FLAG tag) or a nucleotide sequence having at least about 80% identity thereto after optimal alignment or a nucleic acid capable of hybridizing to the complement of SEQ ID NO:13 under stringency conditions.

The nucleic acid molecule may be in isolated form or operably linked to a promoter and optionally a terminating sequence or other regulatory sequences.

A method for generating a bioactive inhibin analog is contemplated herein the method comprising co-expressing in a cell or cell line nucleic acid encoding the $\alpha$-subunit and a $\beta_A$-subunit or $\beta_B$-subunit as defined herein for a time and under conditions sufficient for an inhibin precursor protein to be produced, cleaved by a proprotein convertase and secreted from the cell or cell line as a bioactive inhibin analog.

This leads to the generation of inhibin A analog or inhibin B analog.

In an embodiment, minimal bioactive activin A or activin B is produced.

In an embodiment, enabled herein is a process for generating a bioactive inhibin A, the method comprising transfecting a cell or cell line with a nucleic acid encoding an $\alpha$-subunit precursor comprising the nucleotide sequence as set forth in SEQ ID NO:7 or a nucleic acid having at least 80% identity to SEQ ID NO:7 (super-cut site1+poly-his) or is capable of hybridizing to the complement of SEQ ID NO:7 with the proviso that the nucleic acid comprises a modified proprotein cleavage site encoded by SEQ ID NO:17; and transfecting the cell or cell line with a nucleic acid encoding a $\beta_A$-subunit precursor comprising the nucleotide sequence as set forth in SEQ ID NO:3 (super-cut+ALK4 mutation+FLAG tag) or a nucleic acid having at least 80% identity to SEQ ID NO:3 or is capable of hybridizing to the complement of SEQ ID NO:3 with the proviso that the nucleic acid comprises a modified proprotein convertase cleavage site encoded by SEQ ID NO:17; and culturing the cells for a time and under conditions sufficient for the $\alpha$-subunit and $\beta_A$-subunit variants to be processed by the proprotein convertase and to release inhibin A analog with minimal bioactive activin A.

In another embodiment, the $\alpha$-subunit variant comprises the modified primary and secondary proprotein convertase cleavage sites. In an embodiment, enabled herein is a process for generating a bioactive inhibin A with minimal bioactive activin A, the method comprising transfecting a cell or cell line with a nucleic acid encoding an $\alpha$-subunit precursor comprising the nucleotide sequence as set forth in SEQ ID NO:9 (super-cut site1 and 2+poly-his) or a nucleic acid having at least 80% identity to SEQ ID NO:9 or is capable of hybridizing to the complement of SEQ ID NO:9 with the proviso that the nucleic acid comprises a modified proprotein cleavage site encoded by SEQ ID NO:17 and SEQ ID NO:21; and transfecting the cell or cell line with a nucleic acid encoding a $\beta_A$-subunit precursor comprising the nucleotide sequence as set forth in SEQ ID NO:3 (super-cut site+ALK mutation+FLAG tag) or a nucleic acid having at least 80% identity to SEQ ID NO:3 or is capable of hybridizing to the complement of SEQ ID NO:3 with the proviso that the nucleic acid comprises a modified proprotein convertase cleavage site encoded by SEQ ID NO:17; and culturing the cells for a time and under conditions sufficient for the $\alpha$-subunit and $\beta_A$-subunit variants to be processed by the proprotein convertase and to release inhibin A analog with minimal bioactive activin A.

In relation to an inhibin B analog, again the $\alpha$-subunit may contain only the primary proprotein cleavage site modified. Hence, taught herein is a process for generating a bioactive inhibin B with minimal bioactive activin B, the method comprising transfecting a cell or cell line with a nucleic acid encoding an α-subunit precursor comprising the nucleotide sequence as set forth in SEQ ID NO:7 (super-cut site1+poly-his) or a nucleic acid having at least 80% identity to SEQ ID NO:7 or is capable of hybridizing to the complement of SEQ ID NO:7 with the proviso that the nucleic acid comprises a modified proprotein cleavage site encoded by SEQ ID NO:17; and transfecting the cell or cell line with a nucleic acid encoding a $β_B$-subunit precursor comprising the nucleotide sequence as set forth in SEQ ID NO:13 (super-cut+ALK mutation+FLAG tag) or a nucleic acid having at least 80% identity to SEQ ID NO:13 or is capable of hybridizing to the complement of SEQ ID NO:13 with the proviso that the nucleic acid comprises a modified proprotein convertase cleavage site encoded by SEQ ID NO:17; and culturing the cells for a time and under conditions sufficient for the α-subunit and $β_B$-subunit variants to be processed by the proprotein convertase and to release inhibin B analog with minimal bioactive activin B.

Still in a further embodiment, the α-subunit comprises both the primary and secondary proprotein convertase cleavage sites modified. The subject specification is hence instructional for a process for generating a bioactive inhibin B with minimal bioactive activin B, the method comprising transfecting a cell or cell line with a nucleic acid encoding an α-subunit precursor comprising the nucleotide sequence as set forth in SEQ ID NO:9 (super-cut sites1 and 2+poly-his) or a nucleic acid having at least 80% identity to SEQ ID NO:9 or is capable of hybridizing to the complement of SEQ ID NO:9 with the proviso that the nucleic acid comprises a modified proprotein cleavage site encoded by SEQ ID NO:17; and transfecting the cell or cell line with a nucleic acid encoding a $β_B$-subunit precursor comprising the nucleotide sequence as set forth in SEQ ID NO:13 (super-cut+ALK4 mutation+FLAG tag) or a nucleic acid having at least 80% identity to SEQ ID NO1:3 or is capable of hybridizing to the complement of SEQ ID NO:13 with the proviso that the nucleic acid comprises a modified proprotein convertase cleavage site encoded by SEQ ID NO:17; and culturing the cells for a time and under conditions sufficient for the α-subunit and $β_B$-subunit variants to be processed by the proprotein convertase and to release inhibin B analog with minimal bioactive activin B.

As indicated above, the amino acid sequence of α- and/or β-subunit precursor and/or mature form may have one or more amino acid substitutions, additions and/or deletions which do not render the inhibin inactive. Such changes may enhance activity or render the inhibin more stable. It is well understood in the art that some amino acids may be changed to others with broadly similar properties without changing the nature of the activity of the polypeptide. Variant polypeptides encompassed by the present invention are those which are biologically active, that is, they continue to possess the antagonistic biological activity of the propeptide towards an activin or the ability to confer higher affinity binding as described herein. Amino acid modifications are preferably conservative amino acid substitutions although additions and/or deletions may also be made. Examples include the addition of homodimerization interface mutations.

Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel (1985) *Proc. Natl. Acad. Sci. USA*. 82:488-492; Kunkel et al. (1987) *Methods in Enzymol,* 154:367-382; U.S. Pat. No. 4,873,192; Watson et al. (1987) "Molecular Biology of the Gene", Fourth Edition, Benjamin/Cummings, Menlo Park, Calif. and the references cited therein. Guidance as to appropriate amino acid substitutions that do not affect biological activity of the protein of interest may be found in the model of Dayhoff et al. (1978) *Atlas of Protein Sequence and Structure*, Natl. Biomed. Res. Found., Washington, D.C.

Variant propeptides may contain conservative amino acid substitutions at various locations along their sequence, as compared to a parent (e.g. naturally-occurring or reference) amino acid sequence. A "conservative amino acid substitution" is one in which the amino acid residue is replaced with an amino acid residue having a similar side chain. Families of amino acid residues having similar side chains have been defined in the art, which can be generally sub-classified as follows:

Acidic: The residue has a negative charge due to loss of H ion at physiological pH and the residue is attracted by aqueous solution so as to seek the surface positions in the conformation of a peptide in which it is contained when the peptide is in aqueous medium at physiological pH. Amino acids having an acidic side chain include glutamic acid and aspartic acid.

Basic: The residue has a positive charge due to association with H ion at physiological pH or within one or two pH units thereof (e.g. histidine) and the residue is attracted by aqueous solution so as to seek the surface positions in the conformation of a peptide in which it is contained when the peptide is in aqueous medium at physiological pH. Amino acids having a basic side chain include arginine, lysine and histidine.

Charged: The residues are charged at physiological pH and, therefore, include amino acids having acidic or basic side chains (i.e. glutamic acid, aspartic acid, arginine, lysine and histidine).

Hydrophobic: The residues are not charged at physiological pH and the residue is repelled by aqueous solution so as to seek the inner positions in the conformation of a peptide in which it is contained when the peptide is in aqueous medium. Amino acids having a hydrophobic side chain include tyrosine, valine, isoleucine, leucine, methionine, phenylalanine and tryptophan.

Neutral/polar: The residues are not charged at physiological pH, but the residue is not sufficiently repelled by aqueous solutions so that it would seek inner positions in the conformation of a peptide in which it is contained when the peptide is in aqueous medium. Amino acids having a neutral/polar side chain include asparagine, glutamine, cysteine, histidine, serine and threonine.

This description also characterizes certain amino acids as "small" since their side chains are not sufficiently large, even if polar groups are lacking, to confer hydrophobicity. With the exception of proline, "small" amino acids are those with four carbons or less when at least one polar group is on the side chain and three carbons or less when not. Amino acids having a small side chain include glycine, serine, alanine and threonine. The gene-encoded secondary amino acid proline is a special case due to its known effects on the secondary conformation of peptide chains. The structure of proline differs from all the other natural-occurring amino acids in that its side chain is bonded to the nitrogen of the α-amino group, as well as the α-carbon. Several amino acid similarity matrices (e.g. PAM120 matrix and PAM250 matrix as disclosed for example by Dayhoff et al. (1978) supra, A model of evolutionary change in proteins.

The degree of attraction or repulsion required for classification as polar or non-polar is arbitrary and, therefore, amino acids specifically contemplated by the invention have been classified as one or the other. Most amino acids not specifically named can be classified on the basis of known behavior.

Amino acid residues can be further sub-classified as cyclic or non-cyclic, and aromatic or non-aromatic, self-explanatory classifications with respect to the side-chain substituent groups of the residues, and as small or large. The residue is considered small if it contains a total of four carbon atoms or less, inclusive of the carboxyl carbon, provided an additional polar substituent is present; three or less if not. Small residues are, of course, always non-aromatic. Dependent on their structural properties, amino acid residues may fall in two or more classes.

Conservative amino acid substitution also includes groupings based on side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. For example, it is reasonable to expect that replacement of a leucine with an isoleucine or valine, an aspartate with a glutamate, a threonine with a serine, or a similar replacement of an amino acid with a structurally related amino acid will not have a major effect on the properties of the resulting variant polypeptide. Whether an amino acid change results in a functional peptide polypeptide can readily be determined by assaying its activity. Amino acid substitutions falling within the scope of the invention, are, in general, accomplished by selecting substitutions that do not differ significantly in their effect on maintaining (a) the structure of the peptide backbone in the area of the substitution, (b) the charge or hydrophobicity of the molecule at the target site, or (c) the bulk of the side chain. After the substitutions are introduced, the variants are screened for biological activity as described herein.

Alternatively, similar amino acids for making conservative substitutions can be grouped into three categories based on the identity of the side chains. The first group includes glutamic acid, aspartic acid, arginine, lysine, histidine, which all have charged side chains; the second group includes glycine, serine, threonine, cysteine, tyrosine, glutamine, asparagine; and the third group includes leucine, isoleucine, valine, alanine, proline, phenylalanine, tryptophan, methionine, as described in Zubay (1993) *Biochemistry*, third edition, Wm.C. Brown Publishers.

Thus, a predicted non-essential amino acid residue in a precursor inhibin polypeptide subunit is typically replaced with another amino acid residue from the same side chain family. A "non-essential" amino acid residue is a residue that can be altered from the reference sequence of an embodiment polypeptide without abolishing or substantially altering one or more of its activities. Suitably, the alteration does not substantially alter one of these activities, for example, the activity is at least 60%, 70%, 80%, 90% or 100% of the reference sequence. By contrast, an "essential" amino acid residue is a residue that, when altered from the wild-type sequence of a reference polypeptide, results in abolition of an activity of the parent molecule such that less than 20% of the activity of the reference polypeptide is present. In an embodiment, essential amino acid residues include those that are conserved in inhibin polypeptides across different species.

The propeptides of the present invention may be prepared by any suitable procedure known to those of skill in the art. Recombinant propeptides can be conveniently prepared using standard protocols as described for example in Sambrook et al. *Molecular Cloning:A Laboratory Manual*, 2nd ed., Cold Spring Harbor, in particular Sections 13, 16 and 17; Ausubel et al. (1994) Current Protocols in Molecular Biology, John Wiley & Sons Inc, in particular Chapters 10 and 16; and Coligan et al. (1995-1997) Current Protocols in Protein Science, John Wiley & Sons, Inc., Chapters 1, 5 and 6. Methods of purification include size exclusion, affinity or ion exchange chromatography/separation. The identity and purity of peptides is determined for example by SDS-polyacrylamide electrophoresis or chromatographically such as by high performance liquid chromatography (HPLC). Alternatively, the propeptides or parts of the propeptides may be synthesized by chemical synthesis, e.g. using solution synthesis or solid phase synthesis as described, for example, in Chapter 9 of Atherton and in Roberge et al. (1995) *Science*, 269:202). In some embodiments, the propeptides are prepared by recombinant techniques. For example, the inhibin analogs of the present invention may be prepared by a procedure including the steps of: (a) preparing a construct comprising a nucleic acid sequence that encodes an □- or □-subunit modified as herein described and that is operably linked to a regulatory element; (b) introducing (e.g. transfecting) the construct into a host cell or cell line; (c) culturing the host cell to express the nucleic acid to thereby produce the encoded subunit precursors; and (d) isolating the processed inhibin or its precursor from conditioned medium.

The invention also contemplates variants of the nucleic acid molecules encoding the subject modified propeptides including the dimerization domain. Nucleic acid variants can be naturally-occurring (native), such as allelic variants (same locus), homologs (different locus), and orthologs (different organism) or can be non naturally-occurring. Naturally-occurring nucleic acid variants such as these can be identified with the use of well-known molecular biology techniques, as, for example, with polymerase chain reaction (PCR) and hybridization techniques as known in the art. Non-naturally occurring polynucleotide variants can be made by mutagenesis techniques, including those applied to polynucleotides, cells, or organisms. The variants can contain nucleotide substitutions, deletions, inversions and insertions. Variation can occur in either or both the coding and non-coding regions. The variations can produce both conservative and non-conservative amino acid substitutions (as compared in the encoded product) and glycosylation variants. For nucleotide sequences, conservative variants include those sequences that, because of the degeneracy of the genetic code, encode the amino acid sequence of a reference polypeptide. Variant nucleotide sequences also include synthetically derived nucleotide sequences, such as those generated, for example, by using site-directed mutagenesis but which still encode a polypeptide. Variants of a particular nucleic acid sequence will have at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or more sequence identity to that particular nucleotide sequence as determined by sequence alignment programs known in the art using default parameters.

The term "sequence identity" as used herein refers to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g. A, T, C, G, I, U) or the identical amino acid residue (e.g. Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e. the window size), and multiplying the result by 100 to yield the percentage of sequence identity.

A comparison window may comprise additions or deletions (i.e. gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e. resulting in the highest percentage homology over the comparison window) generated by any of the various methods selected. Reference also may be made to the BLAST family of programs as for example disclosed by Altschul et al. (1997) *Nucl. Acids Res.* 25:3389. A detailed discussion of sequence analysis can be found in Unit 19.3 of Ausubel et al. (1994-1998) "Current Protocols in Molecular Biology", John Wiley & Sons Inc, Chapter 15.

In another aspect, the invention provides a purified nucleic acid molecule that comprises a nucleotide sequence encoding the herein described inhibin subunit precursors including variants having substantial sequence identity or ability to cross hybridise under stringent hybridization conditions, synonymous codon variants and codon optimized variants thereof.

As known in the art, "stringency" refers to the temperature and ionic strength conditions, and presence or absence of certain organic solvents, during hybridization and washing procedures. The higher the stringency, the higher will be the degree of complementarity between nucleic acid sequences that remain hybridized after washing. The term "high stringency" etc. refers to temperature and ionic conditions under which only nucleotide sequences having a high frequency of complementary bases will hybridize. The stringency required is nucleotide sequence dependent and depends upon the various components present during hybridization. The stringency conditions may be high, medium or low.

The nucleotide sequence may comprise codon substitution with a synonymous codon. The term "synonymous codon" as used herein refers to a codon having a different nucleotide sequence compared to another codon but encoding the same amino acid as that other codon. Codon optimization is standard in the art and is contemplated herein.

In another aspect the present specification provides nucleic acid constructs encoding a modified propeptide as described herein or a functional fragment thereof. Illustrative nucleic acid sequences characterizing the subject nucleic acid molecules are set out in Table 1 and include SEQ ID NO:3 ($\beta_A$-subunit with super-cut site+ALK4 mutation+FLAG tag), SEQ ID NO:13 ($\beta_B$-subunit with super-cut site+ALK4 mutation+FLAG tag), SEQ ID NO:7 ($\alpha$-subunit super-cut site1+poly-his) and SEQ ID NO:9 ($\alpha$-subunit super-cut sites1 and 2+poly-his).

The invention extends to vectors and other constructs comprising isolated nucleic acid molecules including those capable of expressing (producing) the subject inhibin subunit precursors and to isolated host cells or cell lines comprising same.

By "vector" is meant a polynucleotide molecule, suitably a DNA molecule derived, for example, from a plasmid, bacteriophage, yeast or virus, into which a nucleic acid molecule can be inserted or cloned. A vector may contain one or more unique restriction sites and can be capable of autonomous replication in a defined host cell including a target cell or tissue or a progenitor cell or tissue thereof, or be integral with the genome of the defined host such that the cloned sequence is reproducible. Accordingly, the vector can be an autonomously replicating vector, i.e. a vector that exists as an extra-chromosomal entity, the replication of which is independent of chromosomal replication, e.g. a linear or closed circular plasmid, an extra-chromosomal element, a mini-chromosome, or an artificial chromosome. The vector can contain any means for assuring self-replication. Alternatively, the vector can be one which, when introduced into the host cell, is integrated into the genome and replicated together with the chromosome(s) into which it has been integrated. A vector system can comprise a single vector or plasmid, two or more vectors or plasmids, which together contain the total DNA to be introduced into the genome of the host cell, or a transposon. The choice of the vector will typically depend on the compatibility of the vector with the host cell into which the vector is to be introduced. In the present case, the vector is preferably a viral or viral-derived vector, which is operably functional in animal and preferably mammalian cells. Such vector may be derived from a poxvirus, an adenovirus or yeast. The vector can also include a selection marker such as an antibiotic resistance gene that can be used for selection of suitable transformants. Examples of such resistance genes are known to those of skill in the art and include the nptII gene that confers resistance to the antibiotics kanamycin and G418 [Geneticin (Registered Trade Mark)] and the hph gene that confers resistance to the antibiotic hygromycin B.

Vectors useful for expressing the subject nucleotide sequence in subject host cells in vivo are known to those of skill in the art and are expressly contemplated. They include adenoviral vectors and adeno-associates virus vectors. Illustrative vectors include AAV8 or AAV6 described for example in Qiao et al. (2008) *Human Gene Therapy* 19:000-000.

In another embodiment host cells are provided comprising a nucleic acid construct encoding a modified inhibin subunit precursors as described herein, wherein the host cell or cell line expresses the precursor.

Host cells are conveniently eukaryotic cells include mammalian, plant, yeast and insect cells as known in the art. Recombinant proteins are produced by culturing the host cells for a period of time sufficient to allow for expression of the modified polypeptide inhibin subunits in the host cells or, more preferably, secretion of the protein into the culture medium in which the host cells are grown. Suitable mammalian cell lines include, but are not limited to, HEK293T, HEK293, HEK293T-Rex, BHK, VERO, HT1080, RD, COS-7, CHO, Jurkat, HUT, SUPT, C8166, MOLT4/clone8, MT-2, MT-4, H9, PM1, CEM, myeloma cells (e.g. SB20 cells) and CEMX174 are available, for example, from the ATCC. Other host cells include without limitation yeast, e.g.

*Pichia pastoris*, or insect cells such as Sf9 cells although such molecules would not ordinarily be glycosylated.

In another aspect the present invention provides a method of treating or preventing activin-induced conditions, such as muscle wasting, fibrosis or inflammation in a subject, the method comprising administering to the subject an inhibin analog or precursor thereof as described herein or a nucleic acid construct encoding same which provides the modified α- and β-subunits to the subject. In an embodiment, the inhibin analog is inhibin A analog comprising an α-subunit having the amino acid sequence set forth in SEQ ID NO:7 or 9 or an amino acid sequence that is at least 80% identical to SEQ ID NO:7 or 9 and $\beta_A$-subunit having the amino acid sequence set forth in SEQ ID NO:3 or an amino acid sequence that is at least 80% identical to SEQ ID NO:3.

In another aspect the present invention provides a method of treating or preventing activin-induced conditions, such as muscle wasting, fibrosis or inflammation in a subject, the method comprising administering to the subject an inhibin analog or precursor thereof as described herein or a nucleic acid construct encoding same which provides the modified α- and β-subunits to the subject. In an embodiment, the inhibin analog is inhibin B analog or precursor comprising an α-subunit having the amino acid sequence set forth in SEQ ID NO:7 or 9 or an amino acid sequence that is at least 80% identical to SEQ ID NO:7 or 9 and $\beta_A$-subunit having the amino acid sequence set forth in SEQ ID NO:9 or an amino acid sequence that is at least 80% identical to SEQ ID NO:9.

In these embodiments, minimal bioactive activin A or B is generally produced. In an embodiment, any similar inhibin generally comprises a β-subunit chain with a mutation in the ALK4 binding epitope. In an embodiment, homodimerization interface mutations are included in $\beta_A$- or $\beta_B$-subunits (for example, refer to Tables 3 and 4).

"Subjects" contemplated in the present invention are humans or mammals including laboratory or art accepted test or vehicle animals. "Subjects" include human subjects in need of treatment or prophylaxis.

Usefully, the present invention further provides compositions comprising an inhibin analog or its precursor or nucleic acid encoding inhibin subunits as herein described. The term "compound" includes "medicament", "agent", "therapeutic", "pharmacologically acceptable compound" and "pharmaceutical composition" and the like. In another embodiment, the composition comprises a pharmaceutically or physiologically acceptable carrier or diluent. In an embodiment, the inhibin analog or its precursor are for use in the treatment or prevention of conditions or symptoms of conditions promoted or exacerbated by activin signaling.

Pharmaceutical compositions are conveniently prepared according to conventional pharmaceutical compounding techniques. See, for example, Remington's Pharmaceutical Sciences (1990) 18th Ed., Mack Publishing, Company. These compositions may comprise, in addition to one of the active substances (inhibin analog or its precursor), a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g. intravenous, oral or parenteral.

The inhibin analogs or their precursors or compositions comprising same are administered in an effective amount. The terms "effective amount" includes "therapeutically effective amount" and "prophylactically effective amount" and mean a sufficient amount of active either in a single dose or as part of a series or slow release system which provides the desired therapeutic, preventative, or physiological effect in some subjects. Undesirable effects, e.g. side effects, may sometimes manifest along with the desired therapeutic effect; hence, a practitioner balances the potential benefits against the potential risks in determining an appropriate "effective amount". The exact amount of composition required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using routine skills or experimentation. The term "treatment" refers to any measurable or statistically significant amelioration in at least some subjects in one or more symptoms of a condition associated with disregulated or overactive activin signaling in a subject. Prophylactic administration of the compound serves to prevent or attenuate onset of symptoms of a condition associated with disregulated or overactive activin signaling in a subject. In an embodiment, the subject is a post-menopausal female subject with reduced levels of serum inhibin and has or is at risk of developing a bone disorder such as osteoporosis.

A "pharmacologically acceptable" composition is one tolerated by a recipient patient. A "pharmaceutically acceptable carrier and/or a diluent" is a pharmaceutical vehicle comprised of a material that is not otherwise undesirable i.e. it is unlikely to cause a substantial adverse reaction by itself or with the active composition. Carriers may include all solvents, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes.

For oral administration, the compositions can be formulated into solid or liquid preparations such as capsules, pills, tablets, lozenges, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. Tablets may contain a binder such as tragacanth, corn starch or gelatin; a disintegrating agent, such as alginic acid; and a lubricant, such as magnesium stearate. If desired, tablets may be sugar-coated or enteric-coated by standard techniques. The active composition can be encapsulated to make it stable to passage through the gastrointestinal tract. See for example, International Patent Publication No. WO 96/11698.

For parenteral administration, the composition may be dissolved in a carrier and administered as a solution or a suspension. For transmucosal or transdermal (including patch) delivery, appropriate penetrants known in the art are used for delivering the composition. For inhalation, delivery uses any convenient system such as dry powder aerosol, liquid delivery systems, air jet nebulizers, propellant systems. For example, the formulation can be administered in the form of an aerosol or mist. The compositions may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences, 1990 (supra). In some embodiments the formulations may be incorporated in lipid monolayers or bilayers such as liposomes or micelles. Targeting therapies known in the art may be used to deliver the agents more specifically to certain types of cells or tissues.

The present invention further contemplates antibodies to the inhibin analogs, their precursors or their α- or β-subunits. Such antibodies are useful inter alia in affinity purification techniques as well as quenching agents to inhibit activity if required.

Polyclonal antibodies may be generated, however, the use of monoclonal antibodies is particularly preferred because of the ability to produce them in large quantities and the homogeneity of the product. The preparation of hybridoma cell lines for monoclonal antibody production is derived by fusing an immortal cell line and lymphocytes sensitized against the immunogenic preparation (i.e. comprising 35-LM polypeptide) or can be done by techniques which are well known to those who are skilled in the art. (See, for example, Douillard and Hoffman (1981) Basic Facts about Hybridomas, in Compendium of Immunology Vol. II, ed. by Schwartz; Kohler and Milstein (1975) Nature 256:495-499; Kohler and Milstein (1976) European Journal of Immunology 6:511-519). Single chain antibodies or transgenic mice expressing humanized antibodies or other recognition proteins may also be used. Useful proteins in this regard include diabodies, peptide mimetics and antibody fragments such as scFv fragments and Fab fragments.

Monoclonal antibodies which bind specifically to the inhibin analogs or their precursors or their α- or β-subunits provide a convenient method for detecting and targeting the cells which express the inhibin analogs. The presence of a particular inhibin analog or precursor form or subunit may be accomplished in a number of ways such as by Western blotting and ELISA procedures. A wide range of immunoassay techniques are available as can be seen by reference to U.S. Pat. Nos. 4,016,043, 4,424,279 and 4,018,653. These include both single-site and two-site or "sandwich" assays of the non-competitive types, as well as in the traditional competitive binding assays. These assays also include direct binding of a labeled antibody to a target. Monoclonal antibodies may be used as antagonists of inhibin analog activity. They may also be formulated as a composition suitable for administration to an individual in a method of treatment or prophylaxis.

The antibodies of the present invention are useful in a range of other methodologies including flow cytometry, which typically detects optical parameters. For example, a flow cytometer may be used to determine forward scatter (which is a measure of size of a carrier), side scatter (which is sensitive to refractive index and size of a particle [see Shapiro (1995) "Practical flow cytometry", 3$^{rd}$ ed. Brisbane, Wiley-Liss]) and fluorescent emission.

EXAMPLES

Aspects disclosed herein are further described by the following non-limiting Examples. Certain technical details have since the priority date been included in Walton et al. (2016) Endocrinology 157:2799-2809 the entire contents of which are incorporated herein by reference.

Methods

Generation of Mutant Inhibins

The cleavage sites intervening the pro- and mature domains in the inhibin α- and $β_A$-subunits were modified using site-directed mutagenesis. A pCDNA3.1 (Invitrogen, Carlsbad, Calif.) vector containing either the full-length wild-type human inhibin α-subunit (sequence reference NM_002191.3), or the $β_A$-subunit (sequence reference NM_002192.2) served as the templates in these reactions. The native furin cleavage sites (RXXR) were replaced with an ideal theoretical site (ISSRKKRSVSS-SEQ ID NO:18) [Duckert et al. (2004) Protein Eng Des Selec. 17:107-112] to enhance the processing of pro-inhibin forms. This was achieved by overlap extension PCR, using designed 'supercut' (SCUT) primers in combination with primers flanking the ORFs (primer details provided in Table 3) to enable cloning into compatible sites of pCDNA3.1. To aid purification, a poly-histidine tag was inserted at a previously determined permissive site (Walton et al. (2013) Mol Cell Endocrinol. 381:106-114), immediately prior to the pro:mature cleavage site. This was achieved using 'polyHIStag' primers in combination with flanking primers as outlined in Table 5, to enable cloning into pCDNA3.1. All constructs were verified by DNA sequencing.

Inhibin variants were produced by transient transfection in human embryonic kidney (HEK293T) cells using Lipofectamine 2000 (Invitrogen). In brief, cells were plated at $8 \times 10^5$ cells per well in 6-well plates. Wild-type or mutant α-subunit constructs were combined with $β_A$-subunit variants, and Lipofectamine 2000 was added according to the manufacturer's instructions. After a 20 minute incubation, DNA/Lipofectamine complexes were added directly to the plated cells and incubated in serum-free Opti-MEM medium (Invitrogen) for a further 48 hours at 37° C. in 5% v/v $CO_2$.

Western blotting was used to assess inhibin and activin forms in the conditioned medium from transfected HEK293T. At 48 hours after transfection, conditioned medium was combined with 4×LDS loading dye (Invitrogen), and non-reduced samples were separated by 10% w/v SDS-PAGE. After electrophoresis, samples were transferred onto ECL Hybond membranes (GE Healthcare, Giles, Buckinghamshire, UK). Membranes were blocked for a minimum of 1 hour in 1% w/v BSA in Tris-buffered Saline with 0.05% v/v Tween-20 (TBS-T). Inhibin forms were detected using antibodies to the inhibin $β_A$-(E4, binds residues 401-413 (19)), or α-subunit (R1, binds residues 233-264 [Groome et al. (1994) Clin Endocrinol. 40:717-723]). The E4 antibody was obtained from Beckman Coulter (Chaska, USA) or Oxford Brookes University (Oxford, UK), and requires an antigen retrieval step during incubation (6% v/v $H_2O_2$). Antibodies were incubated in 1% w/v BSA/TBS-T for 2 hours and excess antibody removed by multiple washes with TBS-T. Bound R1 and E4 antibodies were then detected by incubation with a mouse secondary antibody conjugated to horseradish peroxidise (mouse IgG-HRP, GE lifesciences). Following multiple washes, chemiluminescence was measured using Lumilight substrates (Roche Applied Sciences) and a Bio-Rad Chemidoc XRS System.

Quantification of Inhibin

Inhibin A levels were determined using recently described inhibin ELISA (Walton et al. (2013) supra), which employs the $β_A$-subunit mAb (E4) as a capture antibody, and α-subunit mAb (R1) as the label. For the purposes of this study, all samples were assayed in the low-triton assay format, which favors detection of the mature or 'active' inhibin forms. Samples and standards were first treated with a low-triton assay buffer (0.1% v/v Triton X-100, 1% w/v BSA in TBS), and then oxidized using 1% v/v $H_2O_2$ (final concentration). Bound inhibin was labelled using biotinylated-R1 antibody diluted in the low-triton assay buffer. Following R1 labelling, plates were treated with Strep-HRP, then washed and developed with TMB substrate (3,3',5,5'-tetramethylbenzidine, Invitrogen). The ELISA was stopped using 0.1 M $H_2SO_4$, and absorbance determined at 450 nM on a SpectraMax plate reader (Molecular devices, CA). Assay sensitivity was 6 pg/ml. Purified 34 kDa inhibin A generated by the laboratory was used as a reference standards (Makanji et al. (2007) *Endocrinology* 148:2309-2316).

Quantification of Activin

Activin A was measured using a specific ELISA (Oxford Bioinnovations). In brief, activin A standard and samples (diluted in 5% w/v BSA) in PBS, pH 7.4) were treated with SDS (final concentration 3% w/v) and boiled for 3 minutes. Once cooled, samples were treated with $H_2O_2$ (final concentration 2% v/v) and incubated for 30 minutes at room temperature. Samples were added to E4 antibody-coated plates and incubated for 1 hour at room temperature. Plates were then probed with biotinylated-E4 antibody and incubated overnight at room temperature. After washing, a streptavidin-horseradish peroxidase (HRP) conjugate was added to the wells and incubated at room temperature for 1 hour. Following further washes, HRP activity was detected with TMB substrate (3,3',5,5'-tetramethylbenzidine; Life Technologies).

Production and Purification of Inhibins by IMAC

Pro-inhibin forms were produced by transient transfection in HEK293T cells using lipofectamine 2000. In brief, cells were plated at $11 \times 10^6$ cells per plate on 15 cm plates, and then transfected with an equal ratio of inhibin α- and β-subunit DNA constructs using Lipofectamine 2000 and Opti-MEM media (Invitrogen, according to the manufacturers protocol). Pro-inhibin was then isolated from conditioned media by IMAC immunoaffinity. Conditioned media (100 ml) was first concentrated (twice) using centricon devices with a 5 kDa molecular weight cut-off (Millipore) and resuspended in phosphate buffer (50 mM $PO_4$, 0.5 M NaCl, pH 8.0). Concentrated media was applied to a Nickel-NTA resin (Invitrogen) and incubated overnight at 4° C. Unbound protein was collected, and the resin washed 4× with phosphate buffer. Bound inhibins were eluted with 0.5 M imidazole in phosphate buffer (50 mM $PO_4$, 0.5 M NaCl, pH 8.0). Imidazole was removed by buffer exchange on a PD-10 column (GE Healthcare), and 0.1% w/v BSA was applied to the preparations. IMAC purification was performed twice to enrich inhibins, and deplete contaminating activin forms. The recovery and yield of Pro-inhibin preparations were determined by Western blot analysis (using R1 MAb), and inhibin ELISA, as described above.

Determination of Inhibin Bioactivity Using FSH In Vitro Bioassays

The ability of the inhibin preparations to suppress activin-induced FSH release was examined in cultured rat pituitary cells (Scott et al. (1980) *Endocrinology* 107:1536-1542), and in a mouse pituitary gonadotrope cell line (LβT2). For the rat pituitary culture bioassay, the anterior pituitary glands of adult male Sprague Dawley rats (12 weeks) were enzymatically dispersed with trypsin and plated at 50,000 cells/well in 48-well plates in DMEM-F12 (Invitrogen) containing 10% v/v fetal calf serum. After incubation at 37° C. in 5% v/v $CO_2$ for 48 hours, cells were washed with 0.1% BSA in DMEM-F12 and incubated for a further 4 hours. Cells were then treated with increasing doses of inhibins (5-800 pM) diluted in 0.1% w/v BSA in DMEM-F12 media. After 48 hours, the cell media were assayed for rat FSH by a specific rat FSH immunofluorometric assay (van Casteren et al. (2000) *Biol Reprod.* 62:886-894) using reagents provided from N.V. Organon, Oss, The Netherlands. The sensitivity of the in vitro bioassay was 75 pg/well using the highly purified 31-kDa inhibin A preparation (Makanji et al. (2007) supra).

For the LβT2 cell in vitro bioassay, cells were plated in 48-well plates at a density of $2.5 \times 10^5$ cells/well. The cells were allowed to recover for 24 hours in DMEM supplemented with 10% v/v FCS, and then treated with 150 pM activin A in the presence of increasing concentrations of inhibin (0.1-90 nM). Following a 24-hour incubation, the media was collected for FSH assay, as described above.

Smad Phosphorylation

The ability of Pro-inhibin to suppress activin-induced Smad2 phosphorylation, relative to mature inhibin, was determined in LβT2 cells. Cells were seeded at $2 \times 10^6$ cells/well in poly-lysine coated six-well plates. The following day, the media was changed to DMEM, 0.2% v/v FCS and 50 mM HEPES, containing 200 pM activin A with increasing concentrations of inhibins (0.3-3 nM). After 30 minutes of treatment, cells were washed with PBS and lysed in 100 μl RIPA buffer (50 mmol/l Tris-base, 1% v/v Nonidet P-40, 0.5% w/v deoxycholic acid, 0.1% w/v sodium dodecyl sulfate, and 0.9% w/v saline (pH 8.0)), containing protease inhibitor cocktail tablets (Roche Applied Sciences, Penzberg, Germany) and phosphatase inhibitors. Lysates were collected, clarified by centrifugation, and combined with reducing sample buffer (Life Technologies) and analyzed by Western blot. Phospho-Smad2 and Smad2 (Cell Signaling Technologies, Beverly, Mass.) antibodies were used at 1:2, 000 dilutions. Bound primary antibodies were detected using goat anti-rabbit or sheep anti-mouse horseradish peroxidise conjugates (GE Healthcare Life Sciences, Pittsburgh, Pa.). These studies were undertaken on duplicate cultures.

Introduction of Homodimerization Interface Mutations

This refers to Example 8. Sites of amino acids involved in homodimerization with $β_A$-subunit in $β_B$-subunit are provided in Tables 3 and 4, respectively. Particular examples include A347H and Y345G in $β_A$-subunit. These amino acid positions are based on the wild-type $β_A$-subunit sequence (S TABLE 5-continued Primer details for the construction of mutant inhibins

| Primer reference | Sequence 5'→3' | SEQ ID NO: |
|---|---|---|
| α-SCUT$_{(site1)}$-antisense | atctcatcgagaaagaaacgctcagtctcatcgactcccctgatgtcctggccttggtctccctct- | 26 |
| α-SCUT$_{(site2)}$-sense | ccctggagtcaggcggcgacgtcgaagacatgccc | 27 |
| α-SCUT$_{(site2)}$-antisense | gggcatgtcttcgacgtcgccgcctgactccaggg | 28 |
| α-polyHIStag-sense | atctcatcgagaaagaaacgctcagtctcatcaactcccctgatgtcctggccttggtctcc | 29 |
| α-polyHIStag-antisense | tgagactgagcgtttctttctcgatgagatgtgatgatggtggtgatggtgatgatgctccc | 30 |
| βA-XBAI-sense | ctagtctagaatgcccttgctttggctgagagg | 31 |
| βA-NOTI-antisense | gctagcggccgcctatgagcacccacactcctccacgatc | 32 |
| βA-SCUT$_{(site1)}$-sense | atctcatcgagaaagaaacgctcagtctcatcgggcttggagtgtgatggcaaggtcaacatctgc | 33 |
| βA-SCUT$_{(site1)}$-antisense | cgatgagactgagcgtttctttctcgatgagatattgagggtggtctcagactgccgggcctgcag | 34 |
| βA-M418A-sense | gacattcagaacgcgatcgtggaggag | 35 |
| βA-M418A-antisense | ctcctccacgatcgcgttctgaatgtc | 36 |

Example 1

Enhanced Processing of the α-Subunit Favors Inhibin Production Over Activin

The inhibin α- and β-subunits comprise an N-terminal prodomain and a C-terminal mature domain, separated by a proprotein convertase cleavage site (FIG. 1A). Following dimerization, the mature inhibin ligand is enzymatically released from its prodomain, enabling bioactivity. However, recombinant production of inhibin A indicates that processing by members of the proprotein convertase family is inefficient as significant amounts of unprocessed pro-inhibin A and full-length 50 kDa α-subunit are present in conditioned media, with relatively little mature 31-34 kDa inhibin A (FIG. 1B, lane 1). Further confounding inhibin production/purification are the high levels of mature activin A that are co-produced when HEK293T cells are transfected with wild-type α- and β-subunits (FIG. 1C, lane 1). To improve enzymatic processing of the α-subunit, the endogenous cleavage site ($^{229}$RARR$^{232}$) was replaced with an ideal proprotein convertase cleavage site ($^{229}$ISSRKKRSVS$^{238}$-SEQ ID NO:18) [FIG. 1A] and this "super-cut" variant was expressed in HEK293F cells. The super-cut form of the inhibin α-subunit resulted in a marked increase in the levels of bioactive inhibin A (FIG. 1B, lane 2) and a surprising decrease in mature activin A production (FIG. 1C, lane 2). Specific ELISAs identified similar changes in total inhibin and activin levels (FIGS. 1D and E).

Subsequently, the same enhanced cleavage site was introduced into the $β_A$-subunit and showed that in combination with the wild-type α-subunit this modification also increased mature inhibin A production (FIG. 1B, lane 3), although mature activin A levels were not altered (FIG. 1C, lane 3). Combining super-cut versions of both the α- and $β_A$-subunits led to nearly complete processing of precursor proteins and the greatest proportional ratio of inhibin:activin production (69:1) [Table 6]. These results support the concept that processing of the α-subunit is the limiting step in inhibin production, relative to activin.

TABLE 6

Ratio of inhibin:activin produced following transient transfection of HECK293F cells with wild-type and super-cut constructs

| α-subunit | βA-subunit | Ratio Inhibin:Activin (Mean ± SD) |
|---|---|---|
| WT | WT | 1.5 ± 0.7 |
| SCUT | WT | 24.8 ± 0.3 |
| WT | SCUT | 2.2 ± 0.3 |
| SCUT | SCUT | 68.7 ± 7.3 |

Example 2

Overexpressing the α-Subunit Greatly Increases Inhibin Production

Figure 6:
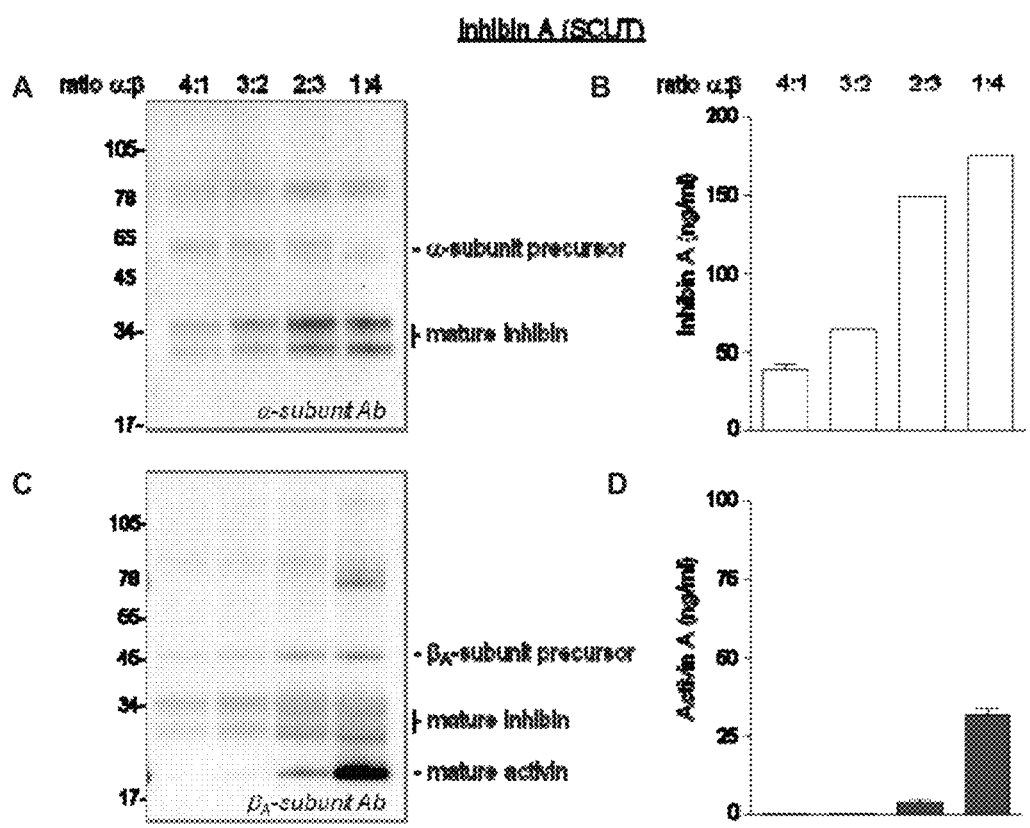

In initial experiments, HEK293T cells were transfected with an equal ratio of super-cut α- and $β_A$-subunit DNA. Varying this ratio (from 4:1 to 1:4) had interesting effects on inhibin and activin production (FIG. 6). At a 4:1 or 3:2 ratio of α:$β_A$-subunit, mature inhibin A levels were relatively high (FIGS. 6A and C), whereas mature activin A levels were negligible (FIGS. 6B and D). Interestingly, when the transfection ratio favored $β_A$-subunit expression (2:3 or 1:4 ratio of α:$β_A$-subunit) 3-4-fold higher levels of mature inhibin A were actually produced (FIGS. 6A and C). However, increased $β_A$-subunit expression was also accompanied by significant activin production (FIGS. 6B and D). Therefore, a 3:2 ratio of α:$β_A$-subunit was chosen for all future experiments.

Example 3

Figure 2:
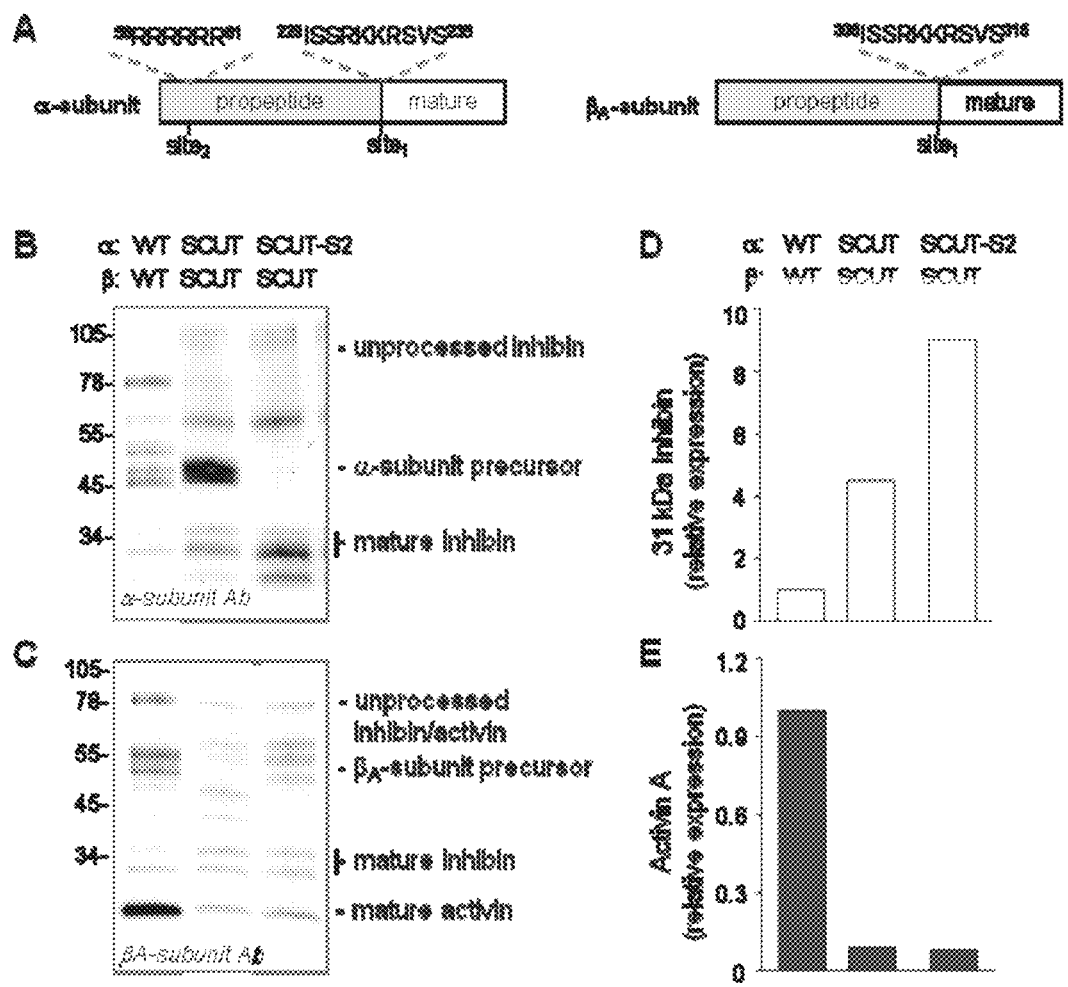

Modifying the Secondary Cleavage Site in the α-Subunit Further Enhances Inhibin A Production When large-scale production of inhibin A was commenced using the modified α- and $β_A$-subunit constructs, an increase in free 50 kDa α-subunit was noted (FIG. 2B) relative to the earlier small-scale transfections (FIG. 1B). The α-subunit precursor has a second cleavage site at the N-terminus (FIG. 2A), which is critical for inhibin production (Walton et al. (2015) *Endocrinology* 156:3047-3057). Here, this secondary cleavage site ($^{56}$RRLPRR$^{61}$-SEQ ID NO:46) was replaced with an improved proprotein convertase cleavage site ($^{56}$RRRRRR$^{61}$-SEQ ID NO:22) [FIG. 2A] and this super-cut-2 variant was expressed together with the modified $β_A$-subunit in HEK293T cells. Western analysis showed that these modifications abrogated expression of the free α-subunit and increased mature inhibin A expression (FIG. 2B, lane 3). Densitometry indicated that improving processing at both sites in the α-subunit increased mature inhibin production 9-fold relative to wild-type and 2-fold relative to the initial super-cut variant (FIG. 2D). Mature activin A levels were 12.5-fold lower than wild-type (FIGS. 2C and E). Thus, improving both processing sites in the α-subunit results in a significant increase in mature inhibin A production and a corresponding decrease in activin A. See also FIGS. 8 and 9.

Example 4

Figure 3:
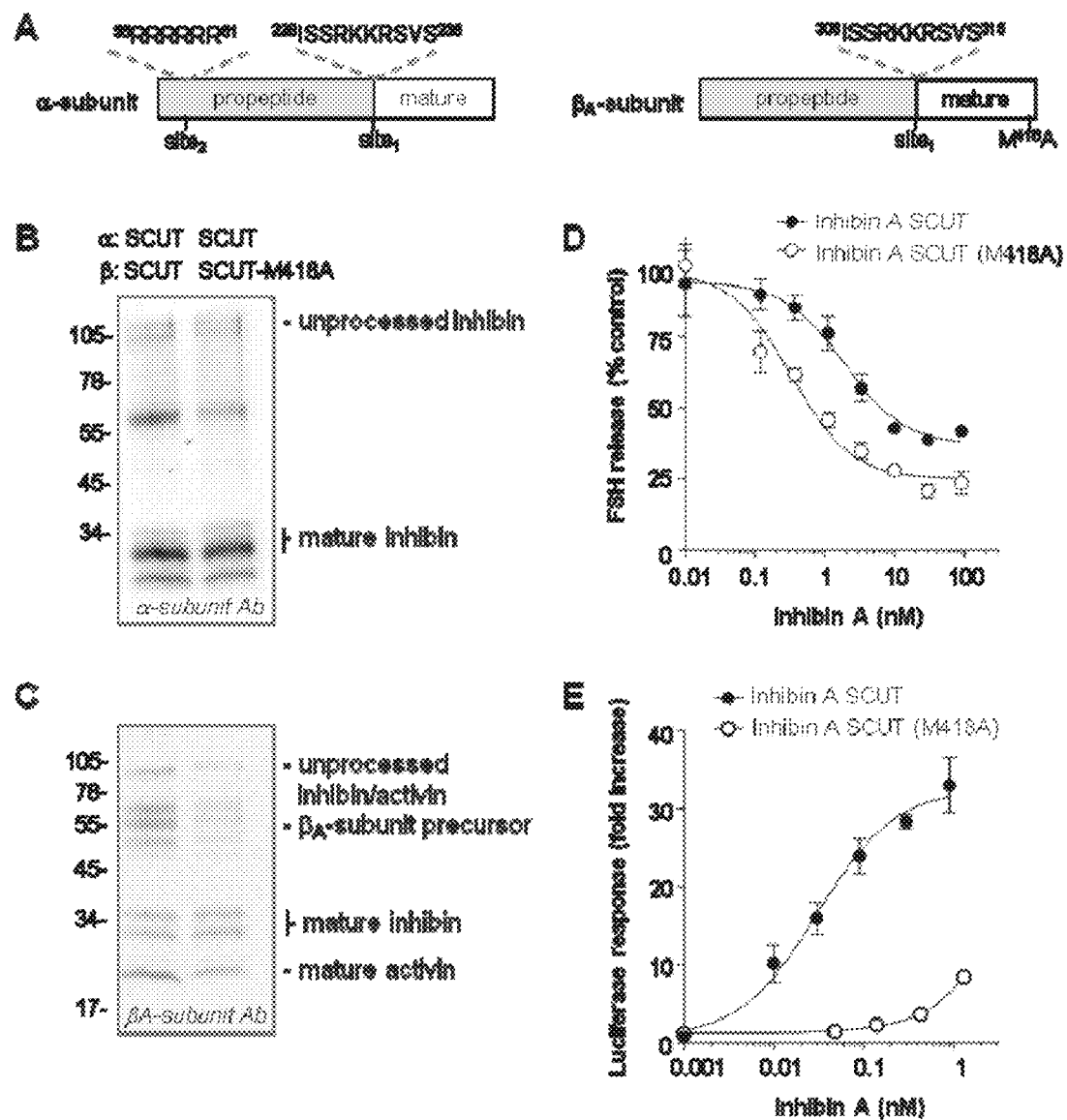

Elimination of Contaminating Activin Bioactivity by a Single Point Mutation in the $β_A$-Subunit By improving the processing capacity of the inhibin α-subunit and optimizing the transfection ratio of α:$β_A$-subunit DNA, inhibin production was greatly favored over that of related activins. However, any residual activin A produced would retain bioactivity and, therefore, have the potential to counteract inhibins' effects. To eliminate contaminating activin Bioactivity, a single point mutation (M418A) [the amino acid position is from the prodomain start site (SEQ ID NO:2), the equivalent site from start to the mature domain is M108A; the site is M432A in SEQ ID NO:4 and FIG. 7] was incorporated into the $β_A$-subunit at the type I receptor (ALK4) binding epitope (FIG. 3A) [Harrison et al. (2003) *J Biol Chem.* 278:21129-21135]. The M418A mutation did not affect the amounts of inhibin and activin produced by HEK293T cells (FIGS. 3B and C), however, it resulted in an 8-fold increase in inhibin activity, as measured by the suppression of activin-induced FSH release by LβT2 mouse gonadotrope cells (FIG. 3D). To demonstrate that this difference in activity was due to suppression of the residual activin response, HEK293F cells were transfected with an activin-responsive luciferase reporter and treated cells with the inhibin A preparations. This assay system is extremely sensitive to activin stimulation, but does not respond to inhibin due to low betaglycan expression. Inhibin A-SCUT induced a dose-dependent increase in luciferase activity, confirming the presence of active activin A in this preparation, whereas, inhibin A-SCUT (M418A) exhibited a 100-fold lower activin response (FIG. 3E). Thus, a single point mutation in the $β_A$-subunit (M418A) further increases inhibin A activity by inactivating the residual activin A produced. FIG. 7 provides the nucleotide and amino acid sequences of the human inhibin □$_A$-subunit super-cut variant with the ALK4 mutation.

Example 5

One-Step Purification of Mature Inhibin A

Figure 4:
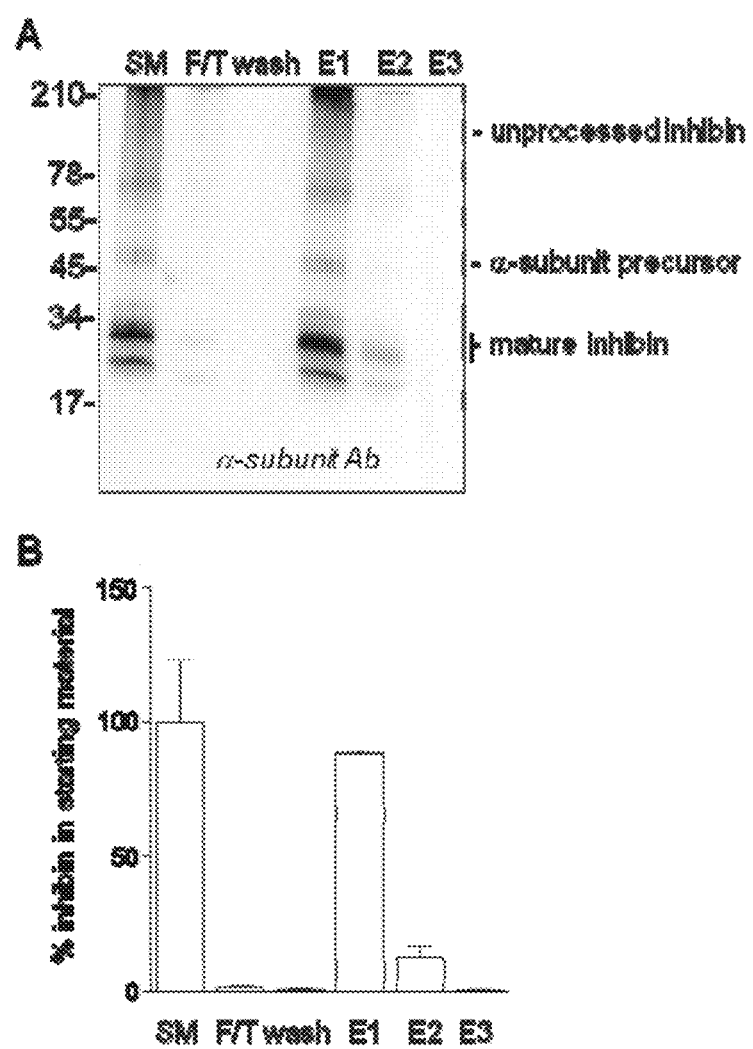

Studies have shown that mature TGF-β proteins are secreted from cells non-covalently associated with their prodomains (Harrison et al. (2011) *Growth Factors* 29:174-186; Sengle et al. (2008) *J Mol Biol.* 381:1025-1039; Sengle et al. (2011) *J Biol Chem.* 286:5087-5099). To determine if pro-inhibin A was secreted as a non-covalent complex, a HIS-tag was incorporated at the C-terminus of the α-subunit prodomain immediately preceding the super-cut-processing site. Conditioned media from HEK293T cells transfected with HIS-tagged super-cut α-subunit and super-cut $β_A$-subunit was purified by IMAC affinity chromatography and analyzed by Western blot. More than 90% of mature inhibin A present in the starting material was co-purified with the HIS-tagged prodomain (FIGS. 4A and B), confirming that the majority of inhibin A remains non-covalently associated with its prodomain upon secretion from the cell.

Example 6

Figure 5:
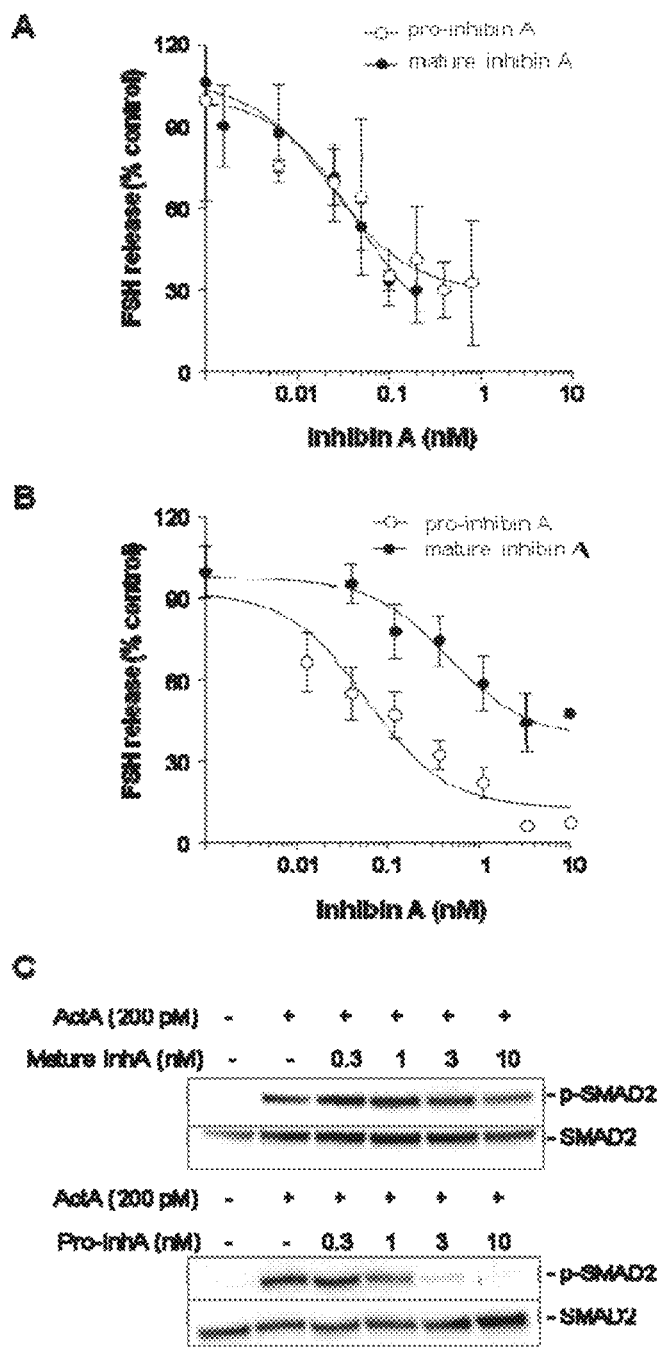

Pro-Inhibin A is a More Potent Activin Antagonist than Mature Inhibin A in Specific Settings Using FSH release assays in both primary rat pituitary cells and the LβT2 cell line, the biological activity of IMAC-purified pro-inhibin A and HPLC-purified mature inhibin A (Makanji et al. (2007) supra) were compared. In primary pituitary cells, pro-inhibin A induced a dose-dependent decrease in FSH release ($IC_{50}$ 75 pM), which was similar to that observed with mature inhibin A ($IC_{50}$ 65 pM) [FIG. 5A]. Any possible positive influence of the prodomain in this assay system may have been masked by the very potent activity of inhibin A. Therefore, the comparison of the pro- and mature inhibin isoforms was repeated on FSH release by LβT2 pituitary gonadotrope cells, which are significantly less responsive to inhibin due to low levels of betaglycan expression (Makanji et al. (2008) *J Biol Chem.* 283:16743-16751). Remarkably, pro-inhibin A ($IC_{50}$ 45 pM) was 22-fold more potent than mature inhibin A ($IC_{50}$ 1 nM) in this assay system (FIG. 5B). These differing activities were mirrored intracellularly where mature inhibin A only partially blocked activin-induced Smad2 phosphorylation, while pro-inhibin A completely inhibited this response (FIG. 5C). Together, these results indicate that in less responsive systems, inhibin A activity is significantly enhanced when non-covalently associated with its prodomain.

Example 7

Generation of Inhibin B Variants

Figure 11:
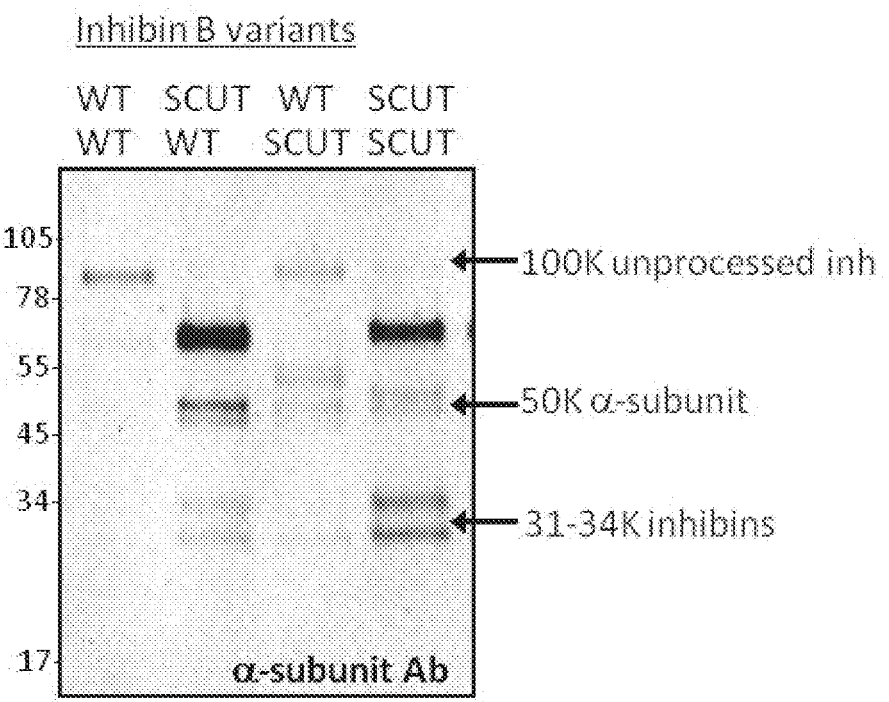

The same methods were applied to generate modified inhibin $β_B$-subunits and therefore, in conjunction with a modified α-subunit an inhibin B analog. The same super-cut and M→A substitution (M399A in SEQ ID NO:12 which is equivalent to M410A in SEQ ID NO:14) were included resulting in enhanced inhibin B production with reduced activin B co-production. The results are shown in FIG. 11. The amino acid sequence of mutated $β_B$-subunit is shown in FIG. 10. It should be noted that a Ser His Arg sequence was removed just prior to the super-cut site. FIG. 14 is the same sequence but with a modified signal nucleotide sequence. This does not result to any change to the amino acid sequence.

Example 8

Improvements in the Protocol to Produce Inhibins

In the previous Examples, a method is described to produce inter alia inhibins while limiting contaminating activin formation. Certain aspects have since been published by Walton et al. (2016) supra. In brief, the Examples showed inter alia that by improving processing of the inhibin α-subunits activin co-production can be minimized. Additionally, any residual activin activity is suppressed by modifying the type I receptor binding site on the $β_A$-subunit (M418A mutation).

In this Example, the procedure is further advanced using targeted mutagenesis. It is found that mutation of key residues in the β-subunit disrupted activin β/β-dimerization (homodimerization) at the binding interface without impacting inhibin α/β formation. This finding represents a significant advance for the generation of inhibins, and for progressing their development for clinical applications. Hence, one or more homodimerization interface are introduced to reduce or eliminate homodimerization and therefore active activin production. Sites on $β_A$-subunit involved in homodimerization are shown in Table 3. Particular examples are A347H and Y345G. Similar sites in $β_B$-subunit are listed in Table 4. The amino acid position is based on wild-type sequences (SEQ ID NO:2 for $β_A$-subunit and SEQ ID NO:12 for $β_B$-subunit).

Figure 12:
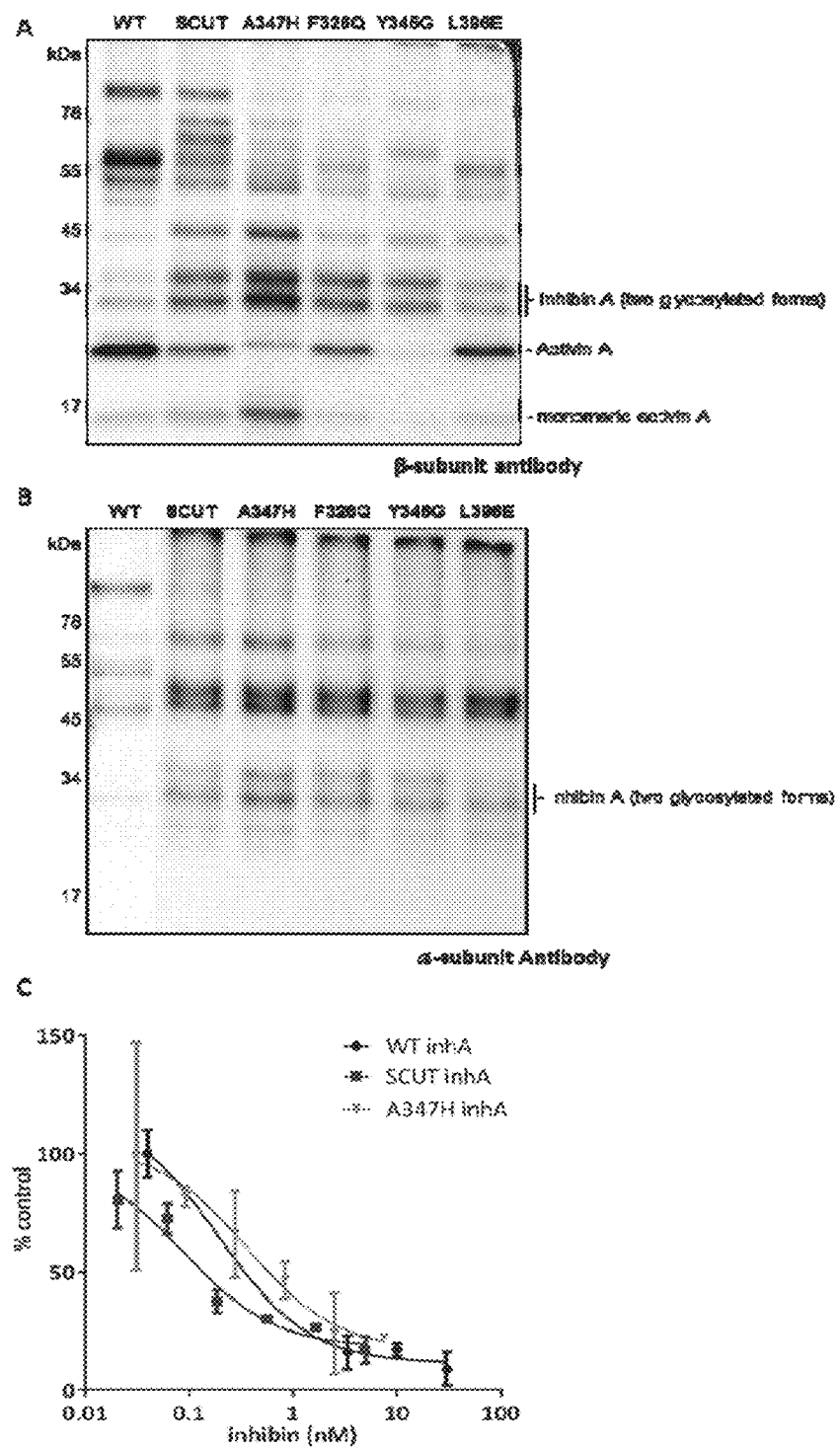

Using in vitro mutagenesis, residues are mutated in the inhibin $β_A$-subunit that lie in the predicted β/β homodimerization interface. Mutations were introduced into the inhibin supercut construct (which has heightened processing [Example 1]). The inhibin $β_A$-subunit variants were then co-transfected with the inhibin α-subunit (supercut form) into HEK293T mammalian cells, and the resultant inhibin/activin expression examined by Western blot and ELISAs. As seen in previous Examples (and reported in Walton et al. (2016) supra), enhanced processing of the inhibin subunits (supercut forms), resulted in an increased yield of mature inhibin relative to activin (compare lanes 1 and 2, FIG. 12A). Mutation of key residues in the $β_A$-subunit (e.g. A347H) disrupted activin formation—evidenced by decreased dimeric activin (FIG. 12A, lanes 3 and 5). The A347H and Y345G mutations appeared to be most disruptive for β/β-dimer formation, but did not limit inhibin synthesis (FIGS. 12A and B).

To ascertain that the newly generated inhibin mutants retained biological activity, the A347H mutant was purified following production in mammalian cells (as outlined in Walton et al. (2016) supra). The activity of this inhibin variant was then tested in a luciferase reporter assay—in which mammalian cells were first transfected with an activin-responsive luciferase reporter, and betaglycan (inhibin co-receptor), and then treated with activin A +/− inhibin A (A347H). The introduced A347H mutation did not hinder inhibin's ability to suppress activin-induced luciferase activity, as this variant had comparable activity to the unmodified inhibin form (FIG. 12C).

Figure 13:
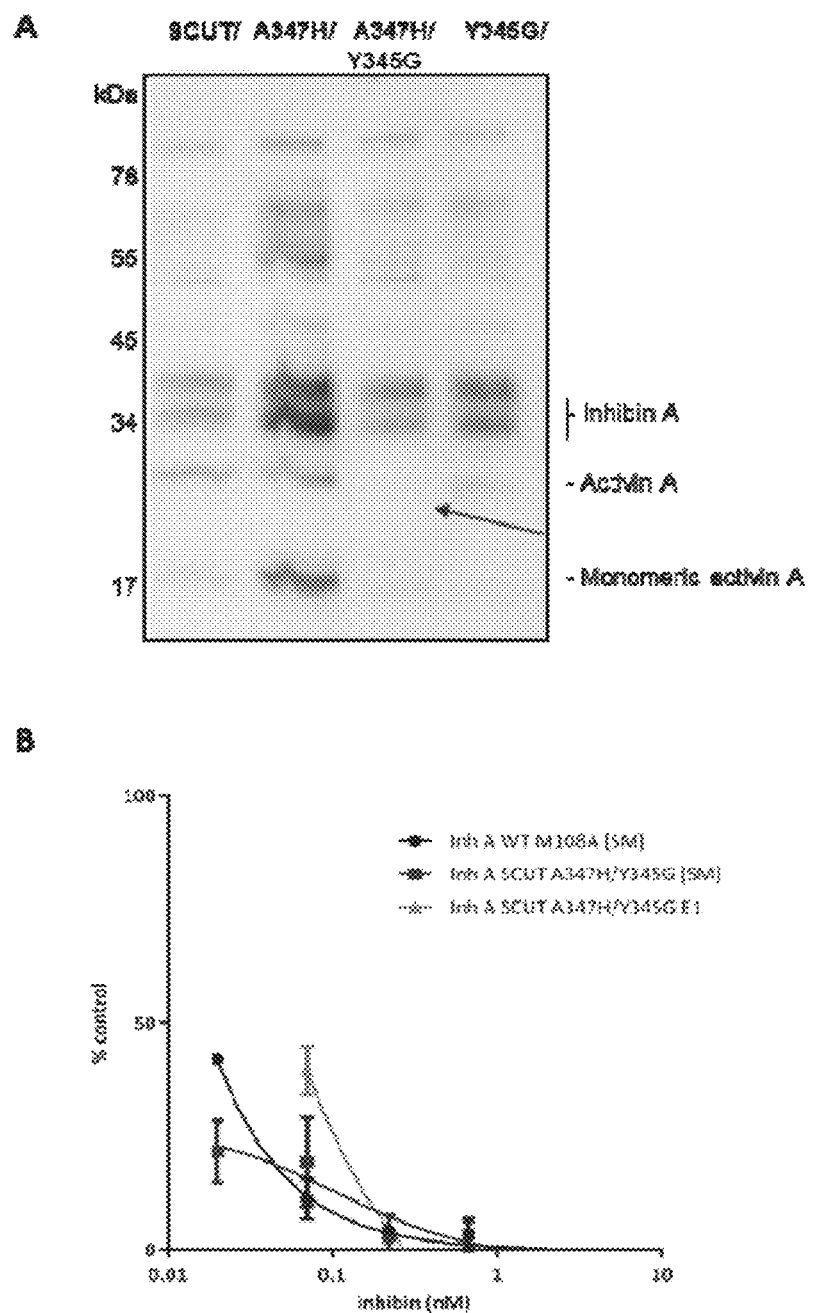

Next, the most promising inhibin mutants (A347H/Y345G), which exhibited disrupted activin formation. To this end, a double mutation A347H/Y345G was introduced into the $β_A$-subunit, and the resultant effect on ligand synthesis and activity examined (as described above). Co-introduction of the A347H/Y345G mutations into the inhibin $β_A$-subunit essentially abolished the production of activins—as determined using an antibody directed to the activin $β_A$-subunit (see arrow, FIG. 13A, lane 3). The dual mutation had no effect on inhibin production, relative to the supercut variant (compare lanes 1 and 3, FIG. 13A). Analysis indicates that Inhibin (A347H/Y345G) has comparable activity to wild type inhibin (FIG. 13B).

Hence, inhibin α- and $β_A$-subunits have been engineered to allow the production of inhibin in the absence of contaminating activin. Using a systematic approach, the approach has: (1) improved the processing of the inhibin precursor forms, resulting in higher proportions of mature active inhibins; (2) streamlined the purification process to allow the study of inhibins under native conditions; (3) disrupted homodimerization of the β-subunit, and consequently, enhanced inhibin α/β heterodimerization; and (4) inactivated any residual activin by silencing its receptor binding capacity. Together, these steps allow for the targeted production of bioactive inhibins, with yields superior to any process described to date.

These advances allow the full elucidation of the importance of inhibins in physiological processes, both within and outside the reproductive system, and provide a platform to generate recombinant inhibins for clinical applications.

Example 9

Therapeutic Potential of Inhibins

Inhibin A and B have the potential to be utilized therapeutically since declining levels of inhibin occur during menopause transition which not only correlated with an increase in FSH, but also a rapid decrease in bone mass (Perrien et al. (2006) supra; Perrien et al. (2007) supra). Subsequently, Perrien et al. (2007) supra used a transgenic approach to show that inhibin A acts as a potent stimulator of bone mass and strength, which could also prevent bone loss associated with gonadectomy. The anabolic effects of inhibin A have been confirmed in a murine model of distraction osteogenesis (Perrien et al. (2012) supra). The ability of inhibin A to enhance bone repair and regeneration is likely via antagonism of activin A, which potently inhibits osteoblast differentiation and matrix mineralization in vitro and in vivo (Lotinun et al. (2012) supra). This also applies to inhibin B. In support, blocking activin A signaling, using soluble ActRIIA, increases bone formation and improves skeletal integrity in both normal and ovariectomized mice (Chantry et al. (2010) *J Bone Min Res.* 25:2633-2646; Pearsall et al. (2008) *Proc Natl Acad Sci USA* 105:7082-7087). Although soluble ActRIIA cannot be used therapeutically because of off-target effects, restoring circulating inhibin levels in post-menopausal women is considered an attractive approach for the treatment of osteoporosis.

To date, the production and purification of inhibin in therapeutic amounts has proven difficult due to: (i) the inefficient processing of the heterodimeric precursor to the bioactive mature form; (ii) the short in vivo half-life of mature inhibin A (Makanji et al. (2009) supra); and (iii) the effort required to remove contaminating activins (Makanji et al. (2007) supra). To improve processing, in accordance with the present invention, the focus was on the inhibin α- and $β_A$-subunit prodomains. It is generally accepted within the TGF-β superfamily that prodomains govern the correct folding of dimeric precursors within the endoplasmic reticulum (Constam (2014) *Stem Cell Dev Biol.* 32:85-97). TGF-β precursors then acquire complex carbohydrate modifications during exocytosis, indicating transit through the trans-Golgi network. Once the correct tertiary structure is achieved, TGF-β precursors are proteolytically matured by proprotein convertases, either in a late Golgi compartment or extracellularly (Constam (2014) supra). For inhibin and activin, PC5/6 and furin have been identified as the processing enzymes (Antenos et al. (2011) *PloS one.* 6:e17348; Antenos et al. (2008) *J Biol Chem.* 283:33059-33068). However, the high levels of unprocessed inhibin and the low amounts of mature inhibin relative to activin, produced by HEK293T cells, suggested that a-subunit processing is less efficient than that of the $β_A$-subunit. Therefore, in order to generate inhibin A and B more efficiently the endogenous α-subunit cleavage site ($^{229}$RARR$^{232}$-SEQ ID NO:45) was replaced with an ideal proprotein convertase cleavage site ($^{229}$ISRKKRSVS$^{238}$-SEQ ID NO:18) [Duckert et al. (2004) supra]. As anticipated, this modification significantly increased the amount of mature inhibin produced by HEK293T cells; however, it also resulted in a dramatic decrease in activin production. As dimerization proceeds processing, this finding indicates that the "super-cut" site introduced into the α-subunit induced a conformational change, which greatly facilitated inhibin A production, relative to activin A.

Improved inhibin A production was accompanied by a substantial increase in the amount of α-subunit precursor. This 50 kDa species represents free α-subunit that has not dimerized with $β_A$-subunit and, therefore, has not been processed by proprotein convertases. Interestingly, the inhibin α-subunit is one of a small subset of TGF-β precursors that are cleaved at two distinct proprotein convertase motifs (Shi et al. (2011) Nature 474:343-349). The second cleavage site ($^{56}$RRLPRR$^{61}$) within the α-subunit precursor releases a 43 amino acid fragment that can limit inhibin activity (Walton et al. (2015) supra). Processing at site2 was absolutely required for the synthesis and secretion of inhibin A and B (Walton et al. (2015) supra). Incorporating enhanced proprotein convertase cleavage sites at both site1 and site2 of the α-subunit led to a 9-fold increase in mature inhibin A production, ostensibly due to complete dimerization and processing of the α-subunit. Remarkably, enhanced inhibin production was accompanied by a 12.5-fold decrease in activin A levels. Thus, by incorporating improved cleavage sites within the α- and $β_A$-subunits a regime to produce high levels of bioactive inhibin A has been developed. This also applies to inhibin B.

Although the modifications had greatly improved the ratio of inhibin A:activin A produced by HEK293F cells, the remaining activin retained biological activity. Therefore, a secondary mutation was incorporated within the $β_A$-subunit (M418A). Met$^{418}$ resides at the type I receptor (ALK4) interface of activin A and mutating this residue to alanine disrupts activin Activity without affecting binding to ActRIIA/IIB (Harrison et al. (2003) supra). In the context of inhibin, the M418A $β_A$-subunit mutation did not affect expression of the super-cut variant, but enhanced activity 8-fold. The improved activity was due to a nearly complete inactivation of residual activin A. Thus, inhibin A and inhibin B can be produced in the virtual absence of contaminating activin Activity, which has long been the major obstacle to the use of inhibin as a therapeutic.

A further modification incorporated into inhibin A was a HIS-tag at the C-terminus of the α-subunit prodomain. Mature inhibin A (M418A) was co-purified using HIS affinity chromatography, indicating that it is secreted by HEK293F cells in a non-covalent complex with its prodomain (termed pro-inhibin A). This brings the number of TGF-β proteins shown to remain associated with their prodomains extracellularly to 13 (Harrison et al. (2011) supra; Sengle et al. (2008) supra; Sengle et al. (2011) supra; Shi et al. (2011) supra; Mottershead et al. (2015) J Biol Chem 290:24007-24020; Robertson et al. (2015) Matrix Biol. 47:44-53), suggesting this is the default manner in which these proteins are secreted from cells. For most family members, prodomains localized mature growth factors in the vicinity of target cells; however, the affinity of the interaction is not sufficient to suppress biological activity (Harrison et al. (2011) supra; Sengle et al. (2011) supra). In contrast, the TGF-β isoforms, myostatin and GDF-11 bind their prodomains with high affinity and are secreted from the cell in a latent form (Shi et al. (2011) supra). Interestingly, it was found that pro-inhibin A was either equipotent (primary rat pituitary cells) or had enhanced activity (LβT2 pituitary gonadotrope cells) compared to HPLC-purified mature inhibin A. This is likely due to the prodomain facilitating inhibin A binding to its cell surface receptors, betaglycan and ActRIIA/B. In support, the prodomain of cumulin (BMP15:GDF9 heterodimer) was recently shown to be indispensable for this growth factors positive effects on oocyte quality (Mottershead et al. (2015) supra).

Yet another mutation disrupts the homodimerization interface site on the β subunits. For example, substitutions at amino acids 347 and 345 of $β_A$ resulted in virtually zero activin A activity. In an embodiment, the individual substitutions are A347H and Y345G. These may be used singularly (e.g. SEQ ID NOs:40 and 41) or in combination (e.g. SEQ ID NO:42). Functionally equivalent mutations can also be made in $β_B$. Other interface sites are listed in Tables 3 and 4.

Hence, introduction of a series of mutations into the α- and $β_A$-/$β_B$-subunits increase mature inhibin A/B expression, dramatically decreased and inactivated contaminating activin A/B and streamlined the purification process. It is now possible to generate sufficient quantities of recombinant inhibin A and inhibin B to fully explore the considerable therapeutic potential of this molecule on bone and other tissues.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

All patents, applications, publications, test methods, literature, and other materials cited herein are hereby incorporated by reference in their entirety as if physically present in this specification.

SEQUENCE LISTING

```
<160> NUMBER OF SEQ ID NOS: 44

<210> SEQ ID NO 1
<211> LENGTH: 1281
<212> TYPE: DNA
<213> ORGANISM: artificial
<220> FEATURE:
<223> OTHER INFORMATION: Nucleotide sequence encoding wild type human
      inhibin betaA-subunit

<400> SEQUENCE: 1
atgcccttgc tttggctgag aggatttctg ttggcaagtt gctggattat agtgaggagt      60
tcccccaccc caggatccga ggggcacagc gcggccccg actgtccgtc ctgtgcgctg     120
```

```
gccgccctcc caaaggatgt acccaactct cagccagaga tggtggaggc cgtcaagaag    180
cacattttaa acatgctgca cttgaagaag agacccgatg tcacccagcc ggtacccaag    240
gcggcgcttc tgaacgcgat cagaaagctt catgtgggca agtcgggga gaacgggtat     300 gtggagatag aggatgacat tggaaggagg cagaaatga atgaacttat ggagcagacc    360
tcggagatca tcacgtttgc cgagtcagga acagccagga agacgctgca cttcgagatt    420
tccaaggaag gcagtgacct gtcagtggtg gagcgtgcag aagtctggct cttcctaaaa    480
gtccccaagg ccaacaggac caggaccaaa gtcaccatcc gcctcttcca gcagcagaag    540
cacccgcagg gcagcttgga cacagggaa gaggccgagg aagtgggctt aaaggggag     600 aggagtgaac tgttgctctc tgaaaaagta gtagacgctc ggaagagcac ctggcatgtc    660
ttccctgtct ccagcagcat ccagcggttg ctggaccagg gcaagagctc cctggacgtt    720
cggattgcct gtgagcagtg ccaggagagt ggcgccagct tggttctcct gggcaagaag    780
aagaagaaag aagaggaggg ggaagggaaa aagaagggcg gaggtgaagg tggggcagga    840
gcagatgagg aaaaggagca gtcgcacaga cctttcctca tgctgcaggc ccggcagtct    900
gaagaccacc ctcatcgccg cgtcggcgg ggcttggagt gtgatggcaa ggtcaacatc     960
tgctgtaaga acagttctt tgtcagtttc aaggacatcg gctggaatga ctggatcatt    1020
gctccctctg gctatcatgc caactactgc gagggtgagt gcccgagcca tatagcaggc    1080
acgtccgggt cctcactgtc cttccactca acagtcatca accactaccg catgcggggc    1140
catagcccct tgccaacct caatcgtgc tgtgtgccca ccaagctgag acccatgtcc      1200
atgttgtact atgatgatgg tcaaaacatc atcaaaaagg acattcagaa catgatcgtg    1260
gaggagtgtg ggtgctcata g                                               1281
```

<210> SEQ ID NO 2
<211> LENGTH: 426
<212> TYPE: PRT
<213> ORGANISM: artificial
<220> FEATURE:
<223> OTHER INFORMATION: Amino acid sequence of wild type human inhibin
      betaA-subunit

<400> SEQUENCE: 2

```
Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140
```

```
Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Gly Glu Gly Lys Lys Lys
            260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His Ala Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
            405                 410                 415

Asn Met Ile Val Glu Glu Cys Gly Cys Ser
            420                 425
```

<210> SEQ ID NO 3
<211> LENGTH: 1323
<212> TYPE: DNA
<213> ORGANISM: artificial
<220> FEATURE:
<223> OTHER INFORMATION: Nucleotide sequence encoding super-cut variant
      of human inhibin betaA-subunit with FLAG tag

<400> SEQUENCE: 3

```
atgcccttgc tttggctgag aggatttctg ttggcaagtt gctggattat agtgaggagt      60
gactacaaag acgacgacga caaatccccc accccaggat ccgaggggca cagcgcggcc     120
cccgactgtc cgtcctgtgc gctggccgcc ctcccaaagg atgtacccaa ctctcagcca     180
gagatggtgg aggccgtcaa gaagcacatt ttaaacatgc tgcacttgaa gagagaccc      240 gatgtcaccc agccggtacc caaggcggcg cttctgaacg cgatcagaaa gcttcatgtg     300
ggcaaagtcg gggagaacgg gtatgtggag atagaggatg acattggaag gagggcagaa     360
atgaatgaac ttatggagca gacctcggag atcatcacgt tgccgagtc aggaacagcc      420
```

```
aggaagacgc tgcacttcga gatttccaag gaaggcagtg acctgtcagt ggtggagcgt      480
gcagaagtct ggctcttcct aaaagtcccc aaggccaaca ggaccaggac caaagtcacc      540
atccgcctct tccagcagca gaagcacccg cagggcagct ggacacaggg gaagaggcc       600 gaggaagtgg gcttaaaggg ggagaggagt gaactgttgc tctctgaaaa agtagtagac      660
gctcggaaga gcacctggca tgtcttccct gtctccagca gcatccagcg gttgctggac      720
cagggcaaga gctccctgga cgttcggatt gcctgtgagc agtgccagga gagtggcgcc      780
agcttggttc tcctgggcaa gaagaagaag aaagaagagg aggggaagg gaaaagaag        840 ggcggaggtg aaggtggggc aggagcagat gaggaaaagg agcagtcgca cagacctttc      900
ctcatgctgc aggcccggca gtctgaagac caccctcata tctcatcgag aaagaaacgc      960
tcagtctcat cgggcttgga gtgtgatggc aaggtcaaca tctgctgtaa gaaacagttc     1020
tttgtcagtt tcaaggacat cggctggaat gactggatca ttgctccctc tggctatcat     1080
gccaactact gcgagggtga gtgccccgagc catatagcag gcacgtccgg gtcctcactg     1140
tccttccact caacagtcat caaccactac cgcatgcggg gccatagccc ctttgccaac     1200
ctcaaatcgt gctgtgtgcc caccaagctg agacccatgt ccatgttgta ctatgatgat     1260
ggtcaaaaca tcatcaaaaa ggacattcag aacgcgatcg tggaggagtg tgggtgctca     1320
tag                                                                    1323
```

<210> SEQ ID NO 4
<211> LENGTH: 440
<212> TYPE: PRT
<213> ORGANISM: artificial
<220> FEATURE:
<223> OTHER INFORMATION: Amino acid sequence of super-cut variant of
      inhibin betaA-subunit with

```
Ser Leu Asp Thr Gly Glu Glu Ala Glu Val Gly Leu Lys Gly Glu
        195                 200                 205

Arg Ser Glu Leu Leu Ser Glu Lys Val Val Asp Ala Arg Lys Ser
    210                 215                 220

Thr Trp His Val Phe Pro Val Ser Ser Ile Gln Arg Leu Leu Asp
225                 230                 235                 240

Gln Gly Lys Ser Ser Leu Asp Val Arg Ile Ala Cys Glu Gln Cys
                245                 250                 255

Glu Ser Gly Ala Ser Leu Val Leu Leu Gly Lys Lys Lys Lys Glu
            260                 265                 270

Glu Glu Gly Glu Gly Lys Lys Gly Gly Glu Gly Gly Ala Gly
        275                 280                 285

Ala Asp Glu Glu Lys Glu Gln Ser His Arg Pro Phe Leu Met Leu Gln
    290                 295                 300

Ala Arg Gln Ser Glu Asp His Pro His Ile Ser Arg Lys Lys Arg
305                 310                 315                 320

Ser Val Ser Ser Gly Leu Glu Cys Asp Gly Lys Val Asn Ile Cys Cys
                325                 330                 335

Lys Lys Gln Phe Phe Val Ser Phe Lys Asp Ile Gly Trp Asn Asp Trp
            340                 345                 350

Ile Ile Ala Pro Ser Gly Tyr His Ala Asn Tyr Cys Glu Gly Glu Cys
        355                 360                 365

Pro Ser His Ile Ala Gly Thr Ser Gly Ser Ser Leu Ser Phe His Ser
370                 375                 380

Thr Val Ile Asn His Tyr Arg Met Arg Gly His Ser Pro Phe Ala Asn
385                 390                 395                 400

Leu Lys Ser Cys Cys Val Pro Thr Lys Leu Arg Pro Met Ser Met Leu
                405                 410                 415

Tyr Tyr Asp Asp Gly Gln Asn Ile Ile Lys Lys Asp Ile Gln Asn Ala
            420                 425                 430

Ile Val Glu Glu Cys Gly Cys Ser
        435                 440

<210> SEQ ID NO 5
<211> LENGTH: 1101
<212> TYPE: DNA
<213> ORGANISM: artificial
<220> FEATURE:
<223> OTHER INFORMATION: Nucleotide sequence encoding wild type human
      inhibin alpha-subunit

<400> SEQUENCE: 5
atggtgctgc acctactgct cttcttgctg ctgacccaca agggtgggca cagctgccag      60
gggctggagc tggcccggga acttgttctg gccaaggtga gggccctgtt cttggatgcc    120
ttggggcccc ccgcggtgac cagggaaggt ggggaccctg agtcaggcg gctgccccga     180 agacatgccc tggggggctt cacacacagg ggctctgagc ccgaggaaga ggaggatgtc    240
tcccaagcca tccttttccc agccacagat gccagctgtg aggacaagtc agctgccaga    300
gggctggccc aggaggctga ggagggcctc ttcagataca tgttccggcc atcccagcat    360
acacgcagcc gccaggtgac ttcagcccag ctgtggttcc acaccgggct ggacaggcag    420
ggcacagcag cctccaatag ctctgagccc ctgctaggcc tgctggcact gtcaccggga    480
ggacccgtgg ctgtgcccat gtctttgggc catgctcccc ctcactgggc cgtgctgcac    540
ctggccacct ctgctctctc tctgctgacc caccccgtcc tggtgctgct gctgcgctgt    600
```

```
cccctctgta cctgctcagc ccggcctgag gccacgccct tcctggtggc ccacactcgg    660
accagaccac ccagtggagg ggagagagcc cgacgctcaa ctcccctgat gtcctggcct    720
tggtctccct ctgctctgcg cctgctgcag aggcctccgg aggaaccggc tgcccatgcc    780
aactgccaca gagtagcact gaacatctcc ttccaggagc tgggctggga acggtggatc    840
gtgtaccctc ccagtttcat cttccactac tgtcatggtg gttgtgggct gcacatccca    900
ccaaacctgt cccttccagt ccctgggggct cccccctaccc cagcccagcc ctactccttg    960
ctgccagggg cccagccctg ctgtgctgct ctcccaggga ccatgaggcc cctacatgtc   1020
cgcaccacct cggatggagg ttactctttc aagtatgaga cagtgcccaa ccttctcacg   1080
cagcactgtg cttgtatcta a                                            1101
```

<210> SEQ ID NO 6
<211> LENGTH: 366
<212> TYPE: PRT
<213> ORGANISM: artificial
<220> FEATURE:
<223> OTHER INFORMATION: Amino acid sequence of wild type human inhibin alpha-subunit

<400> SEQUENCE: 6

```
Met Val Leu His Leu Leu Phe Leu Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Leu Pro Arg Arg His Ala Leu
    50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Glu Gly Leu Phe Arg
            100                 105                 110

Tyr Met Phe Arg Pro Ser Gln His Thr Arg Ser Arg Gln Val Thr Ser
        115                 120                 125

Ala Gln Leu Trp Phe His Thr Gly Leu Asp Arg Gln Gly Thr Ala Ala
    130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu Arg Ala Arg Arg Ser Thr Pro Leu Met Ser Trp Pro
225                 230                 235                 240

Trp Ser Pro Ser Ala Leu Arg Leu Leu Gln Arg Pro Pro Glu Glu Pro
                245                 250                 255

Ala Ala His Ala Asn Cys His Arg Val Ala Leu Asn Ile Ser Phe Gln
            260                 265                 270
```

```
Glu Leu Gly Trp Glu Arg Trp Ile Val Tyr Pro Pro Ser Phe Ile Phe
        275                 280                 285

His Tyr Cys His Gly Cys Gly Leu His Ile Pro Pro Asn Leu Ser
        290                 295                 300

Leu Pro Val Pro Gly Ala Pro Pro Thr Pro Ala Gln Pro Tyr Ser Leu
305                 310                 315                 320

Leu Pro Gly Ala Gln Pro Cys Cys Ala Ala Leu Pro Gly Thr Met Arg
                325                 330                 335

Pro Leu His Val Arg Thr Thr Ser Asp Gly Gly Tyr Ser Phe Lys Tyr
                340                 345                 350

Glu Thr Val Pro Asn Leu Leu Thr Gln His Cys Ala Cys Ile
        355                 360                 365

<210> SEQ ID NO 7
<211> LENGTH: 1146
<212> TYPE: DNA
<213> ORGANISM: artificial
<220> FEATURE:
<223> OTHER INFORMATION: Nucleotide sequence encoding super-cut variant
      1 of human inhibin alpha-subunit with HIS tag

<400> SEQUENCE: 7
atggtgctgc acctactgct cttcttgctg ctgaccccac agggtgggca cagctgccag    60
gggctggagc tgcccggga  acttgttctg gccaaggtga gggccctgtt cttggatgcc   120
ttggggcccc ccgcggtgac cagggaaggt ggggaccctg agtcaggcg  gctgccccga   180
agacatgccc tgggggggctt cacacacagg ggctctgagc ccgaggaaga ggaggatgtc   240
tcccaagcca tccttttccc agccacagat gccagctgtg aggacaagtc agctgccaga   300
gggctggccc aggaggctga ggagggcctc ttcagataca tgttccggcc atcccagcat   360
acacgcagcc gccaggtgac ttcagcccag ctgtggttcc acaccgggct ggacaggcag   420
ggcacagcag cctccaatag ctctgagccc tgctaggcc  tgctggcact gtcaccggga   480
ggacccgtgg ctgtgcccat gtctttgggc catgctcccc ctcactgggc cgtgctgcac   540
ctggccacct ctgctctctc tctgctgacc caccccgtcc tggtgctgct gctgcgctgt   600
cccctctgta cctgctcagc ccggcctgag gccacgccct tcctggtggc ccacactcgg   660
accagaccac ccagtggagg ggagcatcat caccatcacc accatcatca catctcatcg   720
agaaagaaac gctcagtctc atcaactccc ctgatgtcct ggccttggtc tccctctgct   780
ctgcgcctgc tgcagaggcc tccggaggaa ccggctgccc atgccaactg ccacagagta   840
gcactgaaca tctccttcca ggagctgggc tgggaacggt ggatcgtgta ccctcccagt   900
ttcatcttcc actactgtca tggtggttgt gggctgcaca tcccaccaaa cctgtccctt   960
ccagtccctg ggctcctcc  taccccagcc cagccctact ccttgctgcc aggggcccag  1020
ccctgctgtg ctgctctccc agggaccatg aggcccctac atgtccgcac cacctcggat  1080
ggaggttact ctttcaagta tgagacagtg cccaaccttc tcacgcagca ctgtgcttgt  1140
atctaa                                                             1146

<210> SEQ ID NO 8
<211> LENGTH: 381
<212> TYPE: PRT
<213> ORGANISM: artificial
<220> FEATURE:
<223> OTHER INFORMATION: Amino acid sequence of super-cut variant 1 of
      human inhibin alpha-subunit with HIS tag
```

<400> SEQUENCE: 8

```
Met Val Leu His Leu Leu Phe Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Leu Pro Arg Arg His Ala Leu
    50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Gly Leu Phe Arg
            100                 105                 110

Tyr Met Phe Arg Pro Ser Gln His Thr Arg Ser Arg Gln Val Thr Ser
        115                 120                 125

Ala Gln Leu Trp Phe His Thr Gly Leu Asp Arg Gln Gly Thr Ala Ala
    130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu His His His His His His His Ile Ser Ser
225                 230                 235                 240

Arg Lys Lys Arg Ser Val Ser Ser Thr Pro Leu Met Ser Trp Pro Trp
                245                 250                 255

Ser Pro Ser Ala Leu Arg Leu Leu Gln Arg Pro Glu Glu Pro Ala
            260                 265                 270

Ala His Ala Asn Cys His Arg Val Ala Leu Asn Ile Ser Phe Gln Glu
    275                 280                 285

Leu Gly Trp Glu Arg Trp Ile Val Tyr Pro Ser Phe Ile Phe His
    290                 295                 300

Tyr Cys His Gly Gly Cys Gly Leu His Ile Pro Pro Asn Leu Ser Leu
305                 310                 315                 320

Pro Val Pro Gly Ala Pro Pro Thr Pro Ala Gln Pro Tyr Ser Leu Leu
                325                 330                 335

Pro Gly Ala Gln Pro Cys Cys Ala Ala Leu Pro Gly Thr Met Arg Pro
            340                 345                 350

Leu His Val Arg Thr Thr Ser Asp Gly Gly Tyr Ser Phe Lys Tyr Glu
        355                 360                 365

Thr Val Pro Asn Leu Leu Thr Gln His Cys Ala Cys Ile
    370                 375                 380
```

<210> SEQ ID NO 9
<211> LENGTH: 1146
<212> TYPE: DNA
<213> ORGANISM: artificial

-continued

<220> FEATURE:
<223> OTHER INFORMATION: Nucleotide sequence encoding super-cut variant
2 of human inhibin alpha-subunit with HIS tag

<400> SEQUENCE: 9

```
atggtgctgc acctactgct cttcttgctg ctgaccccac agggtgggca cagctgccag        60
gggctggagc tggcccggga acttgttctg gccaaggtga gggccctgtt cttggatgcc       120
ttggggcccc ccgcggtgac cagggaaggt ggggaccctg agtcaggcg gcgacgtcga       180
agacatgccc tgggggggctt cacacacagg ggctctgagc ccgaggaaga ggaggatgtc       240
tcccaagcca tccttttccc agccacagat gccagctgtg aggacaagtc agctgccaga       300
gggctggccc aggaggctga ggagggcctc ttcagataca tgttccggcc atcccagcat       360
acacgcagcc gccaggtgac ttcagcccag ctgtggttcc acccgggct ggacaggcag        420
ggcacagcag cctccaatag ctctgagccc tgctaggcc tgctggcact gtcaccggga       480
ggacccgtgg ctgtgcccat gtctttgggc catgctcccc ctcactgggc cgtgctgcac       540
ctggccacct ctgctctctc tctgctgacc caccccgtcc tggtgctgct gctgcgctgt       600
cccctctgta cctgctcagc ccggcctgag gccacgccct tcctggtggc ccacactcgg       660
accagaccac ccagtggagg ggagcatcat caccatcacc accatcatca catctcatcg       720
agaaagaaac gctcagtctc atcaactccc ctgatgtcct ggccttggtc ccctctgct       780
ctgcgcctgc tgcagaggcc tccggaggaa ccggctgccc atgccaactg ccacagagta       840
gcactgaaca tctccttcca ggagctgggc tgggaacggt ggatcgtgta ccctcccagt       900
ttcatcttcc actactgtca tggtggttgt gggctgcaca tcccaccaaa cctgtccctt       960
ccagtccctg ggctcctcc taccccagcc cagccctact ccttgctgcc aggggcccag      1020
ccctgctgtg ctgctctccc agggaccatg aggcccctac atgtccgcac cacctcggat      1080
ggaggttact ctttcaagta tgagacagtg cccaaccttc tcacgcagca ctgtgcttgt      1140
atctaa                                                                1146
```

<210> SEQ ID NO 10
<211> LENGTH: 381
<212> TYPE: PRT
<213> ORGANISM: artificial
<220> FEATURE:
<223> OTHER INFORMATION: Amino acid sequence of super-cut variant 2 of
human inhibin alpha-subunit with HIS tag

<400> SEQUENCE: 10

Met Val Leu His Leu Leu Phe Leu Leu Thr Pro Gln Gly Gly
1               5                   10                  15

His Ser Cys Gln Gly Leu Glu Leu Ala Arg Glu Leu Val Leu Ala Lys
            20                  25                  30

Val Arg Ala Leu Phe Leu Asp Ala Leu Gly Pro Pro Ala Val Thr Arg
        35                  40                  45

Glu Gly Gly Asp Pro Gly Val Arg Arg Arg Arg Arg His Ala Leu
    50                  55                  60

Gly Gly Phe Thr His Arg Gly Ser Glu Pro Glu Glu Glu Asp Val
65                  70                  75                  80

Ser Gln Ala Ile Leu Phe Pro Ala Thr Asp Ala Ser Cys Glu Asp Lys
                85                  90                  95

Ser Ala Ala Arg Gly Leu Ala Gln Glu Ala Glu Glu Gly Leu Phe Arg
            100                 105                 110

Tyr Met Phe Arg Pro Ser Gln His Thr Arg Ser Arg Gln Val Thr Ser

```
                    115                 120                 125
Ala Gln Leu Trp Phe His Thr Gly Leu Asp Arg Gln Gly Thr Ala Ala
    130                 135                 140

Ser Asn Ser Ser Glu Pro Leu Leu Gly Leu Leu Ala Leu Ser Pro Gly
145                 150                 155                 160

Gly Pro Val Ala Val Pro Met Ser Leu Gly His Ala Pro Pro His Trp
                165                 170                 175

Ala Val Leu His Leu Ala Thr Ser Ala Leu Ser Leu Leu Thr His Pro
            180                 185                 190

Val Leu Val Leu Leu Leu Arg Cys Pro Leu Cys Thr Cys Ser Ala Arg
        195                 200                 205

Pro Glu Ala Thr Pro Phe Leu Val Ala His Thr Arg Thr Arg Pro Pro
    210                 215                 220

Ser Gly Gly Glu His His His His His His His His Ile Ser Ser
225                 230                 235                 240

Arg Lys Lys Arg Ser Val Ser Ser Thr Pro Leu Met Ser Trp Pro Trp
                245                 250                 255

Ser Pro Ser Ala Leu Arg Leu Leu Gln Arg Pro Pro Glu Glu Pro Ala
            260                 265                 270

Ala His Ala Asn Cys His Arg Val Ala Leu Asn Ile Ser Phe Gln Glu
        275                 280                 285

Leu Gly Trp Glu Arg Trp Ile Val Tyr Pro Pro Ser Phe Ile Phe His
    290                 295                 300

Tyr Cys His Gly Gly Cys Gly Leu His Ile Pro Pro Asn Leu Ser Leu
305                 310                 315                 320

Pro Val Pro Gly Ala Pro Pro Thr Pro Ala Gln Pro Tyr Ser Leu Leu
                325                 330                 335

Pro Gly Ala Gln Pro Cys Cys Ala Ala Leu Pro Gly Thr Met Arg Pro
            340                 345                 350

Leu His Val Arg Thr Thr Ser Asp Gly Gly Tyr Ser Phe Lys Tyr Glu
        355                 360                 365

Thr Val Pro Asn Leu Leu Thr Gln His Cys Ala Cys Ile
    370                 375                 380

<210> SEQ ID NO 11
<211> LENGTH: 1884
<212> TYPE: DNA
<213> ORGANISM: artificial
<220> FEATURE:
<223> OTHER INFORMATION: Nucleotide sequence encoding wild type human
      inhibin betaB-subunit

<400> SEQUENCE: 11
atggacgggc tgcccggtcg ggcgctgggg gccgcctgcc ttctgctgct ggcggccggc    60
tggctggggc ctgaggcctg ggctcaccc acgccccgc cgacgcctgc cgcgccgccg    120
ccacccccgc cacccggatc cccgggtggc tcgcaggaca cctgtacgtc gtgcggcggc    180
ttccggcggc cagaggagct cggccgagtg gacggcgact tcctggaggc ggtgaagcgg    240
cacatcttga ccgcctgca gatgcggggc cggcccaaca tcacgcacgc cgtgcctaag    300
gccgccatgg tcacggccct gcgcaagctg cacgcgggca aggtgcgcga ggacggccgc    360
gtggagatcc gcacctcga cggccacgcc agcccgggcg ccgacggcca ggagcgcgtt    420
tccgaaatca tcagcttcgc cgagacagat ggcctcgcct cctcccgggt ccgcctatac    480
ttcttcatct ccaacgaagg caaccagaac ctgtttgtgg tccaggccag cctgtggctt    540
```

```
tacctgaaac tcctgccta cgtcctggag aagggcagcc ggcggaaggt gcgggtcaaa      600
gtgtacttcc aggagcaggg ccacggtgac aggtggaaca tggtggagaa gagggtggac      660
atggacgggc tgcccggtcg ggcgctgggg gccgcctgcc ttctgctgct ggcggccggc      720
tggctggggc ctgaggcctg ggctcacccc acgccccgc cgacgcctgc cgcgccgccg      780
ccacccccgc cacccggatc cccgggtggc tcgcaggaca cctgtacgtc gtgcggcggc      840
ttccggcggc cagaggagct cggccgagtg gacggcgact tcctggaggc ggtgaagcgg      900
cacatcttga gccgcctgca gatgcgggc cggcccaaca tcacgcacgc cgtgcctaag      960
gccgccatgg tcacggccct gcgcaagctg cacgcgggca aggtgcgcga ggacggccgc     1020
gtggagatcc cgcacctcga cggccacgcc agcccgggcg ccgacggcca ggagcgcgtt     1080
tccgaaatca tcagcttcgc cgagacagat ggcctcgcct cctcccgggt ccgcctatac     1140
ttcttcatct ccaacgaagg caaccagaac ctgtttgtgg tccaggccag cctgtggctt     1200
tacctgaaac tcctgccta cgtcctggag aagggcagcc ggcggaaggt gcgggtcaaa     1260
gtgtacttcc aggagcaggg ccacggtgac aggtggaaca tggtggagaa gagggtggac     1320
ctcaagcgca gcggctggca taccttccca ctcacggagg ccatccaggc cttgtttgag     1380
cggggcgagc ggcgactcaa cctagacgtg cagtgtgaca ctgccagga gctggccgtg     1440 gtgccggtgt tcgtggaccc aggcgaagag tcgcaccggc cctttgtggt ggtgcaggct     1500
cggctgggcg acagcaggca ccgcattcgc aagcgaggcc tggagtgcga tggccggacc     1560
aacctctgtt gcaggcaaca gttcttcatt gacttccgcc tcatcggctg aacgactgg     1620 atcatagcac ccaccggcta ctacgggaac tactgtgagg gcagctgccc agcctacctg     1680 gcagggtcc ccggctctgc ctcctccttc cacacggctg tggtgaacca gtaccgcatg     1740
cggggtctga accccggcac ggtgaactcc tgctgcattc ccaccaagct gagcaccatg     1800
tccatgctgt acttcgatga tgagtacaac atcgtcaagc gggacgtgcc caacatgatt     1860
gtggaggagt gcggctgcgc ctga                                            1884
```

<210> SEQ ID NO 12
<211> LENGTH: 407
<212> TYPE: PRT
<213> ORGANISM: artificial
<220> FEATURE:
<223> OTHER INFORMATION: Amino acid sequence of wild type human inhibin betaB-subunit

<400> SEQUENCE: 12

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Ser Pro Thr Pro
                20                  25                  30

Pro Pro Thr Pro Ala Ala Pro Pro Pro Pro Pro Pro Gly Ser Pro
        35                  40                  45

Gly Gly Ser Gln Asp Thr Cys Thr Ser Cys Gly Gly Phe Arg Arg Pro
    50                  55                  60

Glu Glu Leu Gly Arg Val Asp Gly Asp Phe Leu Glu Ala Val Lys Arg
65                  70                  75                  80

His Ile Leu Ser Arg Leu Gln Met Arg Gly Arg Pro Asn Ile Thr His
                85                  90                  95

Ala Val Pro Lys Ala Ala Met Val Thr Ala Leu Arg Lys Leu His Ala
            100                 105                 110

Gly Lys Val Arg Glu Asp Gly Arg Val Glu Ile Pro His Leu Asp Gly

His Ala Ser Pro Gly Ala Asp Gly Gln Glu Arg Val Ser Glu Ile Ile
130                 135                 140
Ser Phe Ala Glu Thr Asp Gly Leu Ala Ser Ser Arg Val Arg Leu Tyr
145                 150                 155                 160
Phe Phe Ile Ser Asn Glu Gly Asn Gln Asn Leu Phe Val Val Gln Ala
                165                 170                 175
Ser Leu Trp Leu Tyr Leu Lys Leu Leu Pro Tyr Val Leu Glu Lys Gly
            180                 185                 190
Ser Arg Arg Lys Val Arg Val Lys Val Tyr Phe Gln Glu Gln Gly His
        195                 200                 205
Gly Asp Arg Trp Asn Met Val Glu Lys Arg Val Asp Leu Lys Arg Ser
210                 215                 220
Gly Trp His Thr Phe Pro Leu Thr Glu Ala Ile Gln Ala Leu Phe Glu
225                 230                 235                 240
Arg Gly Glu Arg Arg Leu Asn Leu Asp Val Gln Cys Asp Ser Cys Gln
                245                 250                 255
Glu Leu Ala Val Val Pro Val Phe Val Asp Pro Gly Glu Glu Ser His
            260                 265                 270
Arg Pro Phe Val Val Val Gln Ala Arg Leu Gly Asp Ser Arg His Arg
        275                 280                 285
Ile Arg Lys Arg Gly Leu Glu Cys Asp Gly Arg Thr Asn Leu Cys Cys
290                 295                 300
Arg Gln Gln Phe Phe Ile Asp Phe Arg Leu Ile Gly Trp Asn Asp Trp
305                 310                 315                 320
Ile Ile Ala Pro Thr Gly Tyr Tyr Gly Asn Tyr Cys Glu Gly Ser Cys
                325                 330                 335
Pro Ala Tyr Leu Ala Gly Val Pro Gly Ser Ala Ser Ser Phe His Thr
            340                 345                 350
Ala Val Val Asn Gln Tyr Arg Met Arg Gly Leu Asn Pro Gly Thr Val
        355                 360                 365
Asn Ser Cys Cys Ile Pro Thr Lys Leu Ser Thr Met Ser Met Leu Tyr
370                 375                 380
Phe Asp Asp Glu Tyr Asn Ile Val Lys Arg Asp Val Pro Asn Met Ile
385                 390                 395                 400
Val Glu Glu Cys Gly Cys Ala
            405

<210> SEQ ID NO 13
<211> LENGTH: 1257
<212> TYPE: DNA
<213> ORGANISM: artificial
<220> FEATURE:
<223> OTHER INFORMATION: Nucleotide sequence encoding super-cut variant
      of human inhibin betaB-subunit with FLAG tag

<400> SEQUENCE: 13
atggacgggc tgcccggtcg ggcgctgggg ccgcctgcc ttctgctgct ggcggccggc     60 tggctgggc ctgaggcctg gggcgactac aaagacgacg acgacaaatc acccacgccc    120
ccgccgacgc ctgccgcgcc gccgccaccc ccgccaccg atccccggg tggctcgcag    180 gacacctgta cgtcgtgcgg cggcttccgg cggccagagg agctcggccg agtggacggc    240
gacttcctgg aggcggtgaa gcggcacatc ttgagccgcc tgcagatgcg gggccggccc    300
aacatcacgc acgccgtgcc taaggccgcc atggtcacgg ccctgcgcaa gctgcacgcg    360

```
ggcaaggtgc gcgaggacgg ccgcgtggag atcccgcacc tcgacggcca cgccagcccg    420
ggcgccgacg gccaggagcg cgtttccgaa atcatcagct cgccgagac agatggcctc     480 gcctcctccc gggtccgcct atacttcttc atctccaacg aaggcaacca gaacctgttt    540
gtggtccagg ccagcctgtg gctttacctg aaactcctgc cctacgtcct ggagaagggc    600
agccggcgga aggtgcgggt caaagtgtac ttccaggagc agggccacgg tgacaggtgg    660
aacatggtgg agaagagggt ggacctcaag cgcagcggct ggcataccct cccactcacg    720
gaggccatcc aggccttgtt tgagcggggc gagcggcgac tcaacctaga cgtgcagtgt    780
gacagctgcc aggagctggc cgtggtgccg gtgttcgtgg acccaggcga agagtcgcac    840
cggccctttg tggtggtgca ggctcggctg ggcgacatct catcgagaaa gaaacgctca    900
gtctcatcgg gcctggagtg cgatggccgg accaacctct gttgcaggca acagttcttc    960
attgacttcc gcctcatcgg ctggaacgac tggatcatag cacccaccgg ctactacggg   1020
aactactgtg agggcagctg cccagcctac ctggcagggg tccccggctc tgcctcctcc   1080
ttccacacgg ctgtggtgaa ccagtaccgc atgcggggtc tgaaccccgg cacggtgaac   1140
tcctgctgca ttcccaccaa gctgagcacc atgtccatgc tgtacttcga tgatgagtac   1200
aacatcgtca gcgggacgt gcccaacgcg attgtggagg agtgcggctg cgcctga       1257
```

<210> SEQ ID NO 14
<211> LENGTH: 418
<212> TYPE: PRT
<213> ORGANISM: artificial
<220> FEATURE:
<223> OTHER INFORMATION: Amino acid sequence of super-cut variant of human inhibin betaB-subunit with FLAG tag

<400> SEQUENCE: 14

```
Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Asp Tyr Lys Asp
                20                  25                  30

Asp Asp Asp Lys Ser Pro Thr Pro Pro Thr Pro Ala Ala Pro Pro
            35                  40                  45

Pro Pro Pro Pro Gly Ser Pro Gly Gly Ser Gln Asp Thr Cys Thr
        50                  55                  60

Ser Cys Gly Gly Phe Arg Arg Pro Glu Glu Leu Gly Arg Val Asp Gly
65                  70                  75                  80

Asp Phe Leu Glu Ala Val Lys Arg His Ile Leu Ser Arg Leu Gln Met
                85                  90                  95

Arg Gly Arg Pro Asn Ile Thr His Ala Val Pro Lys Ala Ala Met Val
            100                 105                 110

Thr Ala Leu Arg Lys Leu His Ala Gly Lys Val Arg Glu Asp Gly Arg
        115                 120                 125

Val Glu Ile Pro His Leu Asp Gly His Ala Ser Pro Gly Ala Asp Gly
    130                 135                 140

Gln Glu Arg Val Ser Glu Ile Ile Ser Phe Ala Glu Thr Asp Gly Leu
145                 150                 155                 160

Ala Ser Ser Arg Val Arg Leu Tyr Phe Phe Ile Ser Asn Glu Gly Asn
                165                 170                 175

Gln Asn Leu Phe Val Val Gln Ala Ser Leu Trp Leu Tyr Leu Lys Leu
            180                 185                 190

Leu Pro Tyr Val Leu Glu Lys Gly Ser Arg Arg Lys Val Arg Val Lys
        195                 200                 205
```

Val Tyr Phe Gln Glu Gln Gly His Gly Asp Arg Trp Asn Met Val Glu
    210                 215                 220

Lys Arg Val Asp Leu Lys Arg Ser Gly Trp His Thr Phe Pro Leu Thr
225                 230                 235                 240

Glu Ala Ile Gln Ala Leu Phe Glu Arg Gly Glu Arg Arg Leu Asn Leu
                245                 250                 255

Asp Val Gln Cys Asp Ser Cys Gln Glu Leu Ala Val Val Pro Val Phe
            260                 265                 270

Val Asp Pro Gly Glu Glu Ser His Arg Pro Phe Val Val Gln Ala
        275                 280                 285

Arg Leu Gly Asp Ile Ser Ser Arg Lys Lys Arg Ser Val Ser Ser Gly
    290                 295                 300

Leu Glu Cys Asp Gly Arg Thr Asn Leu Cys Cys Arg Gln Gln Phe Phe
305                 310                 315                 320

Ile Asp Phe Arg Leu Ile Gly Trp Asn Asp Trp Ile Ile Ala Pro Thr
                325                 330                 335

Gly Tyr Tyr Gly Asn Tyr Cys Glu Gly Ser Cys Pro Ala Tyr Leu Ala
            340                 345                 350

Gly Val Pro Gly Ser Ala Ser Ser Phe His Thr Ala Val Val Asn Gln
        355                 360                 365

Tyr Arg Met Arg Gly Leu Asn Pro Gly Thr Val Asn Ser Cys Cys Ile
    370                 375                 380

Pro Thr Lys Leu Ser Thr Met Ser Met Leu Tyr Phe Asp Asp Glu Tyr
385                 390                 395                 400

Asn Ile Val Lys Arg Asp Val Pro Asn Ala Ile Val Glu Glu Cys Gly
                405                 410                 415

Cys Ala

<210> SEQ ID NO 15
<211> LENGTH: 24
<212> TYPE: DNA
<213> ORGANISM: artificial
<220> FEATURE:
<223> OTHER INFORMATION: Nucleotide sequence encoding FLAG tag

<400> SEQUENCE: 15
gactacaaag acgacgacga caaa                                           24

<210> SEQ ID NO 16
<211> LENGTH: 8
<212> TYPE: PRT
<213> ORGANISM: artificial
<220> FEATURE:
<223> OTHER INFORMATION: Amino acid sequence of FLAG tag

<400> SEQUENCE: 16

Asp Tyr Lys Asp Asp Asp Asp Lys
1               5

<210> SEQ ID NO 17
<211> LENGTH: 33
<212> TYPE: DNA
<213> ORGANISM: artificial
<220> FEATURE:
<223> OTHER INFORMATION: Nucleotide sequence encoding super-cut site

<400> SEQUENCE: 17
atctcatcga gaaagaaacg ctcagtctca tcg                                 33

<210> SEQ ID NO 18
<211> LENGTH: 11
<212> TYPE: PRT
<213> ORGANISM: artificial
<220> FEATURE:
<223> OTHER INFORMATION: Amino acid sequence of super-cut site

<400> SEQUENCE: 18

Ile Ser Ser Arg Lys Lys Arg Ser Val Ser Ser
1               5                   10

<210> SEQ ID NO 19
<211> LENGTH: 26
<212> TYPE: DNA
<213> ORGANISM: artificial
<220> FEATURE:
<223> OTHER INFORMATION: Nucleotide sequence encoding poly-histidine TAG
      (x9)

<400> SEQUENCE: 19
atcatcacca tcaccaccat catcac                                          26

<210> SEQ ID NO 20
<211> LENGTH: 9
<212> TYPE: PRT
<213> ORGANISM: artificial
<220> FEATURE:
<223> OTHER INFORMATION: Amino acid sequence of poly-histidine TAG (x9)

<400> SEQUENCE: 20

His His His His His His His His His
1               5

<210> SEQ ID NO 21
<211> LENGTH: 15
<212> TYPE: DNA
<213> ORGANISM: artificial
<220> FEATURE:
<223> OTHER INFORMATION: Nucleotide sequence encoding super-cut site 2

<400> SEQUENCE: 21
aggcggcgac gtcga                                                      15

<210> SEQ ID NO 22
<211> LENGTH: 5
<212> TYPE: PRT
<213> ORGANISM: artificial
<220> FEATURE:
<223> OTHER INFORMATION: Amino acid sequence of super-cut site 2

<400> SEQUENCE: 22

Arg Arg Arg Arg Arg
1               5

<210> SEQ ID NO 23
<211> LENGTH: 34
<212> TYPE: DNA
<213> ORGANISM: artificial
<220> FEATURE:
<223> OTHER INFORMATION: Nucleotide sequence of  alpha-NHE1 sense primer

<400> SEQUENCE: 23
ctaggctagc atggtgctgc acctactgct cttc                                 34

<210> SEQ ID NO 24
<211> LENGTH: 33

```
<212> TYPE: DNA
<213> ORGANISM: artificial
<220> FEATURE:
<223> OTHER INFORMATION: Nucleotide sequence of alpha-ECOR1 antisense
      primer

<400> SEQUENCE: 24
ctaggaattc ttagatacaa gcacagtgct gcg                                    33

<210> SEQ ID NO 25
<211> LENGTH: 66
<212> TYPE: DNA
<213> ORGANISM: artificial
<220> FEATURE:
<223> OTHER INFORMATION: Nucleotide sequence of alpha-SCUT (site1)
      sense primer

<400> SEQUENCE: 25
cgatgagact gagcgtttct ttctcgatga gatctcccct ccactgggtg gtctggtccg       60
agtgtg                                                                 66

<210> SEQ ID NO 26
<211> LENGTH: 66
<212> TYPE: DNA
<213> ORGANISM: artificial
<220> FEATURE:
<223> OTHER INFORMATION: Nucleotide sequence of alpha-SCUT (site1)
      antisense primer

<400> SEQUENCE: 26
atctcatcga gaaagaaacg ctcagtctca tcgactcccc tgatgtcctg gccttggtct       60
ccctct                                                                 66

<210> SEQ ID NO 27
<211> LENGTH: 35
<212> TYPE: DNA
<213> ORGANISM: artificial
<220> FEATURE:
<223> OTHER INFORMATION: Nucleotide sequence of alpha-SCUT (site2)
      sense primer

<400> SEQUENCE: 27
ccctggagtc aggcggcgac gtcgaagaca tgccc                                  35

<210> SEQ ID NO 28
<211> LENGTH: 35
<212> TYPE: DNA
<213> ORGANISM: artificial
<220> FEATURE:
<223> OTHER INFORMATION: Nucleotide sequence of alpha-SCUT (site2)
      antisense primer

<400> SEQUENCE: 28
gggcatgtct tcgacgtcgc cgcctgactc caggg                                  35

<210> SEQ ID NO 29
<211> LENGTH: 62
<212> TYPE: DNA
<213> ORGANISM: artificial
<220> FEATURE:
<223> OTHER INFORMATION: Nucleotide sequence of alpha-polyH1 Stag
      sense primer

<400> SEQUENCE: 29
atctcatcga gaaagaaacg ctcagtctca tcaactcccc tgatgtcctg gccttggtct       60
```

```
cc                                                              62
```

<210> SEQ ID NO 30
<211> LENGTH: 62
<212> TYPE: DNA
<213> ORGANISM: artificial
<220> FEATURE:
<223> OTHER INFORMATION: Nucleotide sequence of alpha-polyH1 Stage
      antisense primer

<400> SEQUENCE: 30

```
tgagactgag cgtttctttc tcgatgagat gtgatgatgg tggtgatggt gatgatgctc   60
cc                                                                  62
```

<210> SEQ ID NO 31
<211> LENGTH: 33
<212> TYPE: DNA
<213> ORGANISM: artificial
<220> FEATURE:
<223> OTHER INFORMATION: Nucleotide sequence of betaAXBA1 sense primer

<400> SEQUENCE: 31

```
ctagtctaga atgcccttgc tttggctgag agg                                33
```

<210> SEQ ID NO 32
<211> LENGTH: 40
<212> TYPE: DNA
<213> ORGANISM: artificial
<220> FEATURE:
<223> OTHER INFORMATION: Nucleotide sequence of betaA-NOT1 antisense
      primer

<400> SEQUENCE: 32

```
gctagcggcc gcctatgagc acccacactc ctccacgatc                         40
```

<210> SEQ ID NO 33
<211> LENGTH: 66
<212> TYPE: DNA
<213> ORGANISM: artificial
<220> FEATURE:
<223> OTHER INFORMATION: Nucleotide sequence of betaA-SCUT (site1)
      sense primer

<400> SEQUENCE: 33

```
atctcatcga gaaagaaacg ctcagtctca tcgggcttgg agtgtgatgg caaggtcaac   60
atctgc                                                              66
```

<210> SEQ ID NO 34
<211> LENGTH: 66
<212> TYPE: DNA
<213> ORGANISM: artificial
<220> FEATURE:
<223> OTHER INFORMATION: Nucleotide sequence of betaA-SCUT (site1)
      antisense primer

<400> SEQUENCE: 34

```
cgatgagact gagcgtttct ttctcgatga gatatgaggg tggtcttcag actgccgggc   60
ctgcag                                                              66
```

<210> SEQ ID NO 35
<211> LENGTH: 27
<212> TYPE: DNA
<213> ORGANISM: artificial
<220> FEATURE:
<223> OTHER INFORMATION: Nucleotide sequence of betaA-M418A sense

```
                        primer
<400> SEQUENCE: 35
gacattcaga acgcgatcgt ggaggag                                          27

<210> SEQ ID NO 36
<211> LENGTH: 27
<212> TYPE: DNA
<213> ORGANISM: artificial
<220> FEATURE:
<223> OTHER INFORMATION: Nucleotide sequence of betaA-M418A antisense
      primer

<400> SEQUENCE: 36
ctcctccacg atcgcgttct gaatgtc                                          27

<210> SEQ ID NO 37
<211> LENGTH: 426
<212> TYPE: PRT
<213> ORGANISM: artificial
<220> FEATURE:
<223> OTHER INFORMATION: Amino acid sequence of human betaA-subunit with
      A347H mutation

<400> SEQUENCE: 37
```

Met Pro Leu Leu Trp Leu Arg Gly Phe Leu Leu Ala Ser Cys Trp Ile
1               5                   10                  15

Ile Val Arg Ser Ser Pro Thr Pro Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125

Ser Gly Thr Ala Arg Lys Thr Leu His Phe Glu Ile Ser Lys Glu Gly
    130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190

Glu Glu Val Gly Leu Lys Gly Glu Arg Ser Glu Leu Leu Leu Ser Glu
        195                 200                 205

Lys Val Val Asp Ala Arg Lys Ser Thr Trp His Val Phe Pro Val Ser
    210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys

```
                260                 265                 270
Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Tyr His His Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
            370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 38
<211> LENGTH: 426
<212> TYPE: PRT
<213> ORGANISM: artificial
<220> FEATURE:
<223> OTHER INFORMATION: Amino acid sequence of human betaA-subunit with
      Y345G mutation

<400> SEQUENCE: 38

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
                20                  25                  30

Pro Asp Cys Pro Ser Cys Ala Leu Ala Ala Leu Pro Lys Asp Val Pro
            35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
            115                 120                 125

Ser Gly Thr Ala Arg Lys Thr Leu His Phe Glu Ile Ser Lys Glu Gly
            130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
            180                 185                 190
```

-continued

```
Glu Glu Val Gly Leu Lys Gly Glu Arg Ser Glu Leu Leu Leu Ser Glu
            195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Glu Glu Gly Glu Gly Lys Lys
            260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Gly His Ala Asn Tyr Cys Glu Gly
            340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 39
<211> LENGTH: 426
<212> TYPE: PRT
<213> ORGANISM: artificial
<220> FEATURE:
<223> OTHER INFORMATION: Amino acid seuqence of human betaA-subunit with
      A347H/Y345G mutation

<400> SEQUENCE: 39

Met Pro Leu Leu Trp Leu Arg Gly Phe Leu Leu Ala Ser Cys Trp Ile
1               5                   10                  15

Ile Val Arg Ser Ser Pro Thr Pro Gly Ser Glu Gly His Ser Ala Ala
            20                  25                  30

Pro Asp Cys Pro Ser Cys Ala Leu Ala Ala Leu Pro Lys Asp Val Pro
        35                  40                  45

Asn Ser Gln Pro Glu Met Val Glu Ala Val Lys Lys His Ile Leu Asn
    50                  55                  60

Met Leu His Leu Lys Lys Arg Pro Asp Val Thr Gln Pro Val Pro Lys
65                  70                  75                  80

Ala Ala Leu Leu Asn Ala Ile Arg Lys Leu His Val Gly Lys Val Gly
                85                  90                  95

Glu Asn Gly Tyr Val Glu Ile Glu Asp Asp Ile Gly Arg Arg Ala Glu
            100                 105                 110

Met Asn Glu Leu Met Glu Gln Thr Ser Glu Ile Ile Thr Phe Ala Glu
        115                 120                 125
```

```
Ser Gly Thr Ala Arg Lys Thr Leu His Phe Glu Ile Ser Lys Glu Gly
130                 135                 140

Ser Asp Leu Ser Val Val Glu Arg Ala Glu Val Trp Leu Phe Leu Lys
145                 150                 155                 160

Val Pro Lys Ala Asn Arg Thr Arg Thr Lys Val Thr Ile Arg Leu Phe
                165                 170                 175

Gln Gln Gln Lys His Pro Gln Gly Ser Leu Asp Thr Gly Glu Glu Ala
                180                 185                 190

Glu Glu Val Gly Leu Lys Gly Glu Arg Ser Glu Leu Leu Leu Ser Glu
            195                 200                 205

Lys Val Val Asp Ala Arg Lys Ser Thr Trp His Val Phe Pro Val Ser
210                 215                 220

Ser Ser Ile Gln Arg Leu Leu Asp Gln Gly Lys Ser Ser Leu Asp Val
225                 230                 235                 240

Arg Ile Ala Cys Glu Gln Cys Gln Glu Ser Gly Ala Ser Leu Val Leu
                245                 250                 255

Leu Gly Lys Lys Lys Lys Lys Glu Glu Glu Gly Glu Gly Lys Lys Lys
                260                 265                 270

Gly Gly Gly Glu Gly Gly Ala Gly Ala Asp Glu Glu Lys Glu Gln Ser
            275                 280                 285

His Arg Pro Phe Leu Met Leu Gln Ala Arg Gln Ser Glu Asp His Pro
290                 295                 300

His Arg Arg Arg Arg Gly Leu Glu Cys Asp Gly Lys Val Asn Ile
305                 310                 315                 320

Cys Cys Lys Lys Gln Phe Phe Val Ser Phe Lys Asp Ile Gly Trp Asn
                325                 330                 335

Asp Trp Ile Ile Ala Pro Ser Gly Gly His His Asn Tyr Cys Glu Gly
                340                 345                 350

Glu Cys Pro Ser His Ile Ala Gly Thr Ser Gly Ser Ser Leu Ser Phe
            355                 360                 365

His Ser Thr Val Ile Asn His Tyr Arg Met Arg Gly His Ser Pro Phe
370                 375                 380

Ala Asn Leu Lys Ser Cys Cys Val Pro Thr Lys Leu Arg Pro Met Ser
385                 390                 395                 400

Met Leu Tyr Tyr Asp Asp Gly Gln Asn Ile Ile Lys Lys Asp Ile Gln
                405                 410                 415

Asn Met Ile Val Glu Glu Cys Gly Cys Ser
            420                 425

<210> SEQ ID NO 40
<211> LENGTH: 440
<212> TYPE: PRT
<213> ORGANISM: artificial
<220> FEATURE:
<223> OTHER INFORMATION: Amino acid sequence of human betaA-subunit
      supercut with A361H mutation

<400> SEQUENCE: 40

Met Pro Leu Leu Trp Leu Arg Gly Phe Leu Leu Ala Ser Cys Trp Ile
1               5                   10                  15

Ile Val Arg Ser Asp Tyr Lys Asp Asp Asp Lys Ser Pro Thr Pro
            20                  25                  30

Gly Ser Glu Gly His Ser Ala Ala Pro Asp Cys Pro Ser Cys Ala Leu
        35                  40                  45

Ala Ala Leu Pro Lys Asp Val Pro Asn Ser Gln Pro Glu Met Val Glu
```

```
                50                  55                  60
Ala Val Lys Lys His Ile Leu Asn Met Leu His Leu Lys Lys Arg Pro
 65                  70                  75                  80

Asp Val Thr Gln Pro Val Pro Lys Ala Ala Leu Leu Asn Ala Ile Arg
                 85                  90                  95

Lys Leu His Val Gly Lys Val Gly Glu Asn Gly Tyr Val Glu Ile Glu
                100                 105                 110

Asp Asp Ile Gly Arg Arg Ala Glu Met Asn Glu Leu Met Glu Gln Thr
                115                 120                 125

Ser Glu Ile Ile Thr Phe Ala Glu Ser Gly Thr Ala Arg Lys Thr Leu
130                 135                 140

His Phe Glu Ile Ser Lys Glu Gly Ser Asp Leu Ser Val Val Glu Arg
145                 150                 155                 160

Ala Glu Val Trp Leu Phe Leu Lys Val Pro Lys Ala Asn Arg Thr Arg
                165                 170                 175

Thr Lys Val Thr Ile Arg Leu Phe Gln Gln Gln Lys His Pro Gln Gly
                180                 185                 190

Ser Leu Asp Thr Gly Glu Glu Ala Glu Glu Val Gly Leu Lys Gly Glu
                195                 200                 205

Arg Ser Glu Leu Leu Leu Ser Glu Lys Val Val Asp Ala Arg Lys Ser
210                 215                 220

Thr Trp His Val Phe Pro Val Ser Ser Ile Gln Arg Leu Leu Asp
225                 230                 235                 240

Gln Gly Lys Ser Ser Leu Asp Val Arg Ile Ala Cys Glu Gln Cys Gln
                245                 250                 255

Glu Ser Gly Ala Ser Leu Val Leu Leu Gly Lys Lys Lys Lys Lys Glu
                260                 265                 270

Glu Glu Gly Glu Gly Lys Lys Gly Gly Glu Gly Gly Ala Gly
                275                 280                 285

Ala Asp Glu Glu Lys Glu Gln Ser His Arg Pro Phe Leu Met Leu Gln
290                 295                 300

Ala Arg Gln Ser Glu Asp His Pro His Ile Ser Ser Arg Lys Lys Arg
305                 310                 315                 320

Ser Val Ser Ser Gly Leu Glu Cys Asp Gly Lys Val Asn Ile Cys Cys
                325                 330                 335

Lys Lys Gln Phe Phe Val Ser Phe Lys Asp Ile Gly Trp Asn Asp Trp
                340                 345                 350

Ile Ile Ala Pro Ser Gly Tyr His His Asn Tyr Cys Glu Gly Glu Cys
                355                 360                 365

Pro Ser His Ile Ala Gly Thr Ser Gly Ser Ser Leu Ser Phe His Ser
370                 375                 380

Thr Val Ile Asn His Tyr Arg Met Arg Gly His Ser Pro Phe Ala Asn
385                 390                 395                 400

Leu Lys Ser Cys Cys Val Pro Thr Lys Leu Arg Pro Met Ser Met Leu
                405                 410                 415

Tyr Tyr Asp Asp Gly Gln Asn Ile Ile Lys Lys Asp Ile Gln Asn Ala
                420                 425                 430

Ile Val Glu Glu Cys Gly Cys Ser
                435                 440

<210> SEQ ID NO 41
<211> LENGTH: 440
<212> TYPE: PRT
<213> ORGANISM: artificial
```

<220> FEATURE:
<223> OTHER INFORMATION: Amino acid sequence of human betaA-subunit
      supercut with Y359G mutation

<400> SEQUENCE: 41

```
Met Pro Leu Leu Trp Leu Arg Gly Phe Leu Leu Ala Ser Cys Trp Ile
1               5                   10                  15

Ile Val Arg Ser Asp Tyr Lys Asp Asp Asp Lys Ser Pro Thr Pro
                20                  25                  30

Gly Ser Glu Gly His Ser Ala Ala Pro Asp Cys Pro Ser Cys Ala Leu
            35                  40                  45

Ala Ala Leu Pro Lys Asp Val Pro Asn Ser Gln Pro Glu Met Val Glu
50                  55                  60

Ala Val Lys Lys His Ile Leu Asn Met Leu His Leu Lys Lys Arg Pro
65                  70                  75                  80

Asp Val Thr Gln Pro Val Pro Lys Ala Ala Leu Leu Asn Ala Ile Arg
                85                  90                  95

Lys Leu His Val Gly Lys Val Gly Glu Asn Gly Tyr Val Glu Ile Glu
                100                 105                 110

Asp Asp Ile Gly Arg Arg Ala Glu Met Asn Glu Leu Met Glu Gln Thr
            115                 120                 125

Ser Glu Ile Ile Thr Phe Ala Glu Ser Gly Thr Ala Arg Lys Thr Leu
130                 135                 140

His Phe Glu Ile Ser Lys Glu Gly Ser Asp Leu Ser Val Val Glu Arg
145                 150                 155                 160

Ala Glu Val Trp Leu Phe Leu Lys Val Pro Lys Ala Asn Arg Thr Arg
                165                 170                 175

Thr Lys Val Thr Ile Arg Leu Phe Gln Gln Gln Lys His Pro Gln Gly
            180                 185                 190

Ser Leu Asp Thr Gly Glu Glu Ala Glu Glu Val Gly Leu Lys Gly Glu
            195                 200                 205

Arg Ser Glu Leu Leu Leu Ser Glu Lys Val Val Asp Ala Arg Lys Ser
            210                 215                 220

Thr Trp His Val Phe Pro Val Ser Ser Ser Ile Gln Arg Leu Leu Asp
225                 230                 235                 240

Gln Gly Lys Ser Ser Leu Asp Val Arg Ile Ala Cys Glu Gln Cys Gln
                245                 250                 255

Glu Ser Gly Ala Ser Leu Val Leu Leu Gly Lys Lys Lys Lys Lys Glu
                260                 265                 270

Glu Glu Gly Glu Gly Lys Lys Gly Gly Glu Gly Gly Ala Gly
            275                 280                 285

Ala Asp Glu Glu Lys Glu Gln Ser His Arg Pro Phe Leu Met Leu Gln
290                 295                 300

Ala Arg Gln Ser Glu Asp His Pro His Ile Ser Ser Arg Lys Lys Arg
305                 310                 315                 320

Ser Val Ser Ser Gly Leu Glu Cys Asp Gly Lys Val Asn Ile Cys Cys
                325                 330                 335

Lys Lys Gln Phe Phe Val Ser Phe Lys Asp Ile Gly Trp Asn Asp Trp
                340                 345                 350

Ile Ile Ala Pro Ser Gly Gly His Ala Asn Tyr Cys Glu Gly Glu Cys
                355                 360                 365

Pro Ser His Ile Ala Gly Thr Ser Gly Ser Ser Leu Ser Phe His Ser
            370                 375                 380

Thr Val Ile Asn His Tyr Arg Met Arg Gly His Ser Pro Phe Ala Asn
```

```
385                 390                 395                 400
Leu Lys Ser Cys Cys Val Pro Thr Lys Leu Arg Pro Met Ser Met Leu
                405                 410                 415

Tyr Tyr Asp Asp Gly Gln Asn Ile Ile Lys Lys Asp Ile Gln Asn Ala
            420                 425                 430

Ile Val Glu Glu Cys Gly Cys Ser
        435                 440

<210> SEQ ID NO 42
<211> LENGTH: 440
<212> TYPE: PRT
<213> ORGANISM: artificial
<220> FEATURE:
<223> OTHER INFORMATION: Amino acid sequence of human betaA-subunit
      supercut with A361H/Y359G mutation

<400> SEQUENCE: 42

Met Pro Leu Leu Trp Leu Arg Gly Phe Leu Leu Ala Ser Cys Trp Ile
1               5                   10                  15

Ile Val Arg Ser Asp Tyr Lys Asp Asp Asp Lys Ser Pro Thr Pro
            20                  25                  30

Gly Ser Glu Gly His Ser Ala Ala Pro Asp Cys Pro Ser Cys Ala Leu
            35                  40                  45

Ala Ala Leu Pro Lys Asp Val Pro Asn Ser Gln Pro Glu Met Val Glu
50                  55                  60

Ala Val Lys Lys His Ile Leu Asn Met Leu His Leu Lys Lys Arg Pro
65                  70                  75                  80

Asp Val Thr Gln Pro Val Pro Lys Ala Ala Leu Leu Asn Ala Ile Arg
                85                  90                  95

Lys Leu His Val Gly Lys Val Gly Glu Asn Gly Tyr Val Glu Ile Glu
                100                 105                 110

Asp Asp Ile Gly Arg Arg Ala Glu Met Asn Glu Leu Met Glu Gln Thr
            115                 120                 125

Ser Glu Ile Ile Thr Phe Ala Glu Ser Gly Thr Ala Arg Lys Thr Leu
130                 135                 140

His Phe Glu Ile Ser Lys Glu Gly Ser Asp Leu Ser Val Val Glu Arg
145                 150                 155                 160

Ala Glu Val Trp Leu Phe Leu Lys Val Pro Lys Ala Asn Arg Thr Arg
                165                 170                 175

Thr Lys Val Thr Ile Arg Leu Phe Gln Gln Gln Lys His Pro Gln Gly
            180                 185                 190

Ser Leu Asp Thr Gly Glu Glu Ala Glu Val Gly Leu Lys Gly Glu
            195                 200                 205

Arg Ser Glu Leu Leu Leu Ser Glu Lys Val Val Asp Ala Arg Lys Ser
210                 215                 220

Thr Trp His Val Phe Pro Val Ser Ser Ser Ile Gln Arg Leu Leu Asp
225                 230                 235                 240

Gln Gly Lys Ser Ser Leu Asp Val Arg Ile Ala Cys Glu Gln Cys Gln
                245                 250                 255

Glu Ser Gly Ala Ser Leu Val Leu Leu Gly Lys Lys Lys Lys Glu
                260                 265                 270

Glu Glu Gly Glu Gly Lys Lys Lys Gly Gly Gly Glu Gly Gly Ala Gly
            275                 280                 285

Ala Asp Glu Glu Lys Glu Gln Ser His Arg Pro Phe Leu Met Leu Gln
            290                 295                 300
```

```
Ala Arg Gln Ser Glu Asp His Pro His Ile Ser Arg Lys Lys Arg
305                 310                 315                 320

Ser Val Ser Ser Gly Leu Glu Cys Asp Gly Lys Val Asn Ile Cys Cys
                325                 330                 335

Lys Lys Gln Phe Phe Val Ser Phe Lys Asp Ile Gly Trp Asn Asp Trp
            340                 345                 350

Ile Ile Ala Pro Ser Gly Gly His His Asn Tyr Cys Glu Gly Glu Cys
            355                 360                 365

Pro Ser His Ile Ala Gly Thr Ser Gly Ser Ser Leu Ser Phe His Ser
    370                 375                 380

Thr Val Ile Asn His Tyr Arg Met Arg Gly His Ser Pro Phe Ala Asn
385                 390                 395                 400

Leu Lys Ser Cys Cys Val Pro Thr Lys Leu Arg Pro Met Ser Met Leu
                405                 410                 415

Tyr Tyr Asp Asp Gly Gln Asn Ile Ile Lys Lys Asp Ile Gln Asn Ala
                420                 425                 430

Ile Val Glu Glu Cys Gly Cys Ser
                435                 440
```

<210> SEQ ID NO 43
<211> LENGTH: 1224
<212> TYPE: DNA
<213> ORGANISM: artificial
<220> FEATURE:
<223> OTHER INFORMATION: Nucleotide sequence encoding super-cut variant of human inhibin betaB-subunit with FLAG tag: with a modified signal sequence

<400> SEQUENCE: 43

```
atggacgggc tgcccggtcg ggcgctgggg gccgcctgcc ttctgctgct ggcggccggc      60
tggctggggc ctgaggcctg ggctcaccc acgccccgc cgacgcctgc cgcgccgccg       120
ccacccccgc cacccggatc cccgggtggc tcgcaggaca cctgtacgtc gtgcggcggc     180
ttccggcggc cagaggagct cggccgagtg gacggcgact tcctggaggc ggtgaagcgg     240
cacatcttga ccgcctgca gatgcggggc cggcccaaca tcacgcacgc cgtgcctaag      300
gccgccatgg tcacggccct cgcaagctg cacgcgggca aggtgcgcga ggacggccgc      360
gtggagatcc gccacctcga cggccacgcc agcccgggcg ccgacggcca ggagcgcgtt     420
tccgaaatca tcagcttcgc cgagacagat ggcctcgcct cctcccgggt ccgcctatac     480
ttcttcatct ccaacgaagg caaccagaac ctgtttgtgg tccaggccag cctgtggctt     540
tacctgaaac tcctgcccta cgtcctggag aagggcagcc ggcggaaggt gcgggtcaaa     600
gtgtacttcc aggagcaggg ccacggtgac aggtggaaca tggtggagaa gagggtggac     660
ctcaagcgca gcggctggca taccttccca ctcacggagg ccatccaggc cttgtttgag     720
cggggcgagc ggcgactcaa cctagacgtg cagtgtgaca gctgccagga gctggccgtg     780
gtgccggtgt tcgtggaccc caggcgaagag tcgcaccggc cctttgtggt ggtgcaggct     840
cggctgggcg acagcaggca ccgcattcgc aagcgaggcc tggagtgcga tggccggacc     900
aacctctgtt gcaggcaaca gttcttcatt gacttccgcc tcatcggctg gaacgactgg     960
atcatagcac ccaccggcta ctacgggaac tactgtgagg gcagctgccc agcctacctg     1020 gcagggggtcc ccggctctgc ctcctccttc cacacggctg tggtgaacca gtaccgcatg     1080
cggggtctga accccggcac ggtgaactcc tgctgcattc ccaccaagct gagcaccatg     1140
tccatgctgt acttcgatga tgagtacaac atcgtcaagc gggacgtgcc caacatgatt     1200
```

```
gtggaggagt gcggctgcgc ctga                                          1224

<210> SEQ ID NO 44
<211> LENGTH: 418
<212> TYPE: PRT
<213> ORGANISM: artificial
<220> FEATURE:
<223> OTHER INFORMATION: Amino acid seuqence of super-cut variant of
      human inhibin betaB-subunit: with a modified signal sequence

<400> SEQUENCE: 44

Met Asp Gly Leu Pro Gly Arg Ala Leu Gly Ala Ala Cys Leu Leu Leu
1               5                   10                  15

Leu Ala Ala Gly Trp Leu Gly Pro Glu Ala Trp Gly Asp Tyr Lys Asp
            20                  25                  30

Asp Asp Asp Lys Ser Pro Thr Pro Pro Pro Thr Pro Ala Ala Pro Pro
        35                  40                  45

Pro Pro Pro Pro Pro Gly Ser Pro Gly Gly Ser Gln Asp Thr Cys Thr
    50                  55                  60

Ser Cys Gly Gly Phe Arg Arg Pro Glu Glu Leu Gly Arg Val Asp Gly
65                  70                  75                  80

Asp Phe Leu Glu Ala Val Lys Arg His Ile Leu Ser Arg Leu Gln Met
                85                  90                  95

Arg Gly Arg Pro Asn Ile Thr His Ala Val Pro Lys Ala Ala Met Val
            100                 105                 110

Thr Ala Leu Arg Lys Leu His Ala Gly Lys Val Arg Glu Asp Gly Arg
        115                 120                 125

Val Glu Ile Pro His Leu Asp Gly His Ala Ser Pro Gly Ala Asp Gly
    130                 135                 140

Gln Glu Arg Val Ser Glu Ile Ile Ser Phe Ala Glu Thr Asp Gly Leu
145                 150                 155                 160

Ala Ser Ser Arg Val Arg Leu Tyr Phe Phe Ile Ser Asn Glu Gly Asn
                165                 170                 175

Gln Asn Leu Phe Val Val Gln Ala Ser Leu Trp Leu Tyr Leu Lys Leu
            180                 185                 190

Leu Pro Tyr Val Leu Glu Lys Gly Ser Arg Arg Lys Val Arg Val Lys
        195                 200                 205

Val Tyr Phe Gln Glu Gln Gly His Gly Asp Arg Trp Asn Met Val Glu
    210                 215                 220

Lys Arg Val Asp Leu Lys Arg Ser Gly Trp His Thr Phe Pro Leu Thr
225                 230                 235                 240

Glu Ala Ile Gln Ala Leu Phe Glu Arg Gly Glu Arg Arg Leu Asn Leu
                245                 250                 255

Asp Val Gln Cys Asp Ser Cys Gln Glu Leu Ala Val Val Pro Val Phe
            260                 265                 270

Val Asp Pro Gly Glu Glu Ser His Arg Pro Phe Val Val Val Gln Ala
        275                 280                 285

Arg Leu Gly Asp Ile Ser Ser Arg Lys Lys Arg Ser Val Ser Ser Gly
    290                 295                 300

Leu Glu Cys Asp Gly Arg Thr Asn Leu Cys Cys Arg Gln Gln Phe Phe
305                 310                 315                 320

Ile Asp Phe Arg Leu Ile Gly Trp Asn Asp Trp Ile Ile Ala Pro Thr
                325                 330                 335

Gly Tyr Tyr Gly Asn Tyr Cys Glu Gly Ser Cys Pro Ala Tyr Leu Ala
            340                 345                 350

-continued

```
Gly Val Pro Gly Ser Ala Ser Ser Phe His Thr Ala Val Val Asn Gln
        355             360                 365

Tyr Arg Met Arg Gly Leu Asn Pro Gly Thr Val Asn Ser Cys Cys Ile
    370             375             380

Pro Thr Lys Leu Ser Thr Met Ser Met Leu Tyr Phe Asp Asp Glu Tyr
385             390             395             400

Asn Ile Val Lys Arg Asp Val Pro Asn Ala Ile Val Glu Glu Cys Gly
                405             410             415

Cys Ala
```

The invention claimed is:

1. A mammalian inhibin analog precursor protein comprising a heterodimer of α-subunit and β-subunit precursors, wherein:
   i) the α-subunit has an amino acid sequence of SEQ ID NO:6 or an amino acid sequence having at least 90% sequence identity thereto after optimal alignment, and
   ii) the β-subunit is
   a $β_A$-subunit having an amino acid sequence of SEQ ID NO: 2 or an amino acid sequence having at least 90% sequence identity thereto after optimal alignment, or
   a $β_B$-subunit having an amino acid sequence of SEQ ID NO: 12 or an amino acid sequence having at least 90% sequence identity thereto after optimal alignment;
   wherein the α-subunit and the β-subunit precursors each have proprotein convertase cleavage sites, wherein at least one proprotein convertase cleavage sites is modified by an amino acid substitution mutation to render it more efficiently cleaved by the proprotein convertase to generate bioactive inhibin, and wherein the modified proprotein convertase cleavage site is ISSRKKRSVSS (SEQ ID NO:18).

2. The inhibin analog precursor protein of claim 1 wherein a proprotein convertase cleavage site in each of the α-subunit and the β-subunit precursors is modified by the amino acid substitution mutation.

3. The inhibin analog precursor protein of claim 1 wherein the inhibin is of human origin.

4. The inhibin analog precursor protein of claim 3 wherein the α-subunit precursor further comprises a secondary proprotein convertase cleavage site which is modified by an amino acid substitution mutation to render it more efficiently cleaved by the proprotein convertase.

5. The inhibin analog precursor protein of claim 4 wherein a primary proprotein convertase site in the α-subunit at $^{229}$RARR$^{232}$ (SEQ ID NO:45) is replaced by $^{229}$ISSRKKRSVSS$^{239}$ (SEQ ID NO:18).

6. The inhibin analog precursor protein of claim 4 wherein a secondary site in the α-subunit at $^{56}$RRLPRR$^{61}$ (SEQ ID NO:46) is replaced by $^{56}$RRRRRR$^{61}$ (SEQ ID NO:47).

7. The inhibin analog precursor protein of claim 5 further comprising a poly-his tag.

8. The inhibin analog precursor protein of claim 4 wherein the β-subunit is a $β_A$-subunit wherein the cleavage site $^{306}$RRRRR$^{310}$ (SEQ ID NO:22) in the $β_A$-subunit is replaced with the amino acid sequence $^{306}$ISSRKKRSVSS$^{316}$ (SEQ ID NO:18).

9. The inhibin analog precursor protein of claim 4 wherein the β-subunit is a $β_B$-subunit wherein the cleavage site $^{288}$RIRKR$^{292}$ (SEQ ID NO:48) in the $β_B$-subunit is replaced by the amino acid sequence $^{288}$ISSRKKRSVSS$^{298}$ (SEQ ID NO:18).

10. The inhibin analog precursor protein of claim 1 wherein the β-subunit comprises a mature domain that further comprises a single point mutation within a type I receptor (ALK4) binding epitope wherein the β-subunit is selected from the group consisting of a $β_A$-subunit comprising an M418A substitution mutation using the numbering system of SEQ ID NO:2; and a $β_B$-subunit comprising an M410A substitution mutation using the numbering system of SEQ ID NO:14.

11. The inhibin analog precursor protein of claim 8 wherein the $β_A$-subunit further comprises a FLAG tag comprising the amino acid sequence DYKDDDK (SEQ ID NO:16) between amino acids 27 and 28 of $β_A$ using the numbering system of SEQ ID NO:2.

12. The inhibin analog precursor protein of claim 1 further comprising a mutation at a homodimerization interface site on $β_A$- or $β_B$-subunit to reduce or eliminate the production of an active activin A or B selected from the group consisting of: (i) a mutation on the βA-subunit that is a substitution mutation selected from the group consisting of A347X$_1$, Y345Y$_2$, F326X$_3$, V392X$_4$, P393X$_5$ and L396X$_6$ using the numbering system of SEQ ID NO:2 wherein each of X$_1$, X$_2$, X$_3$, X$_4$, X$_5$ and X$_6$ is any amino acid except A, Y, F, V, P and L, respectively; the substitution mutation is A347H; and the substitution mutation is Y345G; and (ii) a mutation on the $β_B$-subunit that is a substitution mutation selected from the group consisting of F308X$_7$, Y327X$_8$, G329X$_9$, I373X$_{10}$, P374X$_{11}$ and L377X$_{12}$, using the numbering system of SEQ ID NO:12, wherein each of X$_7$, X$_8$, X$_9$, X$_{10}$, X$_{11}$ and X$_{12}$ is any amino acid except F, Y, G, I, P and L, respectively.

13. The inhibin analog precursor protein of claim 1 comprising an α-subunit having the amino acid sequence selected from the group consisting of (i) SEQ ID NO:8 or an amino acid sequence having at least 90% sequence identity to SEQ ID NO:8 after optimal alignment with the proviso that it comprises at least one modified proprotein convertase site to enable more efficient cleavage by the convertase; (ii) SEQ ID NO:10 or an amino acid sequence having at least 90% sequence identity to SEQ ID NO:10 after optimal alignment with the proviso that it comprises at least one modified proprotein convertase site to enable more efficient cleavage by the convertase; and comprising a $β_A$-subunit having the amino acid sequence selected from the group consisting of (iv) SEQ ID NOs:37-39 and an amino acid sequence having at least 90% sequence identity to SEQ ID NOs:37-39 after optimal alignment with the proviso that the $β_A$-subunit comprises at least one amino acid mutation to reduce dimerization in the formulation of an activin; and (v) SEQ ID NOs:40-42 and an amino acid sequence having at least 90% sequence identity to SEQ ID NOs:40-42 after optimal alignment with the proviso that the $β_A$-subunit comprises at least one amino acid mutation to reduce dimerization in the formulation of an activin.

14. The inhibin analog precursor protein of claim 1 comprising a $\beta_B$-subunit having the amino acid sequence as set forth in SEQ ID NO:14 or an amino acid sequence having at least 90% sequence identity to SEQ ID NO:14 after optimal alignment with the proviso that it comprises at least one modified proprotein convertase site to enable more efficient cleavage by the convertase.

15. A nucleic acid molecule encoding the inhibin analog precursor protein of claim 1.

16. The nucleic acid molecule of claim 15, wherein the nucleic acid sequence encoding the α-subunit of the inhibin analog precursor protein comprises the nucleotide sequence selected from the group consisting of SEQ ID NO:7 or a nucleotide sequence having at least about 90% identity thereto after optimal alignment or a nucleic acid capable of hybridizing to the complement of SEQ ID NO:7; and SEQ ID NO:9 or a nucleotide sequence having at least about 90% identity thereto after optimal alignment or a nucleic acid capable of hybridizing to the complement of SEQ ID NO:9.

17. A nucleic acid molecule of claim 15, wherein the nucleic acid sequence encoding the $\beta_A$-subunit of the inhibin analog precursor protein comprises the nucleotide sequence as set forth in SEQ ID NO:3 or a nucleotide sequence having at least about 90% identity thereto after optimal alignment or a nucleic acid capable of hybridizing to the complement of SEQ ID NO:3.

18. A nucleic acid molecule of claim 15 wherein the nucleic acid sequence encoding the $\beta_B$-subunit of the inhibin analog precursor protein comprises the nucleotide sequence as set forth in SEQ ID NO:13 or a nucleotide sequence having at least about 90% identity thereto after optimal alignment or a nucleic acid capable of hybridizing to the complement of SEQ ID NO:13.

19. An isolated cell or cell line comprising the nucleic acid of claim 15.

20. A method for generating a bioactive inhibin analog said method comprising co-expressing in a cell or cell line a nucleic acid molecule encoding an α-subunit having the amino acid sequence as set forth in SEQ ID NO:8 or an amino acid sequence having at least 90% sequence identity to SEQ ID NO:8 after optimal alignment with the proviso that it comprises at least one modified proprotein convertase site to enable more efficient cleavage by the convertase and a β-subunit having the amino acid sequence as set forth in SEQ ID NO:4 or an amino acid sequence having at least 90% sequence identity to SEQ ID NO:4 after optimal alignment with the proviso that it comprises at least one modified proprotein convertase site to enable more efficient cleavage by the convertase for a time and under conditions sufficient for an inhibin precursor protein to be produced, cleaved by a proprotein convertase and secreted from the cell or cell line as a bioactive inhibin analog.

21. The method of claim 20 wherein the bioactive inhibin analog is selected from the group consisting of inhibin A analog; and inhibin B analog.

\* \* \* \* \*